(12) United States Patent
Culbert et al.

(10) Patent No.: US 9,101,411 B2
(45) Date of Patent: Aug. 11, 2015

(54) METHOD AND APPARATUS FOR SPINAL FIXATION

(75) Inventors: Brad S. Culbert, Rancho Santa Margarita, CA (US); Larry Khoo, Studio City, CA (US); Bob Flower, Sun City, CA (US)

(73) Assignee: Interventional Spine, Inc., Irvine, CA (US)

(*) Notice: Subject to any disclaimer, the term of this patent is extended or adjusted under 35 U.S.C. 154(b) by 1062 days.

(21) Appl. No.: 13/078,760

(22) Filed: Apr. 1, 2011

(65) Prior Publication Data

US 2011/0218575 A1 Sep. 8, 2011

Related U.S. Application Data

(63) Continuation of application No. 11/738,371, filed on Apr. 20, 2007, now Pat. No. 7,938,832.

(60) Provisional application No. 60/800,568, filed on May 15, 2006, provisional application No. 60/794,171, filed on Apr. 21, 2006.

(51) Int. Cl.
*A61B 17/88* (2006.01)
*A61B 17/56* (2006.01)
(Continued)

(52) U.S. Cl.
CPC .......... *A61B 17/7064* (2013.01); *A61B 17/1757* (2013.01); *A61B 17/0218* (2013.01);
(Continued)

(58) Field of Classification Search
CPC ........... A61B 17/1757; A61B 17/7064; A61B 17/0218; A61B 17/1655; A61B 17/1671; A61B 17/8861; A61B 2017/922; A61B 2017/0046; A61B 2017/00469

USPC ........ 606/279, 79, 80, 86 A, 103, 96–99, 104
See application file for complete search history.

(56) References Cited

U.S. PATENT DOCUMENTS

| 5,167,664 A | 12/1992 | Hodorek |
| 5,234,431 A | 8/1993 | Keller |

(Continued)

FOREIGN PATENT DOCUMENTS

| DE | 198 32 798 | 11/1999 |
| EP | 0 625 336 | 11/1994 |

(Continued)

OTHER PUBLICATIONS

Office Action Communication pursuant to Article 96(2) EPC received in European Application No. 02719402.6 on Apr. 19, 2007.

(Continued)

*Primary Examiner* — Pedro Philogene
(74) *Attorney, Agent, or Firm* — Knobbe, Martens, Olson & Bear, LLP

(57) ABSTRACT

Fusion of cervical spinal vertebrae with one or more fixation devices can be accomplished with the described tools and methods. For example, a guidewire introducer can include a tubular introducer cannula and a handle. The handle can be angularly offset from the introducer cannula such that positioning of the introducer on the cervical spine does not interfere with a patient's head. A sheath assembly can include inner and outer sheath bodies and a handle. The handle is angularly offset from the sheath bodies such that the sheath assembly can be applied to the cervical spine without interference to the patient's head. The sheath body can be curved or straight. Various tools such as drills, tapping devices, compression tools, and pin release tools can be applied to the cervical spine through the sheath body to apply the fixation device. The tools can include elongate flexible shafts.

20 Claims, 55 Drawing Sheets

(51) Int. Cl.
*A61B 17/16* (2006.01)
*A61B 17/70* (2006.01)
*A61B 17/17* (2006.01)
A61B 17/02 (2006.01)
A61B 17/00 (2006.01)
A61B 17/92 (2006.01)

(52) U.S. Cl.
CPC ......... *A61B17/1655* (2013.01); *A61B 17/1671* (2013.01); *A61B 17/8861* (2013.01); *A61B 2017/0046* (2013.01); *A61B 2017/00469* (2013.01); *A61B 2017/922* (2013.01)

(56) References Cited

U.S. PATENT DOCUMENTS

| | | | |
|---|---|---|---|
| 5,370,647 | A | 12/1994 | Graber et al. |
| 5,649,931 | A | 7/1997 | Bryant et al. |
| 5,810,821 | A | 9/1998 | Vandewalle |
| 5,989,255 | A | 11/1999 | Pepper et al. |
| 6,022,352 | A | 2/2000 | Vandewalle |
| 6,066,142 | A | 5/2000 | Serbousek et al. |
| 6,251,111 | B1 | 6/2001 | Barker et al. |
| 6,267,767 | B1 | 7/2001 | Strobel et al. |
| 6,287,313 | B1 * | 9/2001 | Sasso ............................ 606/96 |
| 6,290,701 | B1 | 9/2001 | Enayati |
| 6,379,363 | B1 | 4/2002 | Herrington et al. |
| 6,488,693 | B2 | 12/2002 | Gannoe et al. |
| 6,520,907 | B1 | 2/2003 | Foley et al. |
| 6,562,046 | B2 | 5/2003 | Sasso |
| 6,632,224 | B2 | 10/2003 | Cachia et al. |
| 6,890,333 | B2 | 5/2005 | von Hoffmann et al. |
| 6,908,465 | B2 | 6/2005 | von Hoffmann et al. |
| 6,923,811 | B1 * | 8/2005 | Carl et al. .................. 623/17.11 |
| 6,929,606 | B2 | 8/2005 | Ritland |
| 7,326,211 | B2 | 2/2008 | Padget et al. |
| 7,422,594 | B2 | 9/2008 | Zander |
| 7,488,326 | B2 | 2/2009 | Elliott |
| 7,625,378 | B2 | 12/2009 | Foley |
| 7,887,548 | B2 * | 2/2011 | Usher et al. .................. 606/104 |
| 7,909,848 | B2 * | 3/2011 | Patel et al. .................... 606/201 |
| 7,938,832 | B2 * | 5/2011 | Culbert et al. ............. 606/86 A |
| 8,394,107 | B2 * | 3/2013 | Fanger et al. .................. 606/96 |
| 2001/0027320 | A1 | 10/2001 | Sasso |
| 2004/0186482 | A1 | 9/2004 | Kolb et al. |
| 2004/0260297 | A1 | 12/2004 | Padget et al. |
| 2005/0256525 | A1 | 11/2005 | Warren et al. |
| 2006/0030872 | A1 | 2/2006 | Culbert et al. |
| 2006/0085010 | A1 * | 4/2006 | Lieberman ..................... 606/99 |
| 2008/0097436 | A1 | 4/2008 | Culbert et al. |
| 2008/0108996 | A1 | 5/2008 | Padget et al. |
| 2008/0287981 | A1 | 11/2008 | Culbert et al. |
| 2009/0105745 | A1 * | 4/2009 | Culbert ....................... 606/192 |
| 2009/0149857 | A1 | 6/2009 | Culbert et al. |

FOREIGN PATENT DOCUMENTS

| | | |
|---|---|---|
| EP | 1 374 784 | 1/2004 |
| JP | 6 319742 A | 11/1994 |
| WO | WO 99/62417 | 12/1999 |
| WO | WO 00/67652 | 11/2000 |
| WO | WO 03/043488 | 5/2003 |
| WO | WO 2004/008949 | 1/2004 |
| WO | WO 2004/078220 | 9/2004 |
| WO | WO 2004/078221 | 9/2004 |
| WO | WO 2006/017507 | 2/2006 |
| WO | WO 2006/108067 | 10/2006 |
| WO | WO 2007/124130 | 11/2007 |

OTHER PUBLICATIONS

International Search Report and Written Opinion from corresponding PCT Application No. PCT/US07/09794, 8 pgs, mailed Apr. 17, 2008.
International Search Report for European Application No. 02719402.6, mailed on Apr. 19, 2007.
International Preliminary Report on Patentability of co-pending PCT Application No. PCT/US2007/009794, mailed Mar. 12, 2009, 5 pages.
Supplementary European Search Report for European Application No. 07755880.7, mailed on Apr. 28, 2011.

* cited by examiner

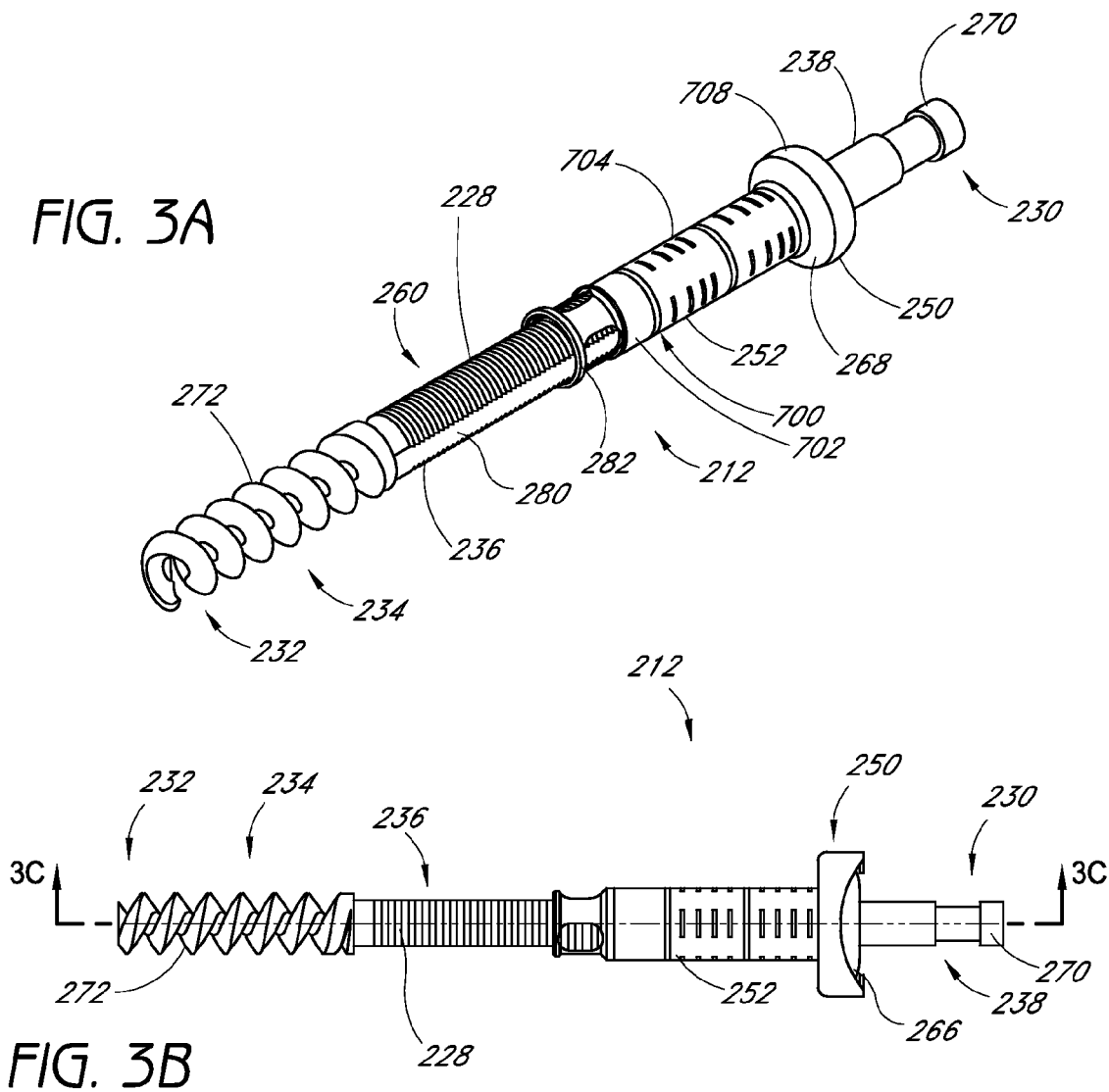
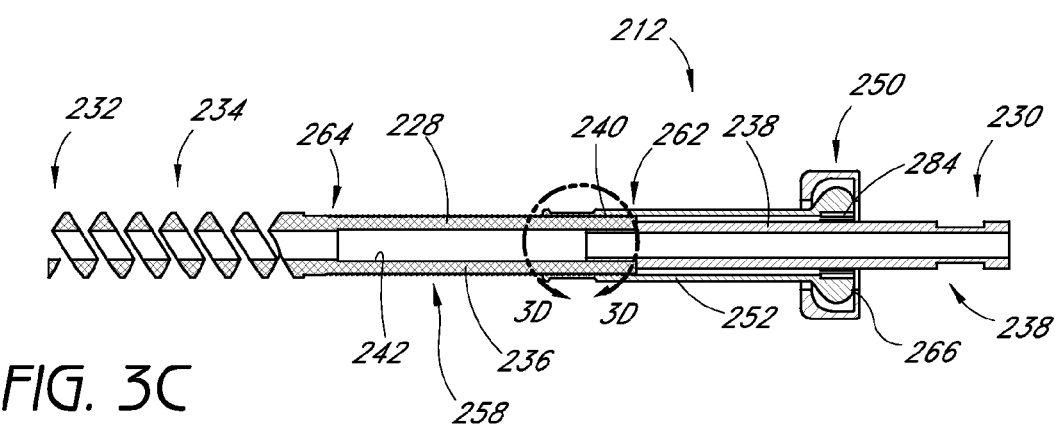

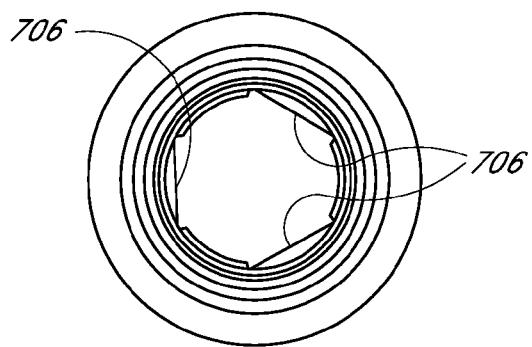
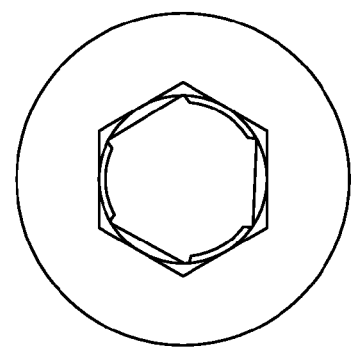
FIG. 4D          FIG. 4E
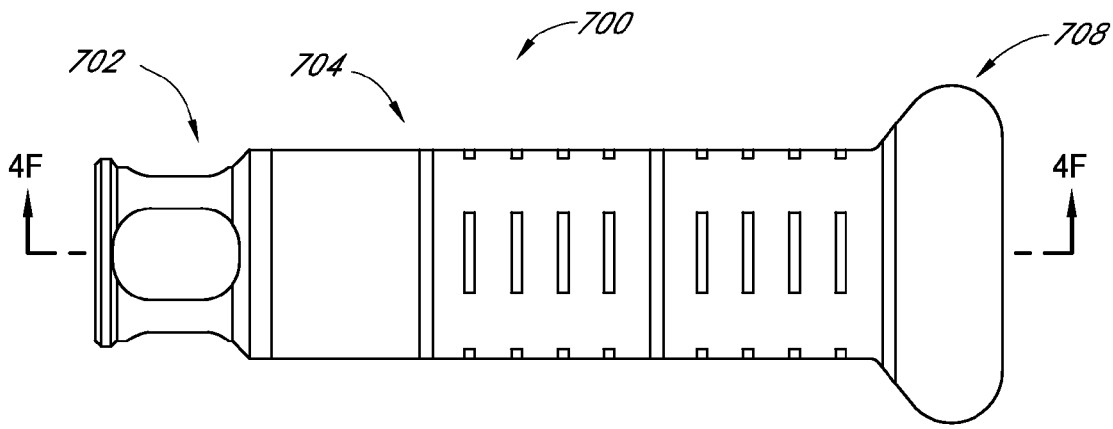
FIG. 4B
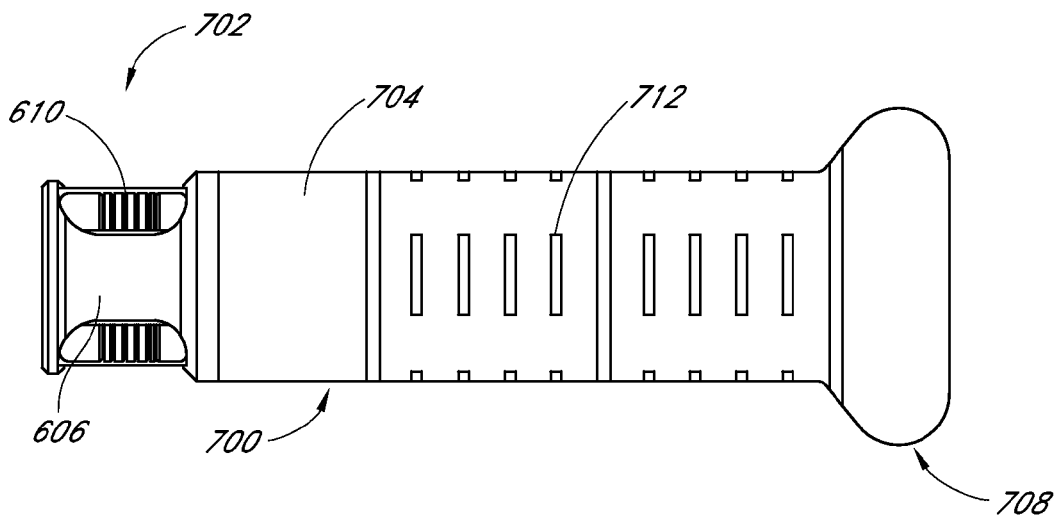
FIG. 4C

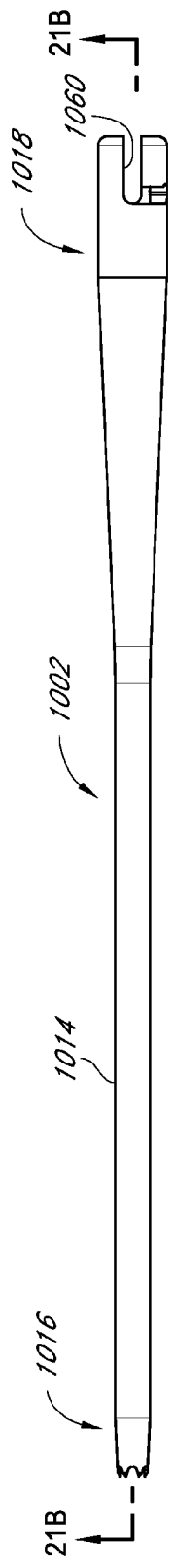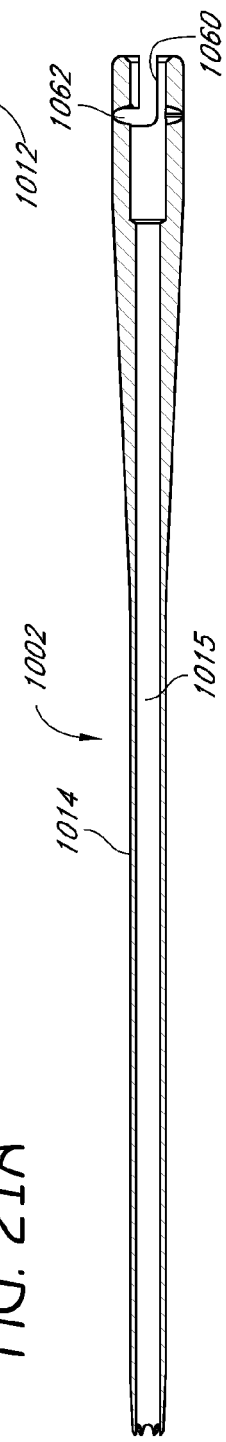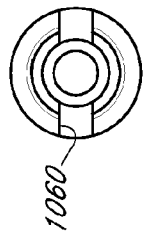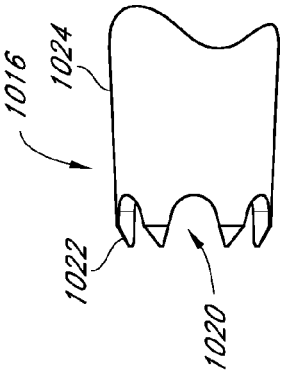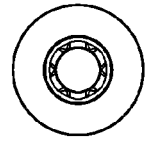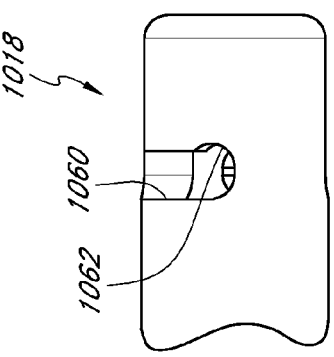
FIG. 21A
FIG. 21B
FIG. 21C
FIG. 21D
FIG. 21E
FIG. 21F

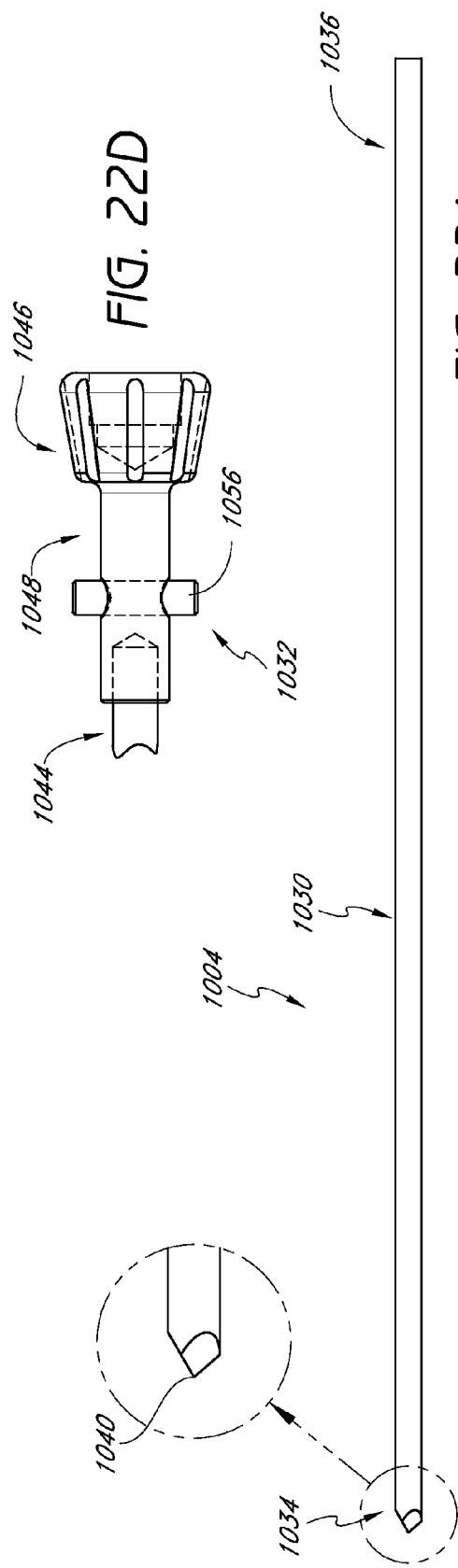
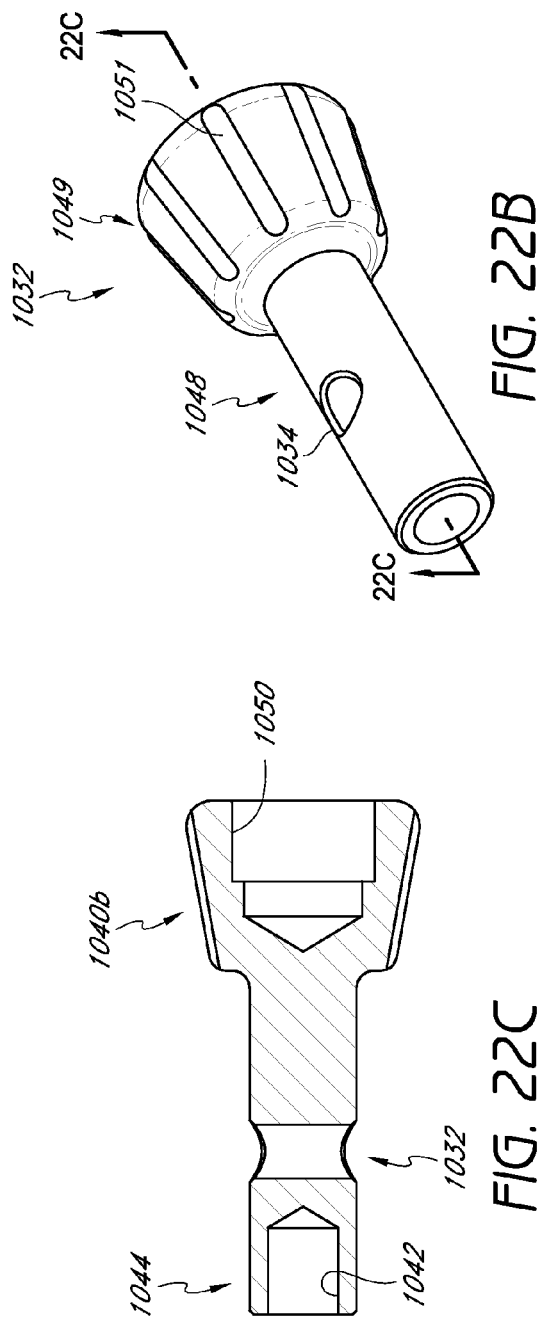

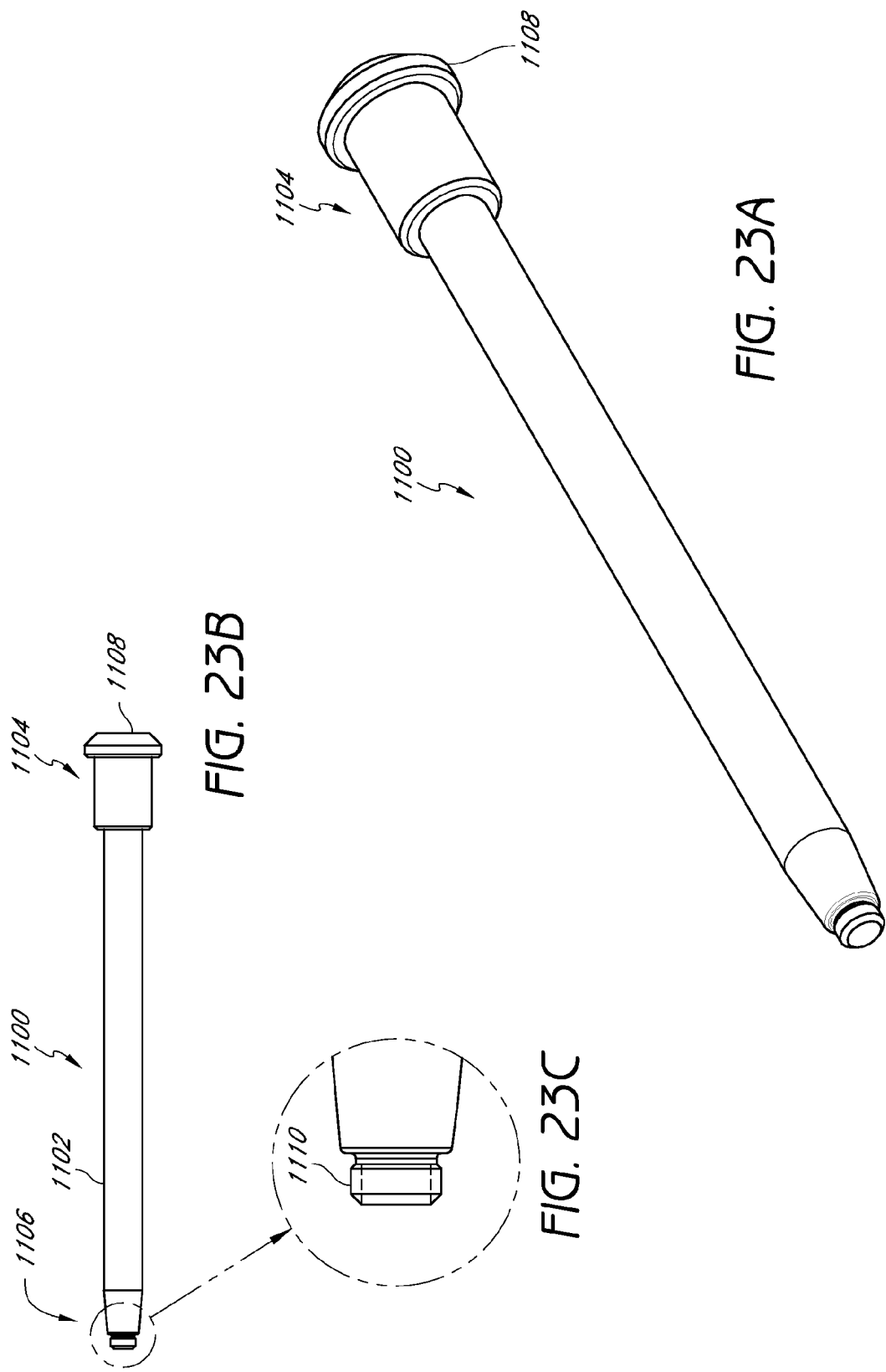

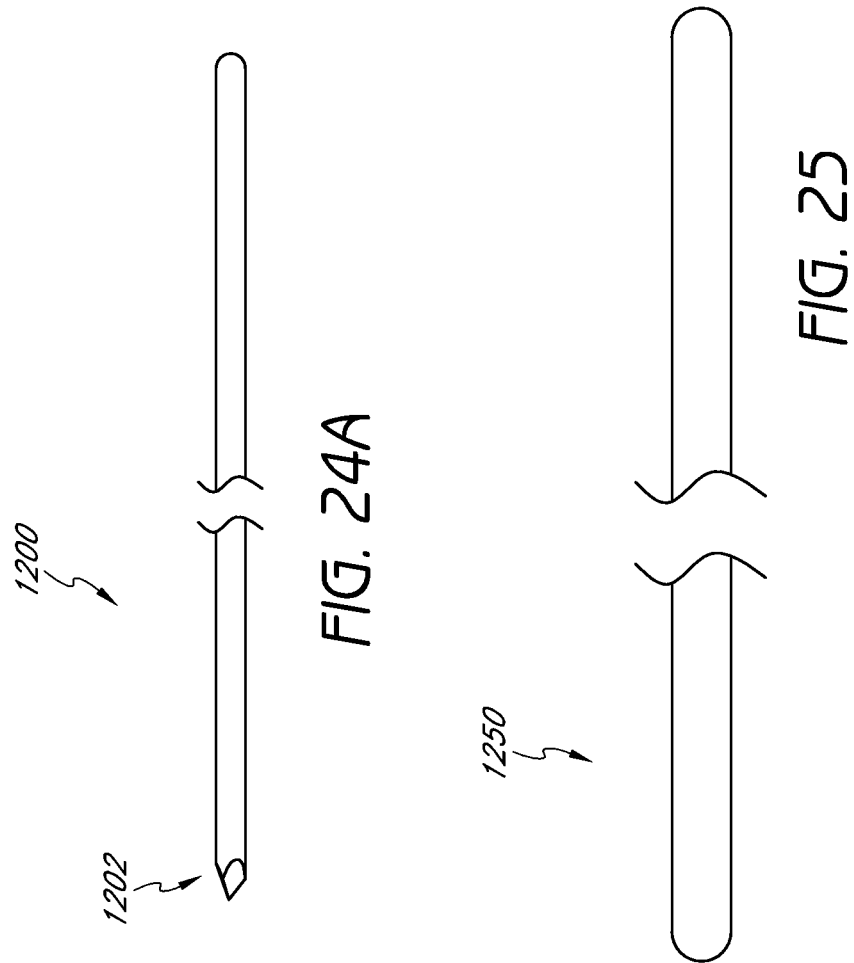
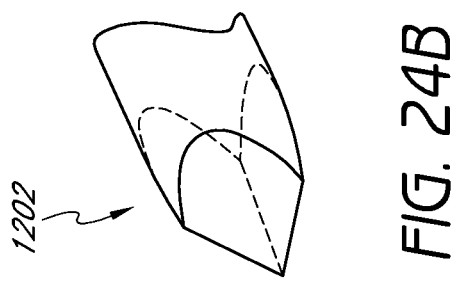

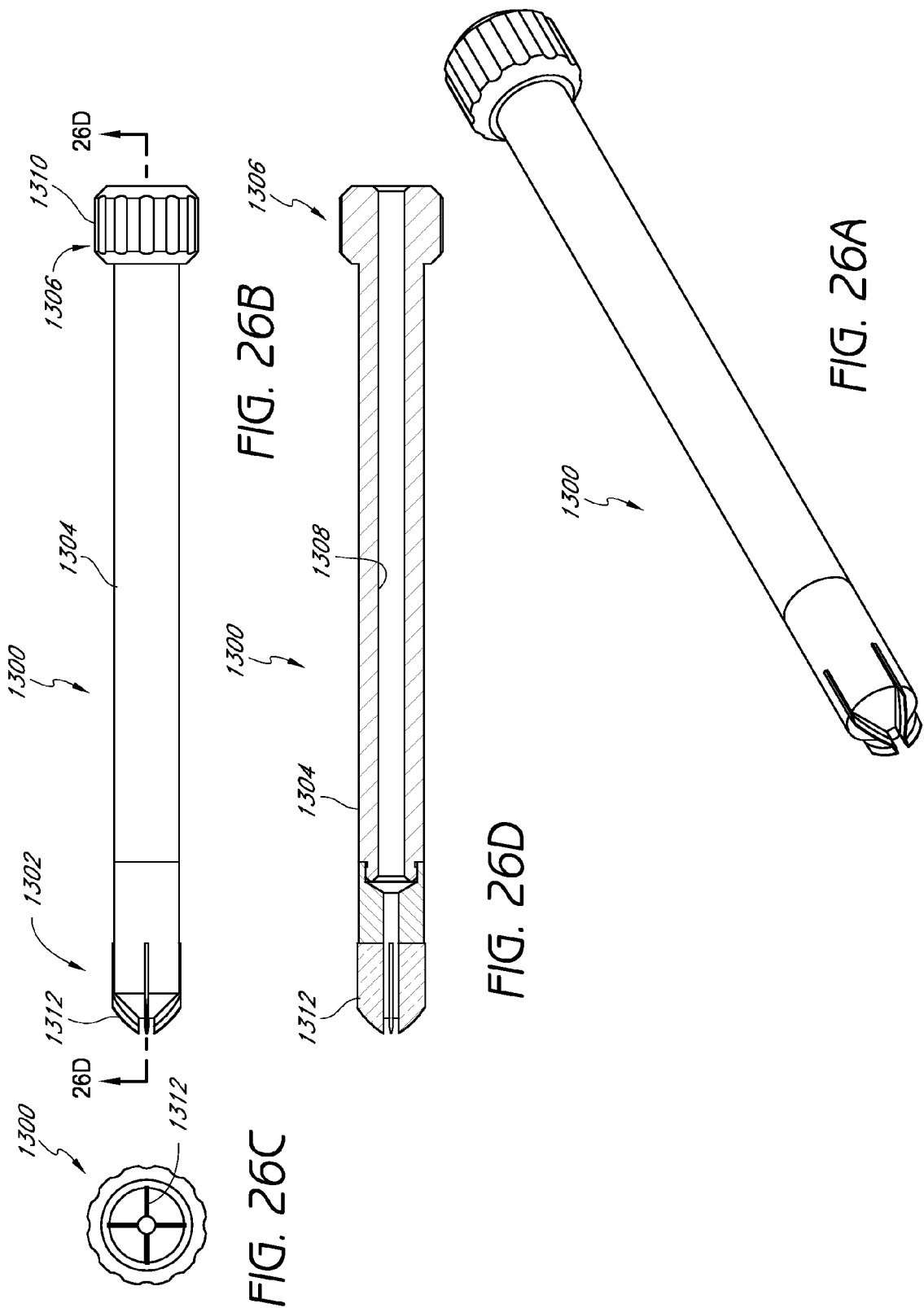

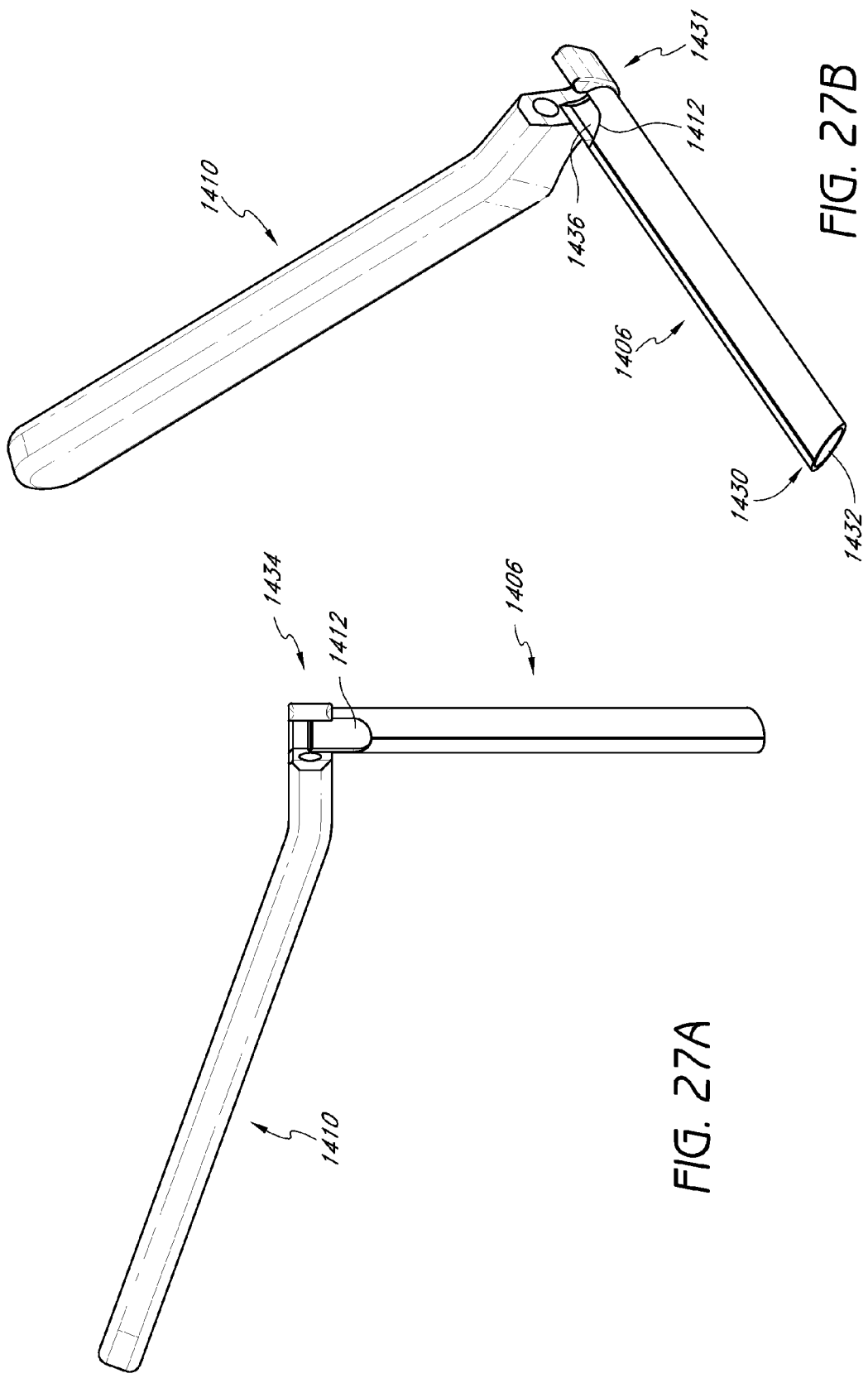

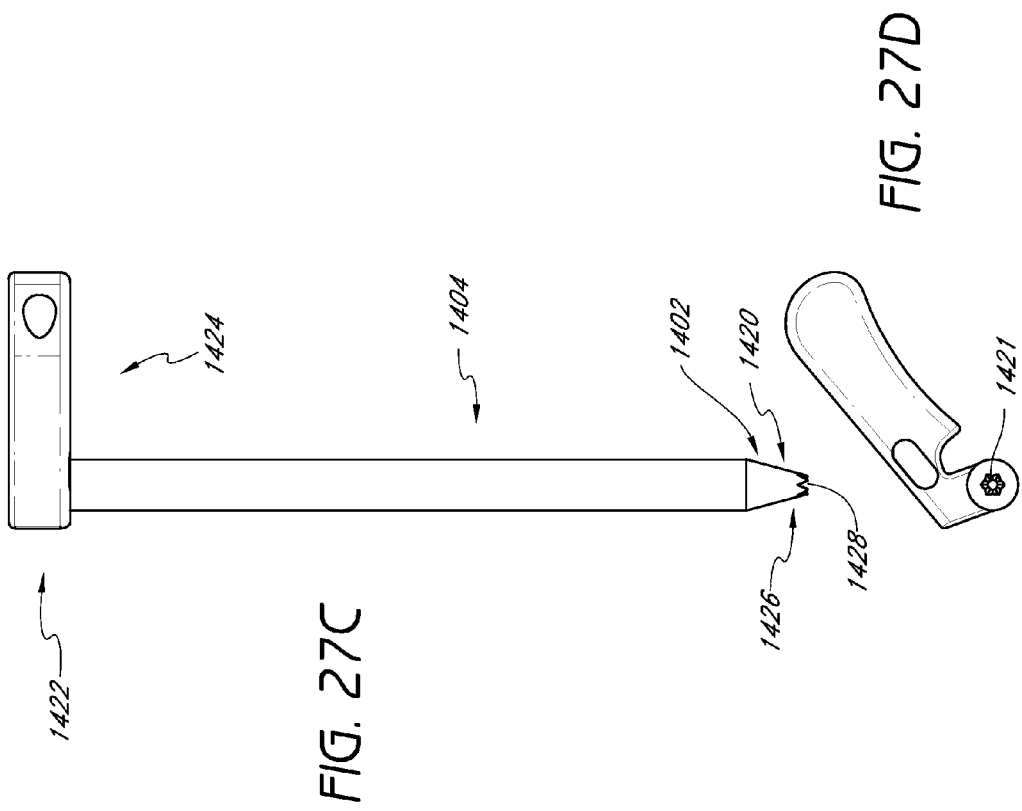

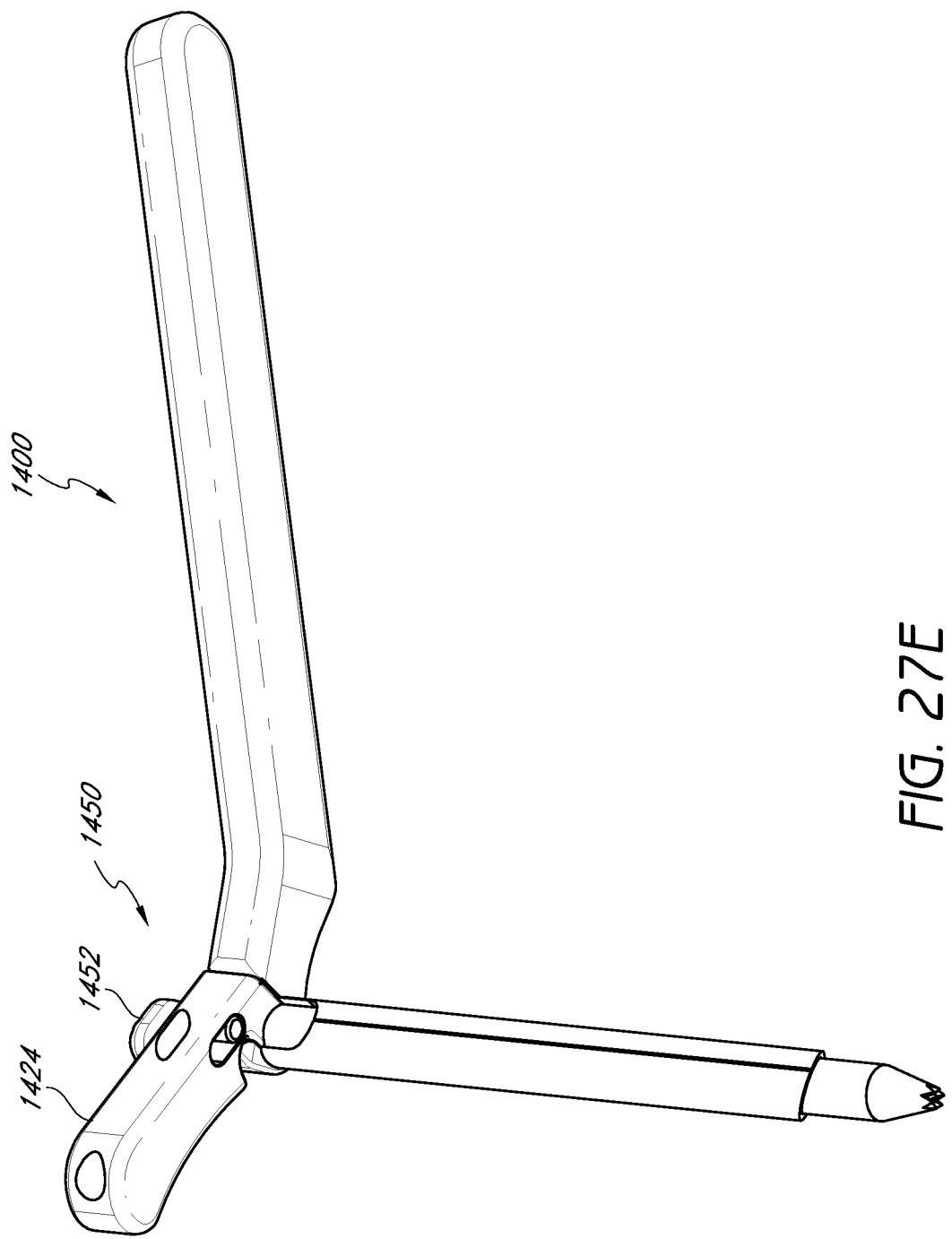

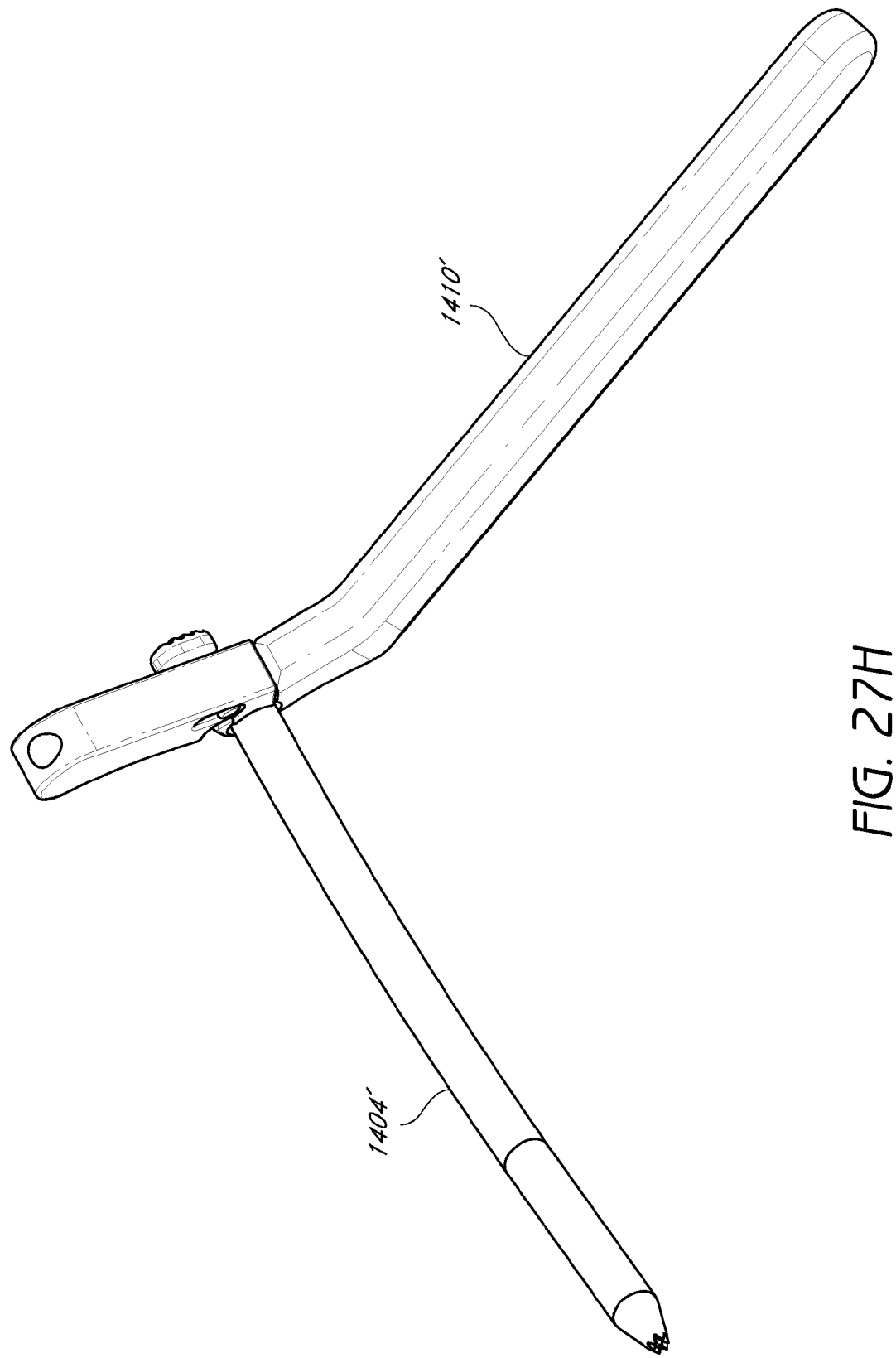

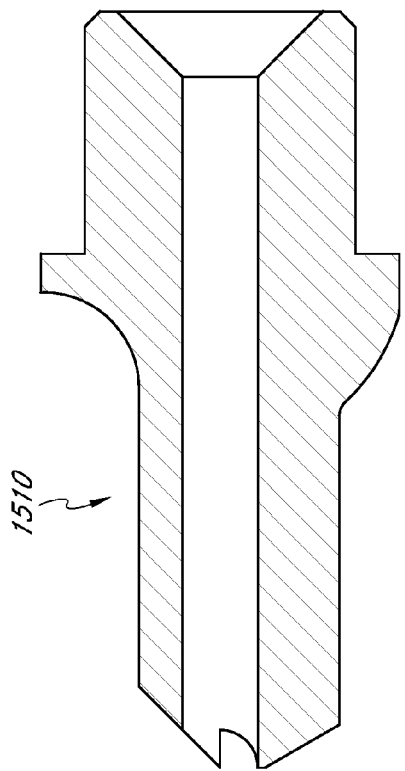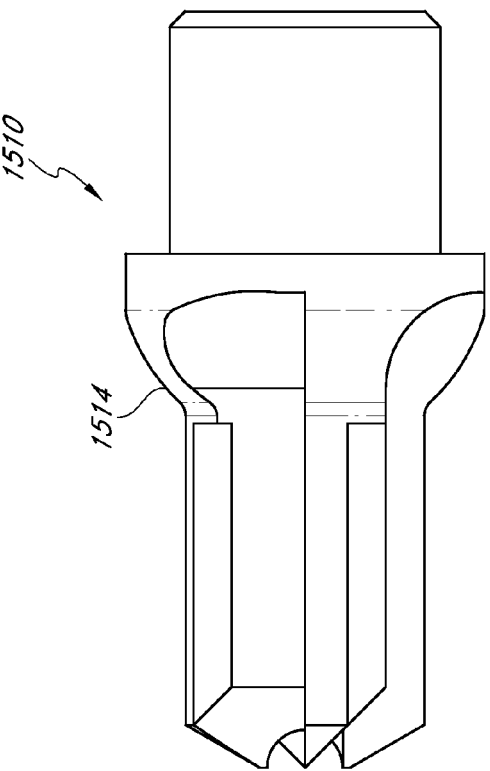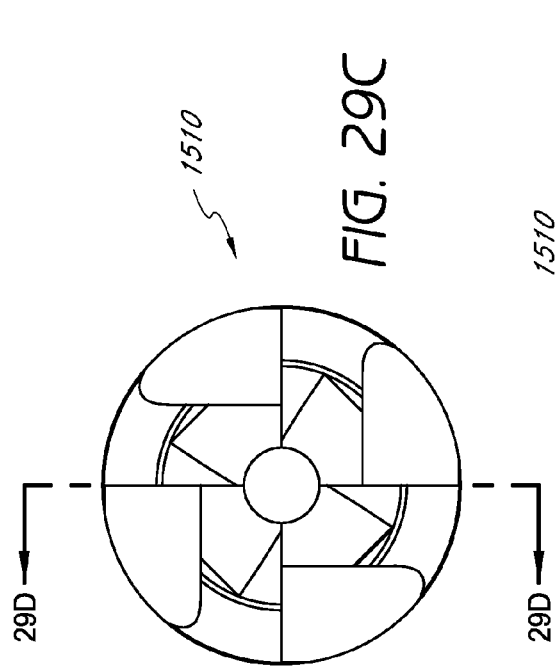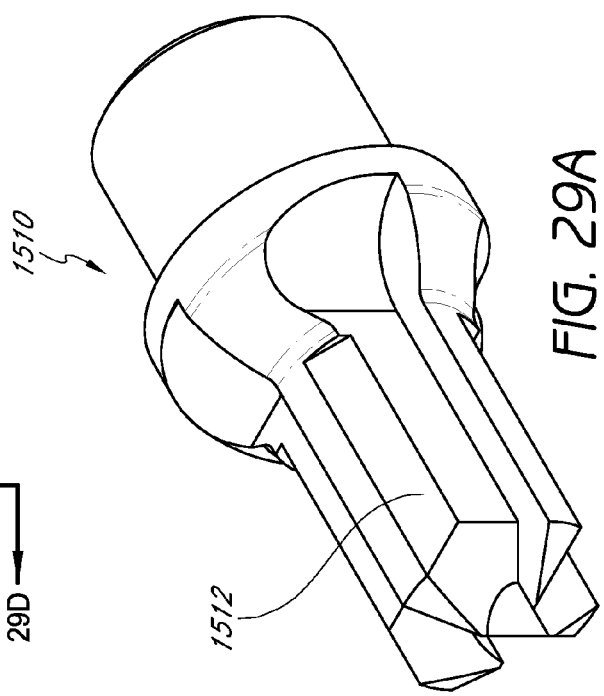

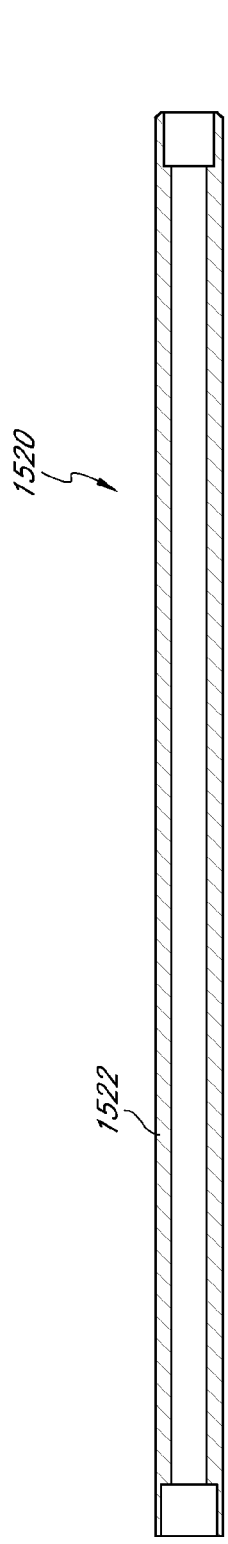
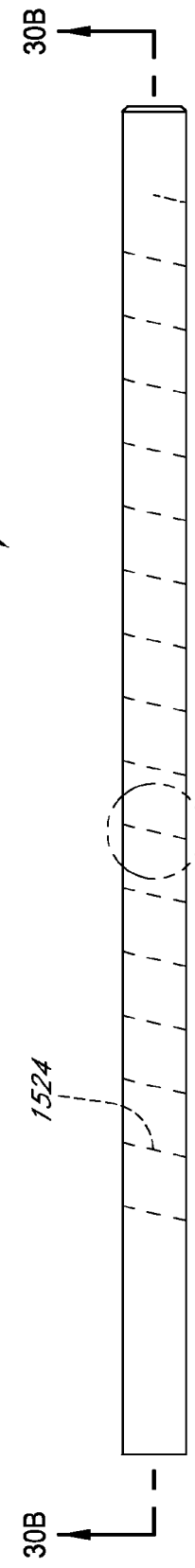
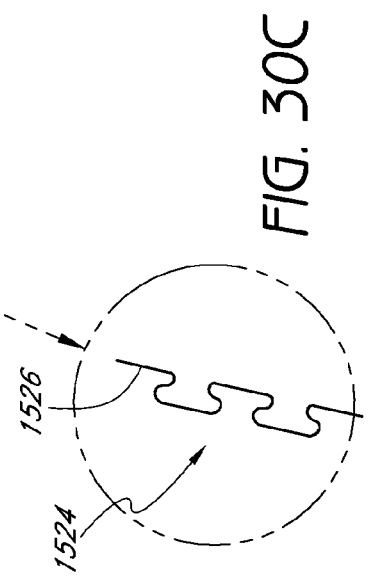
FIG. 30A
FIG. 30B
FIG. 30C

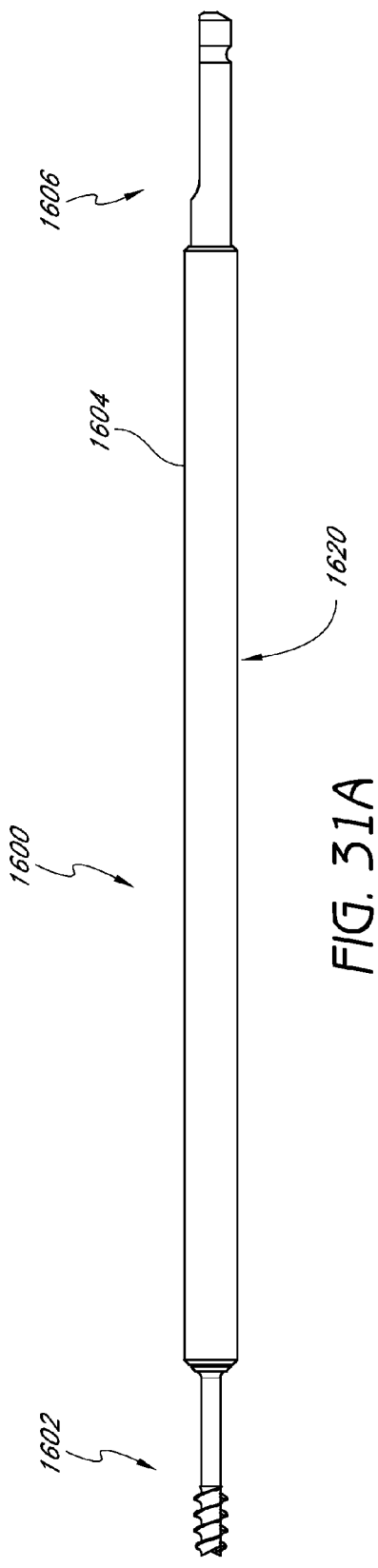
FIG. 31A
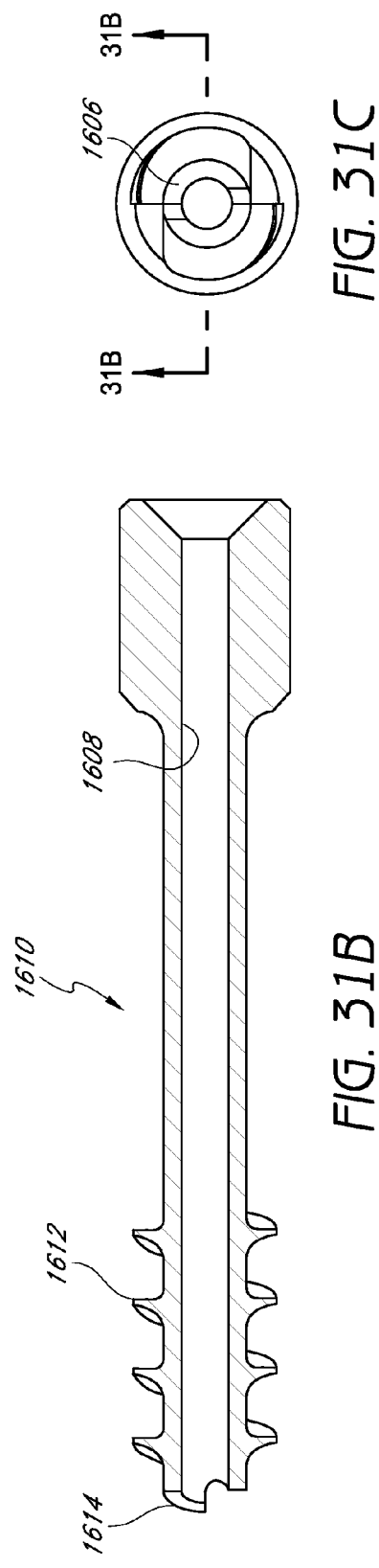
FIG. 31C
FIG. 31B

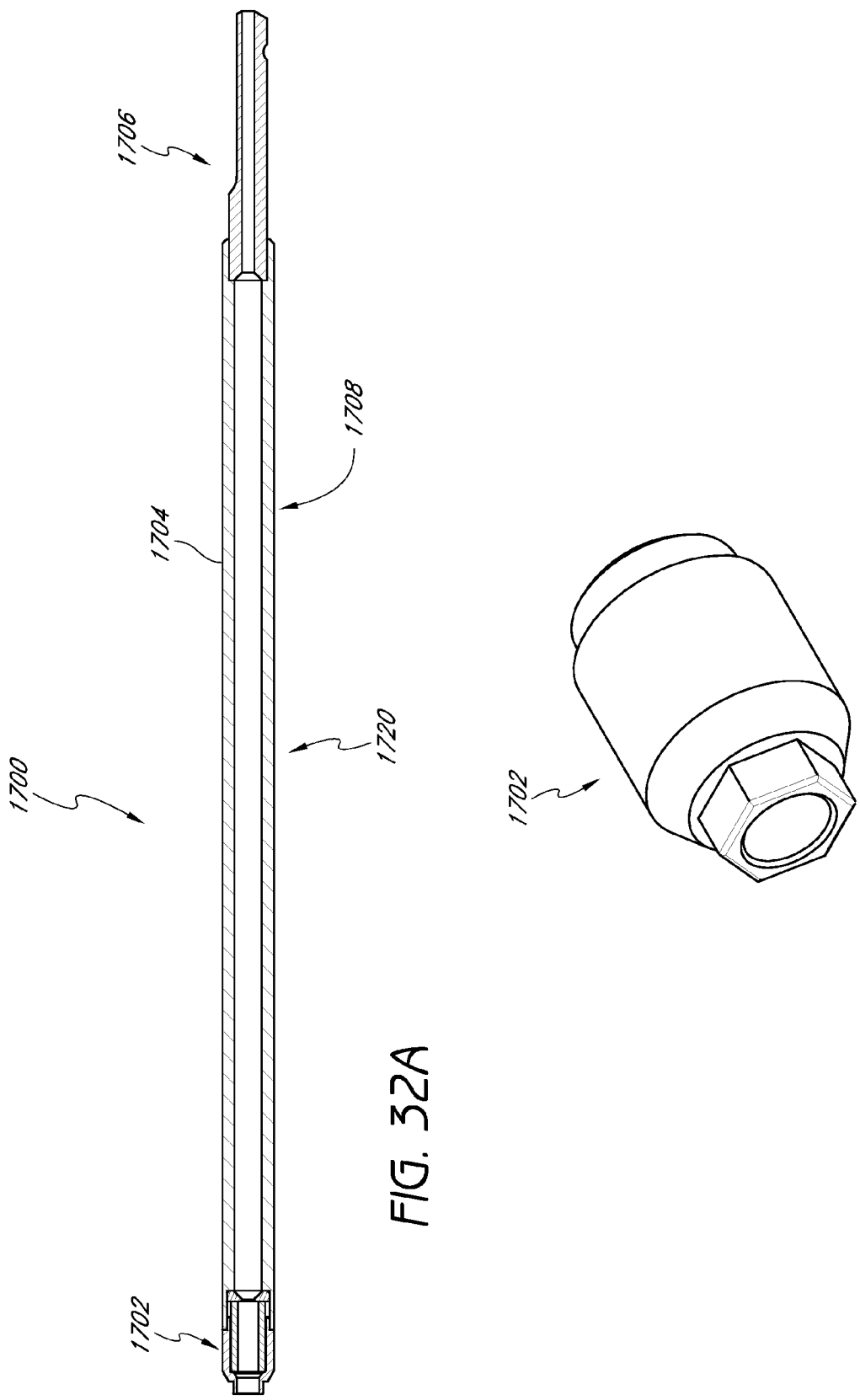

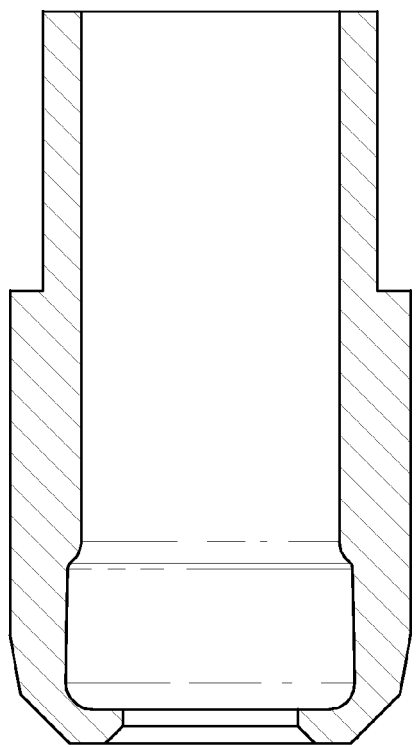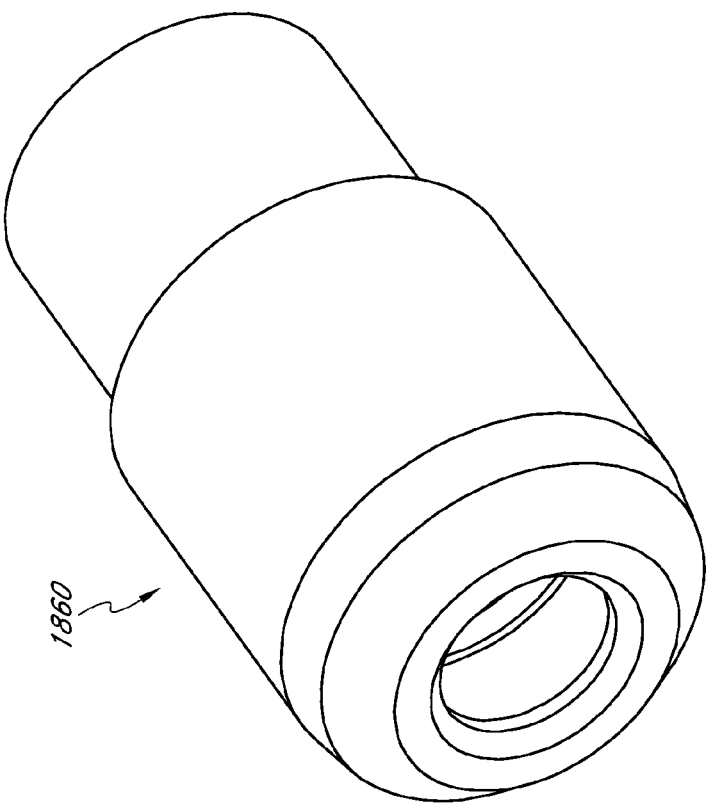
FIG. 33C
FIG. 33B

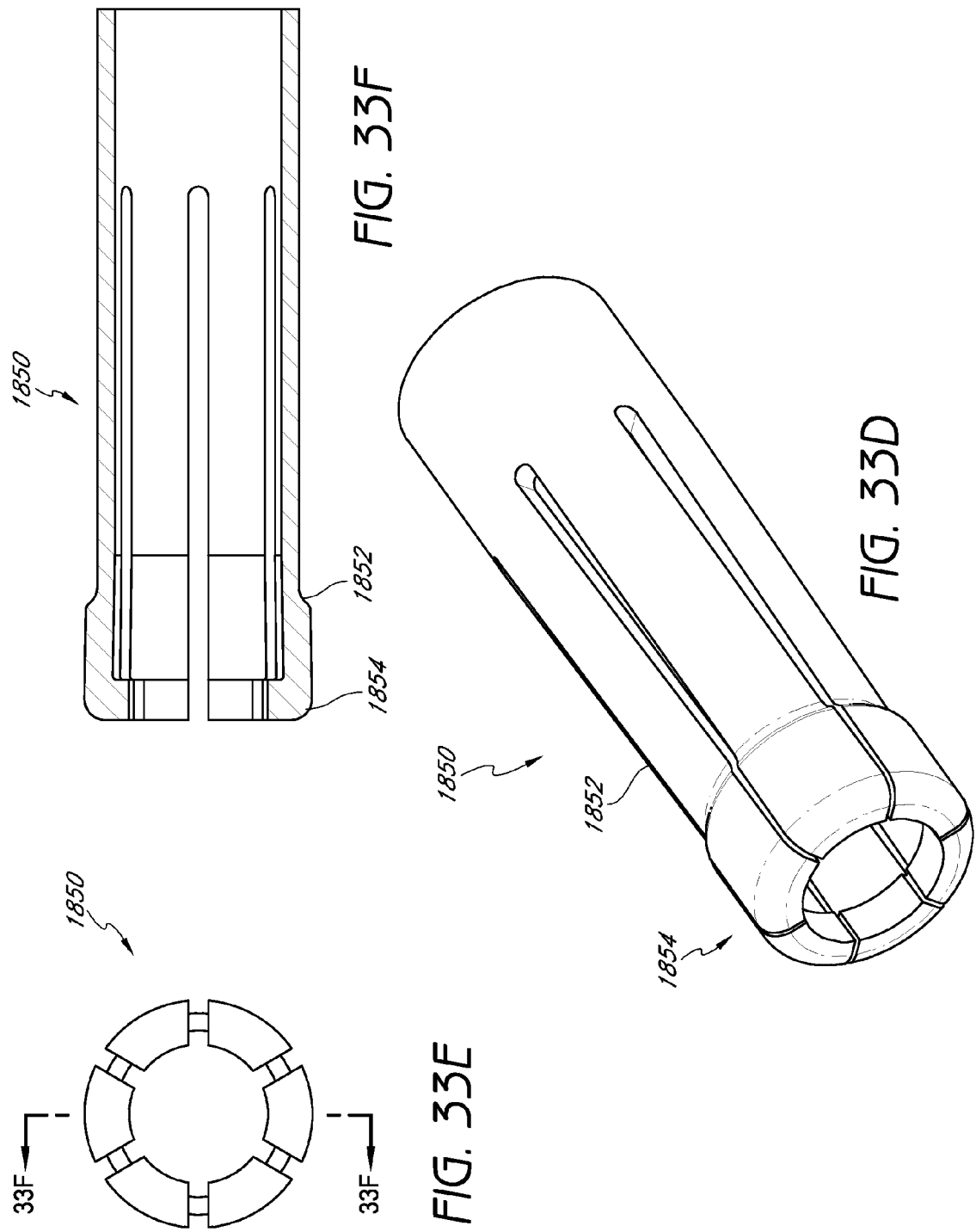

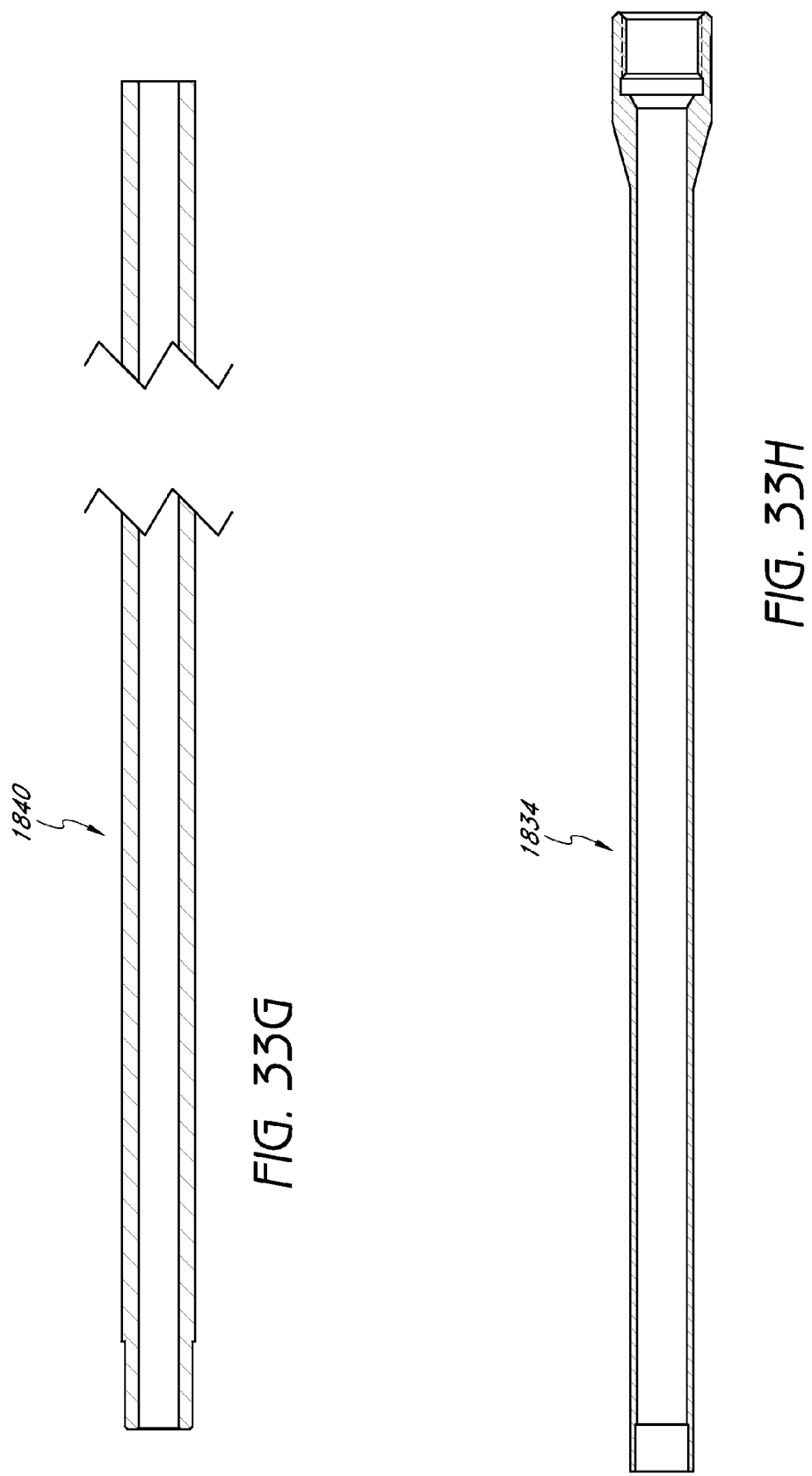

METHOD AND APPARATUS FOR SPINAL FIXATION

CROSS-REFERENCE TO RELATED APPLICATIONS

The present application is a continuation of U.S. patent application Ser. No. 11/738,371, filed Apr. 20, 2007, which claims priority under 35 U.S.C. §119(e) to U.S. Provisional Patent Application No. 60/800,568, filed May 15, 2006 and U.S. Provisional Patent Application No. 60/794,171, filed Apr. 21, 2006, the disclosures of which are incorporated by reference herein in their entireties.

BACKGROUND OF THE INVENTION

1. Field of the Invention

The present application relates to medical devices and, more particularly, to methods and apparatus for spinal stabilization.

2. Description of the Related Art

The human spine is a flexible weight bearing column formed from a plurality of bones called vertebrae. There are thirty three vertebrae, which can be grouped into five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which form the sacrum and the four coccygeal vertebra which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. The vertebra may be united with various types of fixation systems. These fixation systems may include a variety of longitudinal elements such as rods or plates that span two or more vertebrae and are affixed to the vertebrae by various fixation elements such as wires, staples, and screws (often inserted through the pedicles of the vertebrae). These systems may be affixed to either the posterior or the anterior side of the spine. In other applications, one or more bone screws may be inserted through adjacent vertebrae to provide stabilization.

U.S. Patent Publication 2004/0127906 (U.S. patent application Ser. No. 10/623,193, filed Jul. 18, 2003) entitled "METHOD AND APPARATUS FOR SPINAL FUSION" describes a bone fixation screw and technique used to secure two adjacent vertebra to each other in trans-laminar, trans-facet or facet-pedicle (e.g., the Boucher technique) applications. This publication is incorporated herein by reference in its entirety. For example, in a trans-facet application, the fixation device extends through a facet of a first vertebra and into the facet of a second, typically inferior, vertebra. In a trans-laminar application, screws, the fixation device, extend through the spinous process and facet of a first vertebra and into the facet of a second, typically inferior, vertebra. In a facet-pedicle application (e.g., the Boucher technique), the fixation device extends through the facet of a first vertebra and into the pedicle a second, typically inferior, vertebra. These procedures are typically (but not necessarily) preformed with bilateral symmetry.

Notwithstanding the success of the above described devices and methods, there are certain challenges associated with applying the trans-laminar, trans-facet or facet-pedicle (e.g., the Boucher technique) techniques to the cervical portion of the vertebrae. For example, due to the anatomy of the cervical region and interference due to the back of the head in a trans-facet approach, the fixation device may need to extend along an axis that, when extended, interferes with the back of the patient's head. For example, FIG. 1 illustrates a portion of the cervical region and a cannulated access device, which extends over the desired entry axis of the fixation device (not shown). As shown, the back of the patient's spine can interfere with the insertion of the fixation device and the various tools needed to insert the fixation device.

SUMMARY OF THE INVENTION

In some embodiments, a device used for deploying a spinal fixation device comprises an elongated cannulated member and a handle. The elongated cannulated member has a proximal end, a distal end, a first longitudinal axis extending therebetween, and an outer surface. The cannulated member comprises an elongated opening on the outer surface. The handle extends along a second longitudinal axis. The first and second longitudinal axis form an angle with respect to each other. The elongated opening is configured to receive an elongate tubular member having a third longitudinal axis when the third longitudinal axis is oriented transversely to the first longitudinal axis.

In various embodiments, a wire introducer for creating a tissue track for a guidewire, comprises an elongated cannulated member, a handle, and a trocar. The elongated cannulated member has a first longitudinal axis, a distal end and a proximal end, the distal end including at least one cutting element. The handle extends along a second longitudinal axis, wherein the first and second longitudinal axes form an angle with respect to each other. The trocar has a distal end with a sharpened tip and a proximal end configured to receive a strike pin. The trocar is positioned within the cannulated member such that the distal end and proximal end extend beyond the elongated cannulated member.

In some embodiments, a system for coupling a first superior vertebra of a cervical spine to a second inferior vertebra comprises a fixation device and an elongated tubular device. The fixation device has a distal end and a proximal end. The distal end of the fixation device is configured to extend between the first superior vertebra and the second inferior vertebra. The elongated tubular device is configured to apply the fixation device. The tubular device has a first longitudinal axis and a handle extending along a second longitudinal axis. The first and second longitudinal axes form an angle with respect to each other such that when the elongated tubular device is applied to the cervical spine from a direction above the cervical spine, the fixation device can be applied without interference from the head of the patient.

In some embodiments, a system for establishing access for a fixation device configured to extend between a first superior vertebra of a cervical spine to a second inferior vertebra comprises an elongated tubular device and an elongated flexible member. The elongated tubular device has a first longitudinal axis and a handle extending along a second longitudinal axis, the first and second longitudinal axis form an angle with respect to each other. The elongated flexible member has a distal end and a proximal end. The distal end of the device is coupled to a tool, and the proximal end of the device is coupled to a handle.

In some embodiments, a device used for deploying a spinal fixation device comprises an elongated flexible transmission member, a tool, and a handle. The elongated flexible transmission member has a distal end and a proximal end. The tool is coupled to the distal end of the transmission member. The handle is coupled to the proximal end of the transmission member.

In some embodiments, a method of providing spinal fixation in a cervical spine comprises advancing a distal end of an elongated cannulated member, removing the trocar, advancing a first guidewire, removing the first guidewire, advancing a second guidewire, removing the elongated cannulated member, advancing a fascia cutter over the second guidewire, cutting the patient's fascia, removing the fascia cutter, advancing a dilation device, and inserting a distal end of a fixation device. The distal end of the elongated cannula member is advanced with a trocar positioned therein to a first, superior vertebra in the cervical spine to establish a tissue tract. The trocar is removed from the elongated cannulated member. The first guidewire is advanced though the elongated cannulated member and at least partially into the first vertebra. The first guidewire is removed from the elongated cannulated member. The second guidewire is advanced through the elongated cannulated member. The patient's fascia is cut with the fascia cutter. The dilation device is advanced over the second guidewire. The distal end of the fixation device is inserted through the dilation device and through the first vertebra and into the second vertebra.

In some embodiments, a device used for deploying a spinal fixation device comprises an elongated cannulated member and a handle. The elongated cannulated member has a first longitudinal axis. The handle extends away from the elongated cannulated member along second longitudinal axis. The handle includes a gripping portion.

In some embodiments, a method of placing a guidewire near a cervical portion of the spine comprises advancing an elongated member along a first longitudinal axis extending from the cervical portion of the spine toward the head of the patient while grasping a handle coupled to the elongated member and located angularly offset from the elongated member; and inserting a guidewire through the elongated member.

In some embodiments, a method of inserting a fixation device through a first superior vertebra and into a second inferior vertebra in a cervical portion of the spine comprises advancing a fixation device, advancing the bone anchor of the fixation device, preoximally retracting the body of the fixation device, advancing a second fixation device, advancing the bone anchor of the second fixation device, advancing a second proximal anchor, and retracting the body of the second fixation device. A fixation device that comprises a body having a first portion that forms a first bone anchor and a second portion that forms a proximal end through a cannulated member and through a portion of the first cervical vertebra is advanced. The bone anchor of the fixation device is advanced into the second cervical vertebra. The proximal anchor is advanced distally along the fixation device. The body of the fixation device is retracted proximally with respect to the proximal anchor to adjust compression across the first and second cervical vertebra. with substantially bilateral symmetry, a second fixation device is advanced that comprises a body having a first portion that forms a second bone anchor and a second portion that forms a proximal end through a second cannulated member and through a portion of the first vertebra. The bone anchor of the second fixation device is advanced into the second vertebra. The second proximal anchor is advanced distally along the second fixation device. The body of the second fixation device is retracted proximally with respect to the proximal anchor to adjust compression across the first and second vertebrae.

In some embodiments, a fascia cutter for cutting fascia surrounding a portion of the spine comprises an elongated body and a plurality of cutting elements. The elongated body has a proximal end, a distal end and a lumen extending therethrough. The lumen has a distal opening at the distal end and a proximal opening at the proximal end. The plurality of cutting elements is positioned on the distal end of the elongated body. Each of the plurality of cutting elements defines a cutting edge that extends generally radially from the distal end of the lumen.

In some embodiments, a method of providing access to a portion of a spine, comprises advancing a guidewire and advancing a fascia cutter. The guidewire is advanced posteriorly through a patient's tissue to a first vertebra. The fascia cutter comprises at least one sharpened element and is advanced over the guidewire and towards the first vertebra to cut the patient's fascia.

In some embodiments, a method of coupling a first superior vertebra to a second inferior vertebra, comprises advancing a first guidewire, removing the first guidewire, and advancing a second guidewire. The first guidewire is advanced with a generally sharpened distal tip into the first vertebra and into the second vertebra along a first insertion axis. The second guidewire with a generally blunt distal tip is advanced along the first insertion axis into the second vertebra and through a hole created by the first guidewire.

BRIEF DESCRIPTION OF THE DRAWINGS

FIG. 3A is a side perspective view of an embodiment of the fixation device of FIGS. 1 and 2.

FIG. 3B is a side view of the fixation device of FIG. 3A

FIG. 3C is a cross-sectional view taken through line 3C-3C of FIG. 3B.

FIG. 4B is a side view of a proximal anchor of the fixation device of FIG. 3A.

FIG. 4C is a side view of a proximal anchor of the fixation device of FIG. 3A.

FIG. 4D is a front view of a proximal anchor of the fixation device of FIG. 3A.

FIG. 4E is a rear view of a proximal anchor of the fixation device of FIG. 3A.

FIG. 21A is a side view of a cannula portion of the wire introducer of FIG. 8.

FIG. 21B is a cross-sectional view of a cannula portion of the wire introducer of FIG. 8.

FIG. 21C is a front view of a cannula portion of the wire introducer of FIG. 8.

FIG. 21D is a side view of a proximal end of a cannula portion of the wire introducer of FIG. 8.

FIG. 21E is a side view of a distal end of a cannula portion of the wire introducer of FIG. 8.

FIG. 21F is a rear view of a cannula portion of the wire introducer of FIG. 8.

FIG. 22A is a side view of a trocar of the wire introducer of FIG. 8.

FIG. 22B is a side perspective view of a trocar connecting hub of the wire introducer of FIG. 8.

FIG. 22C is a cross-sectional view of a trocar connecting hub of the wire introducer of FIG. 8.

FIG. 22D is a side view of a trocar of the wire introducer of FIG. 8.

FIG. 23A is a perspective view of the strike pin of FIG. 9.

FIG. 23B is a side view of the strike pin of FIG. 9

FIG. 23C is an enlarged view of a portion of the strike pin of FIG. 9.

FIG. 24A is a side view of the sharp guidewire of FIG. 10

FIG. 24B is an enlarged view of a portion of the sharp guidewire of FIG. 10.

FIG. 25 is a side view of the blunt guidewire of FIG. 11.

FIG. 26A is a perspective view of the fascia cutter of FIG. 13.

FIG. 26B is a side view of the fascia cutter of FIG. 13.

FIG. 26C is a front view of the fascia cutter of FIG. 13.

FIG. 26D is a cross-sectional view of the fascia cutter of FIG. 13.

FIG. 27A is a side view of a second dilator tube of the sheath assembly of FIG. 14.

FIG. 27B is a perspective view of the second dilator tube of FIG. 27A.

FIG. 27C is a side view of a first dilator tube of the sheath assembly of FIG. 14.

FIG. 27D is a top vie view of the first dilator tube of FIG. 27C.

FIG. 27E is a perspective view of the sheath assembly of FIG. 14 from a first viewing angle.

FIG. 27H is a perspective view of a first dilator tube of the sheath assembly of FIG. 27G.

FIG. 27I is a perspective view of a second dilator tube of the sheath assembly of FIG. 27G.

FIG. 29A is a perspective view of a drilling element of the drill of FIG. 28.

FIG. 29B is a side view of a drilling element of the drill of FIG. 28

FIG. 29C is a front view of a drilling element of the drill of FIG. 28

FIG. 29D is a cross-sectional view of a drilling element of the drill of FIG. 28

FIG. 30A is a side view of a transmission member of the drill of FIG. 28.

FIG. 30B is a cross-sectional view of a transmission member of the drill of FIG. 28.

FIG. 30C is an enlarged view of an embodiment of cut pattern of the transmission member of the drill of FIG. 28.

FIG. 31A is a side view of the tapping device of FIG. 17.

FIG. 31B is a cross-sectional view of the tapping element of the tapping device of FIG. 17.

FIG. 31C is a front view of the tapping device of FIG. 17.

FIG. 32A is a cross-sectional view of the driving device of FIG. 18

FIG. 32B is a perspective view of the driving element of the driving device of FIG. 18

FIG. 33B is a perspective view of a distal cap of the compression device of FIG. 19.

FIG. 33C is a cross sectional view of the distal cap of FIG. 33B.

FIG. 33D is a perspective view of a collet of the compression device of FIG. 19.

FIG. 33E is a front view of the collet of FIG. 33D.

FIG. 33F is a cross-sectional view of the collet of FIG. 33D.

FIG. 33G is a cross-sectional view of a portion of the compression device of FIG. 19.

FIG. 33H is a cross-sectional view of a traction member of the compression device of FIG. 19.

DETAILED DESCRIPTION OF THE PREFERRED EMBODIMENTS

Figure 1:
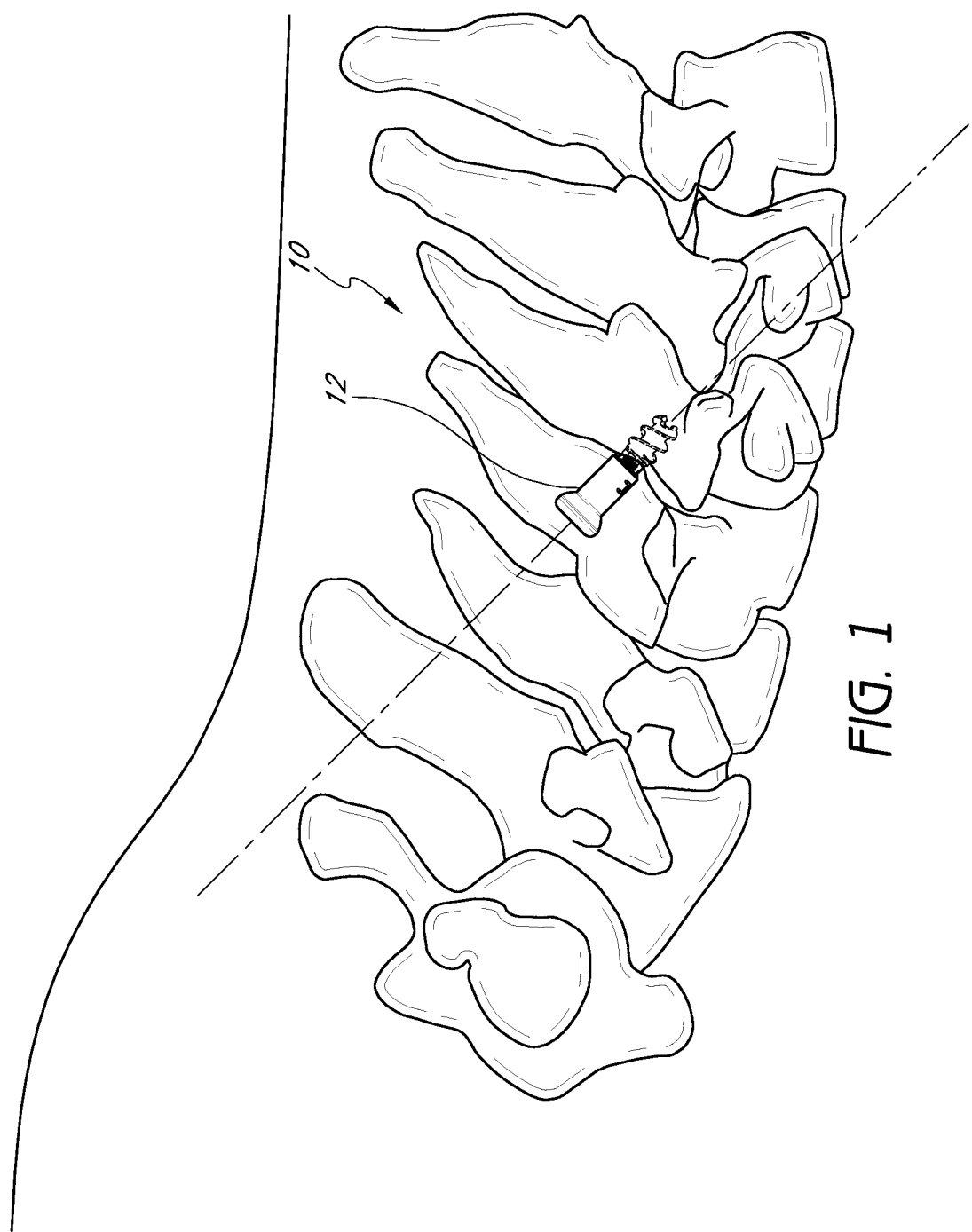
FIG. 1 is a side elevational view of a cervical spine having a fixation device extending across facets of two adjacent vertebrae.
Figure 2:
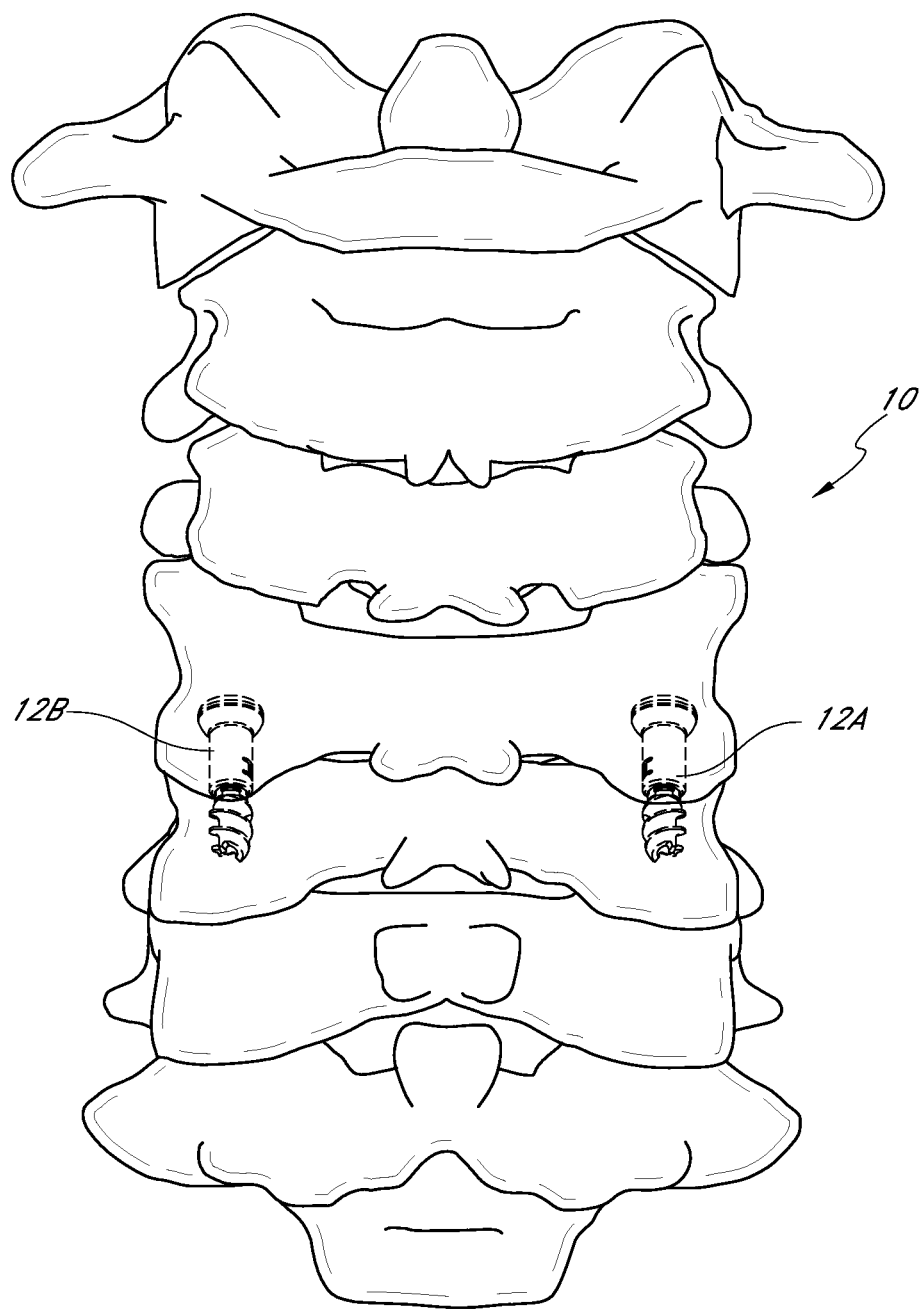
FIG. 2 is a posterior view of the cervical spine of FIG. 1.

Referring to FIG. 1, a side elevational view of an exemplary embodiment of the cervical portion of the spine 10 with a fixation device 12 that extends across the facet joint of two adjacent vertebrae (i.e., a trans-facet application) is illustrated. With reference to FIG. 2, a pair of bone fixation devices 12A, 12B can preferably (but not necessarily) be used with substantial bilateral symmetry to secure two adjacent vertebra to each other (In FIGS. 1 and 2 the bone fixation device is highlighted such that the portions hidden by the vertebrae can be seen). In this manner, the adjacent vertebrae of the spine are united together ("fused") so that motion no longer occurs between the vertebrae. Thus, even in the absence of a stabilizing bar tying pedicle screws to adjacent vertebrae, the fixation devices 12A, 12B can be used to stabilize two vertebrae to each other pending the healing of a fusion. See also U.S. Patent Publication No. 2004/0127905, filed Jul. 18, 2003, application Ser. No. 10/623,193, which is hereby incorporated by reference herein in its entirety.

The disclosure herein will focus on this method of fusing two adjacent vertebrae together described above. However, it should be appreciated that certain aspects of the devices and methods described herein can find applications in other systems for stabilizing and/or fixating the spine. For example, such fixation systems may include a variety of longitudinal elements such as rods or plates that span two or more vertebrae and are affixed to the vertebrae by various fixation elements such as wires, staples, and screws (often inserted through the pedicles of the vertebrae). These systems may be affixed to either the posterior or the anterior side of the spine. Certain aspects and features of the devices and methods disclosed herein can also find utility when stabilizing/fixing other areas of the spine (e.g., lumbar spine).

FIGS. 3A-D illustrate an embodiment of a bone fixation device 212 that can be used as described above. In this embodiment, the device 212 comprises a body 228, a proximal anchor 700 and an optional flange 250. As will be apparent from the description below, the illustrated bone fixation device 212 is particularly advantageous for spinal fixation. For example, the flange 250 can rotate and/or pivot with respect to the proximal anchor 700. In this manner, the bone contacting surface can be positioned more closely to the outer surface of the vertebra. This positioning can result in more bone contacting surface being utilized and the stress supported by the fixation device is spread out over a larger area of the vertebra. However, it should be appreciated that, as mentioned above, the flange 250 can be omitted from certain embodiments of the fixation device. 212.

Another advantage of the illustrated embodiment is that the proximal anchor 700 can be advanced distally over the body 228 while proximal movement of the proximal anchor 700 over the body 228 is resisted. This arrangement allows the clinician to adjust the size (e.g., length) and/or compression force during the procedure without adjusting the position of a distal anchor 234 at the distal end 232 of the body 228. In this manner, the clinician can focus on positioning the distal anchor 234 sufficiently within the vertebra to avoid or reduce the potential for distal migration out of the vertebra, which may damage the particularly delicate tissue, blood vessels, nerves and/or spinal cord surrounding or within the spinal column.

In other embodiments, the proximal anchor 700 can be fixed, coupled and/or integrally formed with the body 228 (e.g., a fixation device in the form of traditional screw or pedicle screw). Various embodiments and/or additional or alternative components of the device 212 can be found in U.S. Patent Publication 2004/0127906 (U.S. patent application Ser. No. 10/623,193, filed Jul. 18, 2003) entitled "METHOD AND APPARATUS FOR SPINAL FUSION", which is hereby incorporated by reference. Additional embodiments and/or alternative components of the device 212 can be found in U.S. Pat. Nos. 6,951,561, 6,942,668, 6,908,465, and 6,890,333, which are also incorporated by reference.

With reference now to FIGS. 3A-D, the device 212 comprises the body 228 that extends between a proximal end 230 and the distal end 232. The length, diameter and construction materials of the body 228 can be varied, depending upon the intended clinical application. In embodiments optimized for spinal stabilization in the cervical spine 10 (FIGS. 1-2) in an adult human population, the body 228 will generally be within the range of from about 10-20 mm in length and within the range of from about 2.5-4 mm in maximum diameter. The length of the helical distal anchor 234, discussed below, may be about 3-15 millimeters. Of course, it is understood that these dimensions are illustrative and that they may be varied as required for a particular patient or procedure.

In one embodiment, the body 228 comprises titanium. However, as will be described in more detail below, other metals, or bioabsorbable or nonabsorbable polymeric materials may be utilized, depending upon the dimensions and desired structural integrity of the finished stabilization device 12 (FIG. 1).

The distal end 232 of the body 228 is provided with the cancellous bone anchor and/or distal cortical bone anchor 234. Generally, for spinal stabilization, the distal bone anchor 234 is adapted to be rotationally inserted into and through a portion (e.g., the facet) of a first, superior, vertebra and then into a portion (e.g., a facet) of a second, inferior vertebra. In the illustrated embodiment, the distal anchor 234 comprises a helical locking structure 272 for engaging cancellous and/or distal cortical bone. In the illustrated embodiment, the locking structure 272 comprises a flange that is wrapped around a central core, which in the illustrated embodiment is generally cylindrical in shape. The flange 272 extends through at least one and generally from about two to about 50 or more full revolutions depending upon the axial length of the distal anchor 234 and intended application. The flange will generally complete from about 2 to about 60 revolutions. The helical flange 272 is preferably provided with a pitch and an axial spacing to optimize the retention force within cancellous bone. While the helical locking structure 272 is generally preferred for the distal anchor, it should be appreciated that in modified embodiments other types of anchors could be used to secure the device in the cancellous bone anchor and/or distal cortical bone, such as, for example, various combinations and sub-combinations of hooks, prongs, expandable flanges, etc.

The helical flange 272 of the illustrated embodiment has a generally triangular cross-sectional shape. However, it should be appreciated that the helical flange 272 can have any of a variety of cross sectional shapes, such as rectangular, oval or other as deemed desirable for a particular application through routine experimentation in view of the disclosure herein. For example, in one modified embodiment, the flange 272 has a triangular cross-sectional shape with a blunted or square apex. Particularly advantageous cross-sectional shapes of the flange are the blunted or square type shapes. Such shapes can reduce cutting into the bone as the proximal end of the device is activated against causing a windshield wiper effect that can loosen the device 212. The outer edge of the helical flange 272 defines an outer boundary. The ratio of the diameter of the outer boundary to the diameter of the central core can be optimized with respect to the desired retention force within the cancellous bone and giving due consideration to the structural integrity and strength of the distal anchor 234. Another aspect of the distal anchor 234 that can be optimized is the shape of the outer boundary and the central core, which in the illustrated embodiment are generally cylindrical.

The distal end 232 and/or the outer edges of the helical flange 272 can be atraumatic (e.g., blunt or soft). This inhibits the tendency of the stabilization device 212 to migrate anatomically distally and potentially out of the vertebrae after implantation. Distal migration is also inhibited by the dimensions and presence of the proximal anchor 700, which will be described in detail below. In the spinal column, distal migration is particularly disadvantageous because the distal anchor 234 may harm the tissue, nerves, blood vessels and/or spinal cord which lie within and/or surround the spine. Such features also reduce the tendency of the distal anchor to cut into the bone during the "window-wiper effect" that is caused by cyclic loading of the device as will be described. In other embodiments, the distal end 232 and/or the outer edges of the helical flange 272 may be sharp and/or configured such that the distal anchor 234 is self tapping and/or self drilling.

A variety of other embodiments for the distal anchor 234 can also be used. For example, the various distal anchors described in U.S. Pat. Nos. 6,887,243 and 6,908,465, which are hereby incorporated by referenced herein. In particular, the distal anchor 234 may comprise a single helical thread surrounding a lumen, much as in a conventional corkscrew. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone. In still other embodiments, the distal anchor 234 may be formed without a helical flange.

As shown in FIG. 3C, the body 228 is preferably cannulated forming a central lumen 242 to accommodate installation over a placement wire as is understood in the art. The cross section of the illustrated central lumen is circular but in other embodiments may be non circular, e.g., hexagonal, to accommodate a corresponding male tool for installation or removal of the body 228 as explained below. In other embodiments, the body 228 may partially or wholly solid.

With continued reference to FIGS. 3A-C, the proximal end 230 of the body 228 can be provided with a coupling 270, for allowing the body 228 to be coupled to an insertion instrument as described below.

Figure 3D:
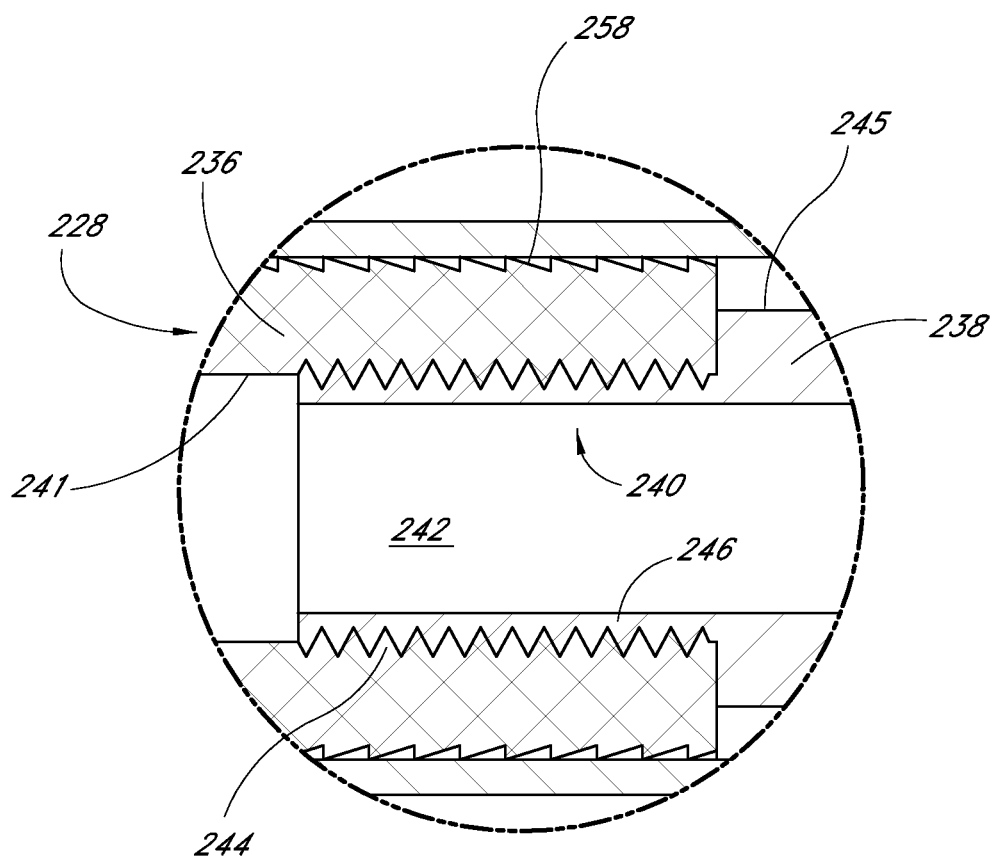
FIG. 3D is an enlarged view of portion labeled 3D in FIG. 3C.
Figure 4A:
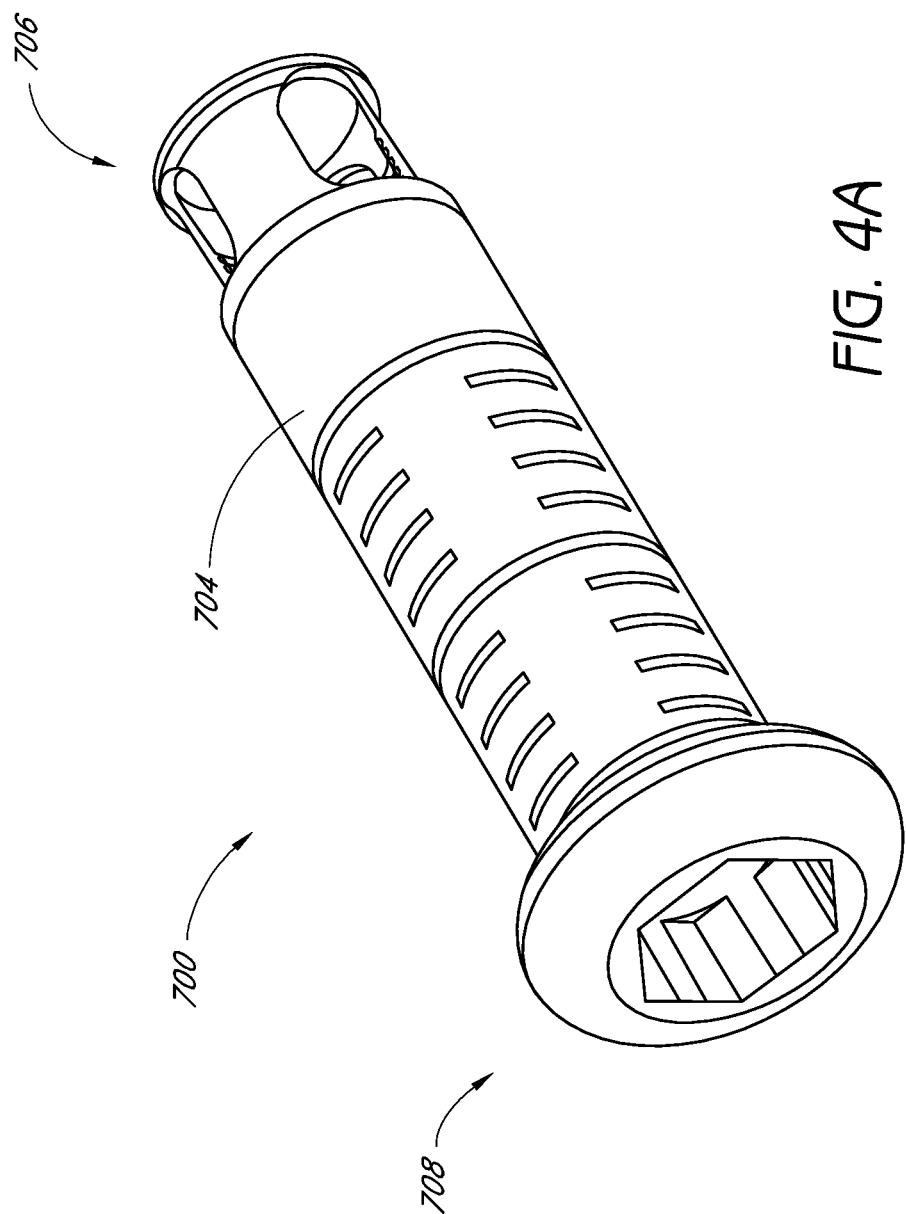
FIG. 4A is a side perspective view of a proximal anchor of the fixation device of FIG. 3A.
Figure 4F:
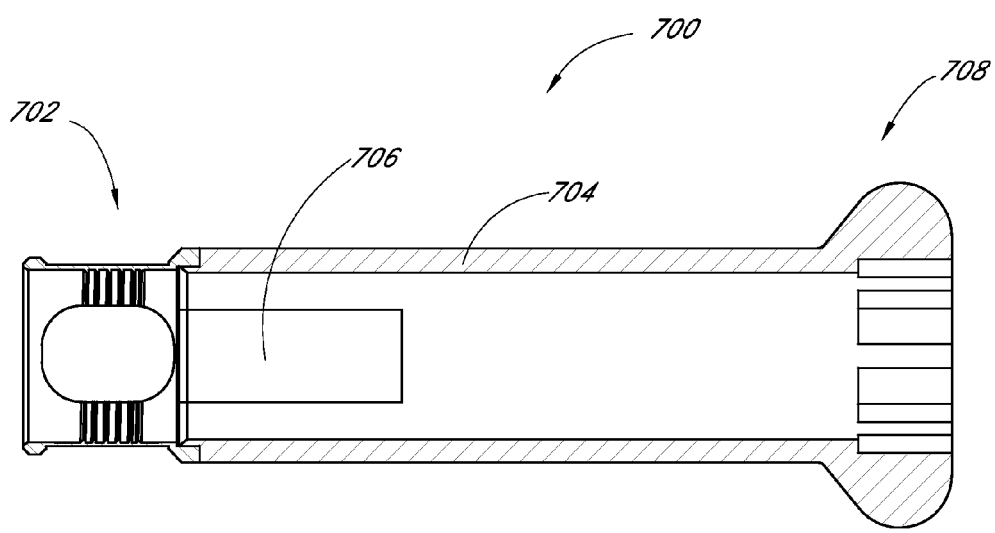
FIG. 4F is a longitudinal cross-sectional view of the proximal anchor of FIG. 4A.

In this embodiment, the body 228 comprises a first portion 236 and a second portion 238 that are coupled together at a junction 240 (FIG. 3D). In the illustrated embodiment, the first portion 236 carries the distal anchor 234 while the second portion 238 forms the proximal end 230 of the body 228. The first and second portions 236, 238 are preferably detachably coupled to each other at the junction 240. In the illustrated embodiment, the first and second portions 236, 238 are detachably coupled to each other via interlocking threads. Specifically, as seen in FIG. 3D, the body 228 can include an inner surface 241, which defines a central lumen 242 that preferably extends from the proximal end 230 to the distal end 232 throughout the body 228. At the proximal end of the first portion 236, the inner surface 241 includes a first threaded portion 244. The first threaded portion 244 is configured to mate with a second threaded portion 246, which is located on the outer surface 245 of the second portion 238. The interlocking annular threads of the first and second threaded portions 244, 246 allow the first and second portions 236, 238 to be detachably coupled to each other. In one modified embodiment, the orientation of the first and second threaded portions 244, 246 can be reversed. That is, the first threaded portion 244 can be located on the outer surface of the first portion 236 and the second threaded portion 246 can be located on the inner surface 241 at the distal end of the second portion 238. Any of a variety of other releasable complementary engagement structures (e.g., bayoneted connections) may also be used, to allow removal of second portion 238 following implantation, as is discussed below.

In a modified arrangement, the second portion 238 can comprise any of a variety of tensioning elements for permitting proximal tension to be placed on the distal anchor 234 while the proximal anchor is advanced distally to compress the fracture. For example, any of a variety of tubes or wires can be removably attached to the first portion 236 and extend proximally to the proximal handpiece. In one such arrangement, the first portion 236 can include a releasable connector in the form of a latching element, such as an eye or hook. The second portion 238 can include a complementary releasable connector (e.g., a complementary hook or eye) for engaging the first portion 236. In this manner, the second portion 238 can be detachably coupled to the first portion 236 such that proximal traction can be applied to the first portion 236 through the second portion as will be explained below. Alternatively, the second portion 238 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

As mentioned above, the proximal end 230 of the fixation device can also be provided with the proximal anchor 700. With reference FIGS. 4A-F, the proximal anchor 700 comprises a housing 704 forming a lumen configured such that the body 228 may extend, at least partially, through the proximal anchor 700. The proximal anchor 700 can be axially distally moveable along the body 228. As will be explained below, complimentary locking structures such as threads, levers, split rings, and/or ratchet like structures between the proximal anchor 700 and the body 228 resist proximal movement of the anchor 700 with respect to the body 228 under normal use conditions. The proximal anchor 700 preferably can be axially advanced along the body 700 with and/or without rotation as will be apparent from the disclosure herein.

With particular reference to FIGS. 3A, 4D, 4E and 4F, the fixation device may include an antirotation lock between the first portion 236 of the body 228 and the proximal anchor 700. In the illustrated embodiment, the first portion 236 includes a pair of flat sides 280, which interact with corresponding flat structures 282 in the proximal anchor 700. One or three or more axially extending flats may also be used. As such, rotation of the proximal anchor 700 is transmitted to the first portion 236 and the distal anchor 234 of the body 228. Of course, those of skill in the art will recognize various other types of splines or other interfit structures can be used to prevent relative rotation of the proximal anchor 700 and the first portion 236 of the body 228. For example, in one embodiment, the first portion 236 may include three flat sides, which interact with corresponding flat structures on the proximal anchor.

To rotate the proximal anchor 700, the flange 708 is preferably provided with a gripping structure to permit an insertion tool to rotate the flange 708. Any of a variety of gripping structures may be provided, such as one or more slots, flats, bores or the like. In one embodiment, the flange 708 is provided with a polygonal, and, in particular, a pentagonal or hexagonal recess 284'. See FIG. 4A.

In this illustrated embodiment, a tubular housing 702 is attached to, coupled to, or integrally formed (partially or wholly) with a secondary tubular housing 704, which includes one or more anti-rotational features 706 (e.g., flat sides) for engaging corresponding anti-rotational features formed on the body as described above. The flange or collar 708 is attached, coupled or integrally formed with the proximal end of the secondary tubular housing. The teeth or flanges 610 on the bridges 606 may also be configured such that the proximal anchor may be distally advanced and/or removed with rotation. (See FIG. 4C). The illustrated embodiment also advantageously includes visual indicia 712 (e.g., marks, grooves, ridges etc.) on the tubular housing 704 for indicating the depth of the proximal anchor 700 within the bone.

As mentioned above, the anchor 700 can include teeth or flanges 610 on the bridges 606 which form surface structures for cooperating with complementary surface structures 258 on the first portion 236 of the body 228 (see FIG. 3C). In the illustrated embodiment, the complimentary surface structures 258 comprise a series of annular ridges or grooves. The surface structures 610 and complementary surface structures 258 permit distal axial travel of the proximal anchor 700 with respect to the body 228, but resist proximal travel of the proximal anchor 700 with respect to the body 228.

For example, when the proximal anchor 700 is urged proximally with respect to the body 228, the flanges or teeth 610 engage the complementary surface structures 258. This engagement prevents proximal movement of the proximal anchor 700 with respect to the body 228. In contrast, when the proximal anchor 700 is moved distally with respect to the body 228, the teeth 610 on the bridges 606 can bend outwardly away from the body 228 so as to allow the proximal anchor 700 to move distally. Of course, those of skill in the art will recognize that there are a variety of other complementary surface structures, which permit one way ratchet-like movement. For example, a plurality of annular rings or helical threads, ramped ratchet structures and the like for cooperating with an opposing ramped structure or pawl can also be used. In one embodiment, opposing screw threads are dimensioned to function as a ratchet.

Retention structures 258 are spaced axially apart along the body 228, between a proximal limit and a distal limit. The axial distance between proximal limit and distal limit is related to the desired axial working range of the proximal anchor 700, and thus can define a range of functional sizes of the fixation device 212. Thus, the fixation device 212 of the exemplary embodiment can provide compression between the distal anchor 234 and the proximal anchor 700 in vertebrae throughout a range of motion following the placement of the distal anchor 234 in a vertebra. That is, the distal anchor 234 may be positioned within the cancellous and/or distal cortical bone of a vertebra, and the proximal anchor 700 may be distally advanced with respect to the distal anchor 234 throughout a range to provide compression without needing to relocate the distal anchor 234 and without needing to initially locate the distal anchor 234 in a precise position with respect to the proximal side of the bone or another vertebra. Providing a working range throughout which tensioning of the proximal anchor 700 is independent from setting the distal anchor 234 allows a single device to be useful for a wide variety of spinal fixation procedures, as well as eliminates the need for accurate device measurement. In addition, this arrangement allows the clinician to adjust the compression force during the procedure without adjusting the position of the distal anchor 234. In this manner, the clinician may focus on positioning the distal anchor 234 sufficiently within the vertebra to avoid or reduce the potential for distal migration out of the vertebra, which may damage the particularly delicate tissue, blood vessels, nerves and/or spinal cord surrounding or within the spinal column.

In many applications, the working range is at least about 10% of the overall length of the fixation device 212, and may be as much as 20% or 50% or more of the overall device length. In the context of a spinal application, working ranges of up to about 10 mm or more may be provided, since estimates within that range can normally be readily accomplished within the clinical setting. The embodiments disclosed herein can be scaled to have a greater or a lesser working range, as will be apparent to those of skill in the art in view of the disclosure herein.

Figure 5A:
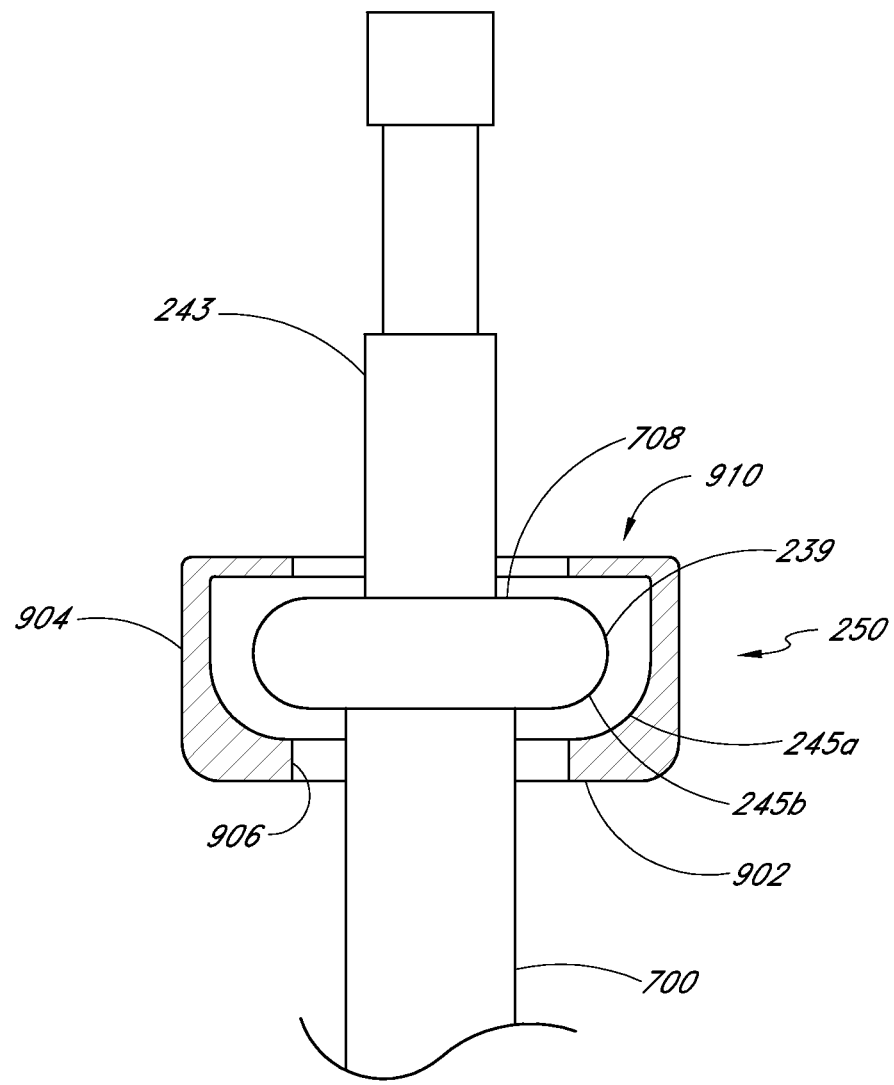
FIG. 5A is a cross-sectional side view of a washer of the fixation device of FIG. 3A.
Figure 5B:
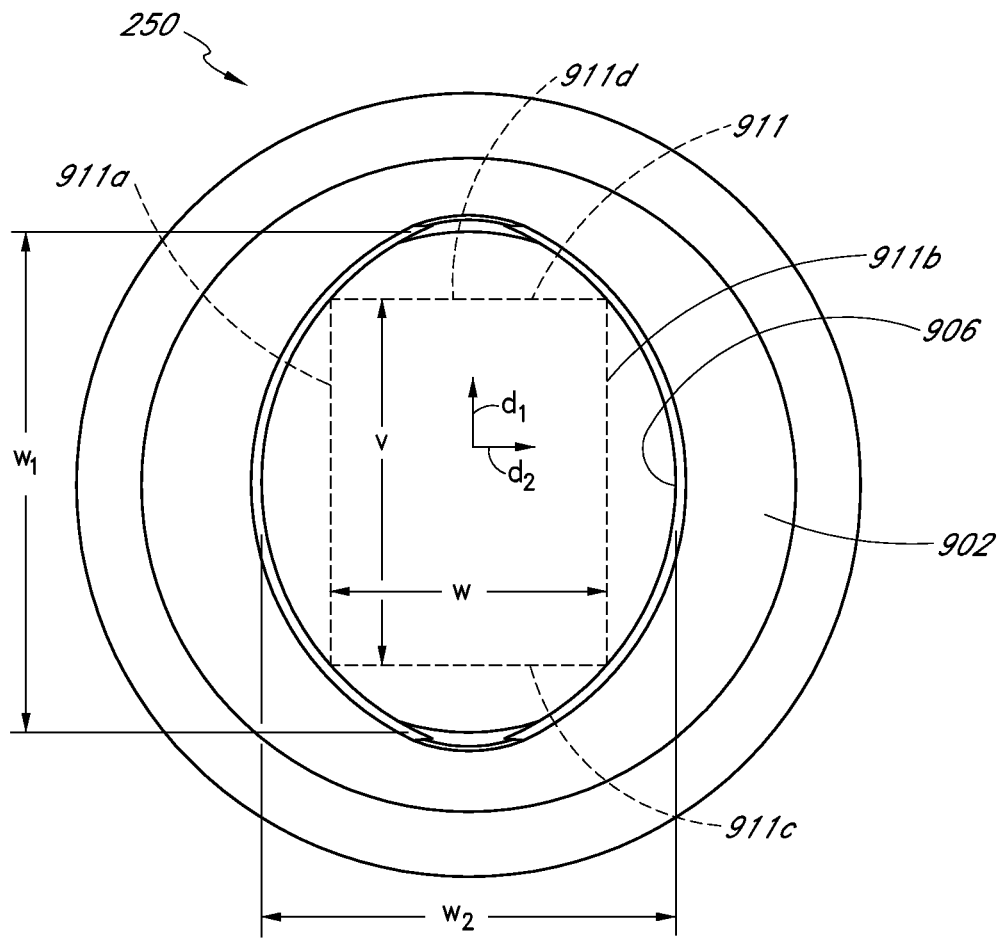
FIG. 5B is a top view of a washer of the fixation device of FIG. 3A.

FIGS. 5A and 5B illustrate a preferred embodiment of a washer 250 that can be used with the spinal fixation device 212. However, as mentioned above, in other embodiments the washer 250 can be omitted. In the illustrated embodiment, the washer 250 is configured to interact with the head 708 of the proximal anchor 700. The washer 250 includes a base 902 and a side wall 904. The base 902 and side wall 904 define a curved, semi-spherical or radiused surface 245a that interacts with the corresponding curved, semi-spherical or radiused surface of the head 708. The surface 245a surrounds an aperture 906 formed in the base 902. As described above, this arrangement allows the housing 702 and/or body 228 to extend through and pivot with respect to the washer 250.

With particular reference to FIG. 5B, in the illustrated embodiment, the aperture 906 is preferably elongated with respect to a first direction d1 as compared a second direction d2, which is generally perpendicular to the first direction d1. In this manner, the width w1 of the aperture in the first direction is greater than the width w2 of the aperture in the second direction. In this manner, the aperture 906 provides a channel 911 with a width w between the sides 911a, 911b defined with respect to the second direction d2 that is preferably greater than the maximum width of the tubular housing of the proximal anchor 700 but smaller than the width of the head 708 such that the proximal anchor 700 can not be pulled through the aperture 906. The height v of the channel is defined between the sides 911c, 911d in the second direction. As such, the elongated aperture 906 permits greater angular movement in a plane containing the first direction d1 as portions of the proximal anchor 700 are allowed rotate into the elongated portions of the aperture 906. The aperture 906 may be elliptical or formed into other shapes, such as, for example, a rectangle or a combination of straight and curved sides.

In some embodiments, the washer 250 includes a portion that is configured so that the proximal end of the anchor 700 is retained, preferably permanently retained, within the washer 250. In the illustrated embodiment, the side walls 904 are provided with lips 910. The lips 910 extend inwardly from the side walls 904 towards the aperture 906 and interact with the proximal end of the head 708 so that the proximal anchor 700 is retained within the washer 250. Preferably, the washer 250 is toleranced to allow the proximal anchor 700 to freely rotate with respect to the washer 250. In this manner, the washer 250 and the proximal anchor 700 can move together for convenient transport.

As described above, when the body 228, the proximal anchor 700 and the washer 250 are deployed into a patient, the washer 250 can inhibit distal movement of the body 228 while permitting at least limited rotation between the body 228 and the washer 250. As such, the illustrated arrangement allows for rotational and angular movement of the washer 250 with respect to the body 228 to accommodate variable anatomical angles of the bone surface. This embodiment is particularly advantageous for spinal fixation and, in particular, trans-laminar, trans-facet and trans-facet-pedicle applications. In such applications, the washer 250 may seat directly against the outer surface of a vertebra. Because the outer surface of the vertebra is typically non-planar and/or the angle of insertion is not perpendicular to the outer surface of the vertebra, a fixed flange may contact only a portion of the outer surface of the vertebra. This may cause the vertebra to crack due to high stress concentrations. In contrast, the angularly adjustable washer 250 can rotate with respect to the body and thereby the bone contacting surface may be positioned more closely to the outer surface. More bone contacting surface is thereby utilized and the stress is spread out over a larger area. In addition, the washer, which has a larger diameter than the body 228, or proximal anchor described herein, effectively increases the shaft to head diameter of the fixation device 212, thereby increasing the size of the loading surface and reducing stress concentrations. Additionally, the washer 250 can be self aligning with the outer surface of the vertebra, which may be curved or non-planer. The washer 250 can slide along the surface of the vertebra and freely rotate about the body 228 until the washer 250 rests snugly against the surface of the vertebra for an increased contact area between the bone and the washer 250. As such, the washer 250 can be conveniently aligned with a curved surface of the vertebra.

In another embodiment, the washer 250 has a surface treatment or bone engagement features that can engage with the surface of the bone to inhibit relative movement between the washer 250 and the bone. Although not illustrated, the washer 250 can include a plurality of bone engagement features in the form of one or more spikes (not shown) extending from the surface of the washer 250. The spikes can contact the surface of the bone to provide additional gripping support, especially when the flange is positioned against, for example, uneven bone surfaces and/or soft tissue. Optionally, the washer 250 can have protuberances, roughened surface, ridges, serrations, or other surface treatment for providing friction between the flange and the surface of the bone. However, it should be appreciated that in modified embodiments the washer 250 may be formed without the bone engagement features or surface treatments. As an independent feature, for example, the washer 250 can be enlarged and includes one or two or more openings for receiving one or set screws (not shown). The setscrews can be passed through the openings to securely fasten the washer 250 to a bone.

FIGS. 6A-D illustrate another embodiment of a proximal anchor 800. In this embodiment, the proximal anchor 800 includes a recess 839 configured to receive a split ring 434' as described below with reference to FIGS. 7A and 7B. As will be explained in detail below, the proximal anchor 800 includes an anti-rotation feature to limit or prevent rotation of a ring 434' within the proximal anchor 800. In light of the disclosure herein, it is contemplated that various different configurations can limit the rotation of the ring 434'. However, a particularly advantageous arrangement will be described below with reference to the illustrated embodiment.

In the illustrated embodiment, the proximal anchor 800 has a generally tubular housing 804 that can engage with a body 228 or a first portion 236 of a body 228 as described above. The tubular housing 804 comprises one or more anti-rotational features 806 such as a plurality of flat sides that are configured to mate corresponding anti-rotational features 280 or flat sides of the body 228 of the fixation device. In the illustrated embodiment, the body 228 has three flat sides 280. Disposed between the flat sides 280 are the portions of the body 228 which include the complementary locking structures such as threads or ratchet like structures as described above. The complementary locking structures interact with the ring 434' as described above to resist proximal movement of the anchor 800 under normal use conditions while permitting distal movement of the anchor 800 over the body 228.

As mentioned above, the ring 434' can be positioned within the recess 839. In the illustrated embodiment, the recess 839 and ring 434' are positioned near to and proximal of the anti-rotational features 806. However, the ring 434' can be located at any suitable position along the tubular housing 804 such that the ring 434' can interact with the retention features of the body 228.

During operation, the ring 434' may rotate to a position such that the gap 431' between the ends 433a', 433b' of the ring 434' lies above the complementary retention structures on the body 228. When the ring 434' is in this position, there is a reduced contact area between the split ring 434' the complementary retention structures thereby reducing the locking strength between the proximal anchor 800 and the body 228. In the illustrated embodiment, for example, the locking strength may be reduced by about ⅓ when the gap 431' is over the complementary retention structures between flat sides 280'. As such, it is advantageous to position the gap 431' on the flat sides 280' of the body 228' that do not include complementary retention structures. See also FIGS. 7A and 7B.

Figure 6A:
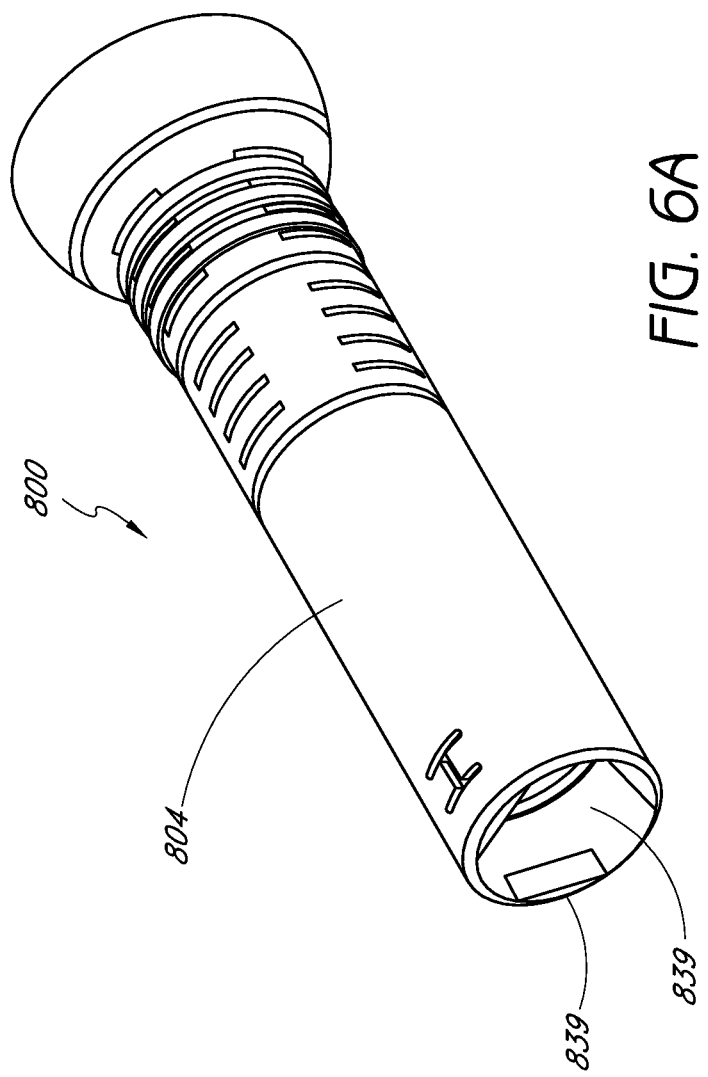
FIG. 6A is a side perspective view of another embodiment of a proximal anchor.
Figure 6C:
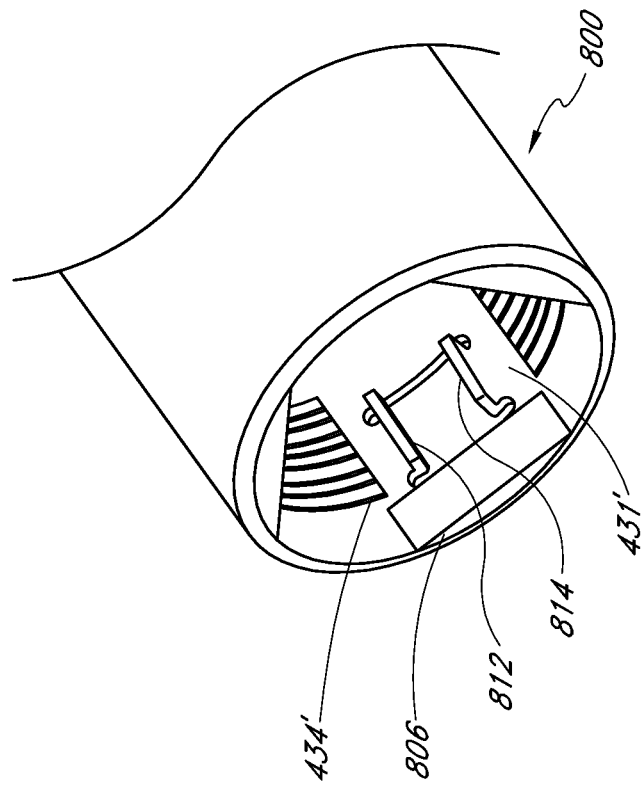
FIG. 6C is a perspective view of a distal end of the proximal anchor of FIG. 6A in a bent configuration.
Figure 6B:
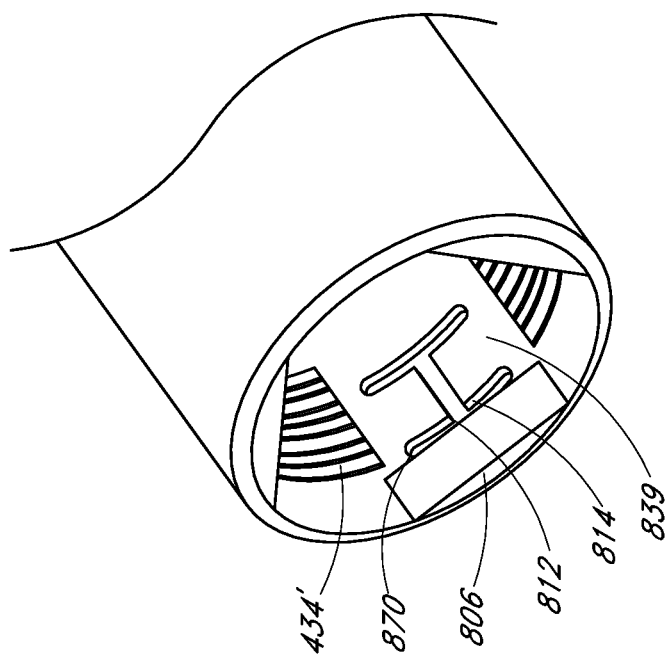
FIG. 6B is a perspective view of a distal end of the proximal anchor of FIG. 6A in an unbent configuration
Figure 7B:
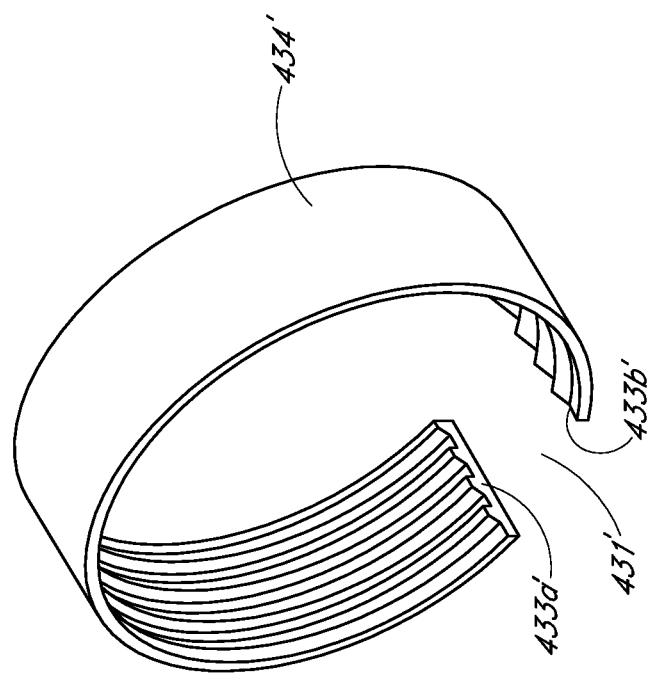
FIG. 7B is a perspective view of an embodiment of a split ring.
Figure 7A:
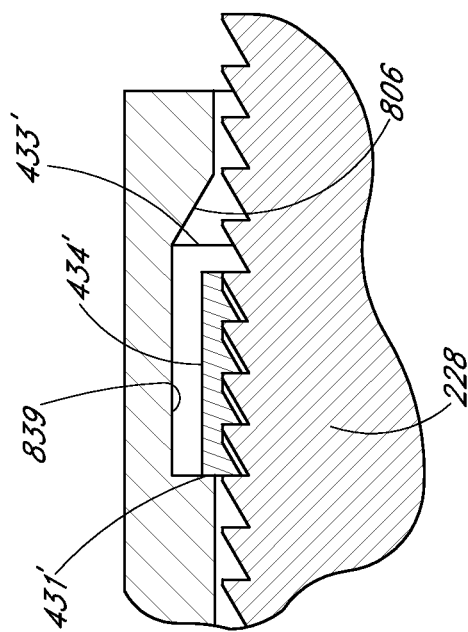
FIG. 7A illustrates a cross-sectional view of an embodiment of split ring

With reference to FIGS. 6B and 6C, to achieve this goal, the illustrated embodiment includes a pair of tabs 812, 814 that extend radially inward from the interior of the proximal anchor 800. The tabs 812, 814 are configured to limit or prevent rotational movement of the ring 434' relative to the housing 804 of the anchor 800. In this manner, the gap 431' of the ring 434' may be positioned over the flattened sides 280 of the body 228.

In the illustrated embodiment, the tabs 812, 814 have a generally rectangular shape and have a generally uniform thickness. However, it is contemplated that the tabs 812, 814 can be square, curved, or any other suitable shape for engaging with the ring 434' as described herein.

Figure 6D:
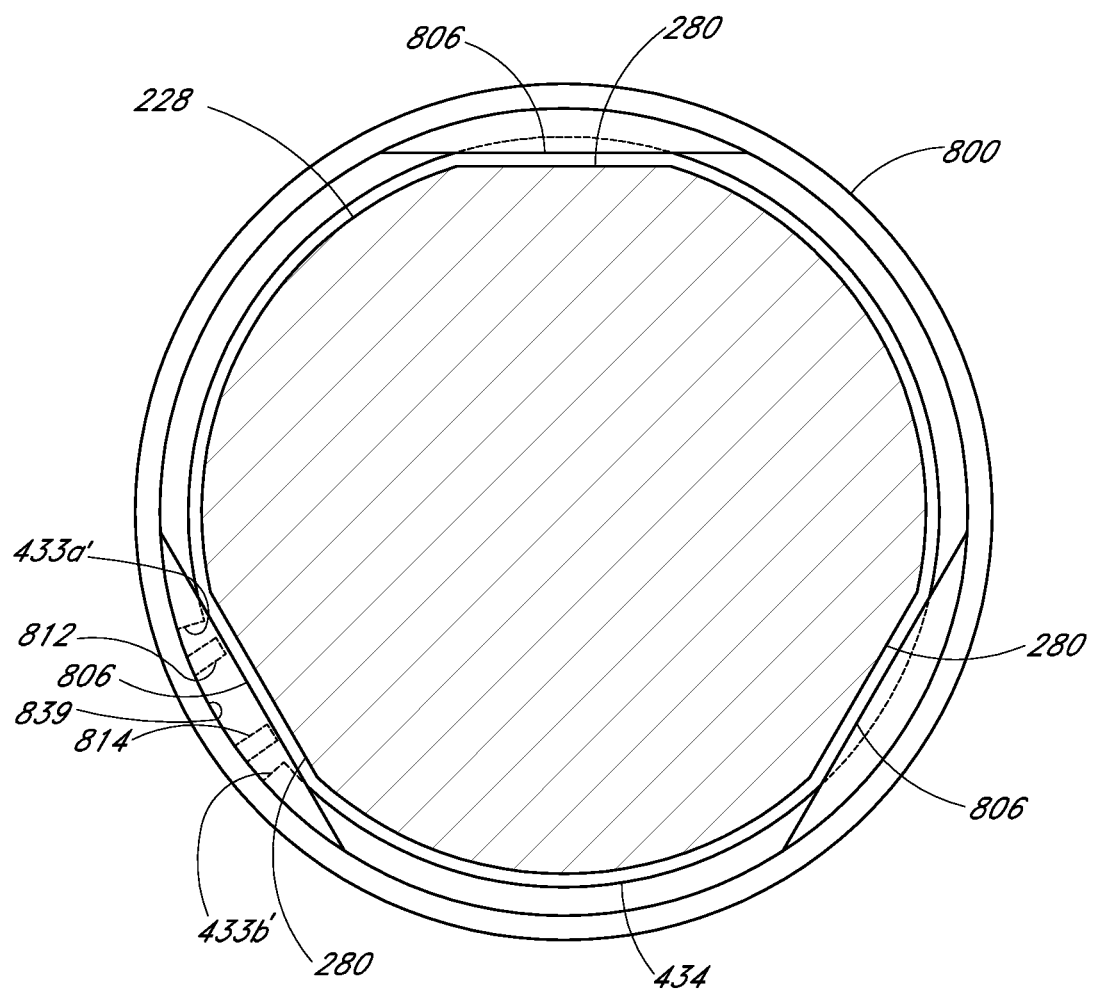
FIG. 6D is a cross-sectional view taken through the distal end of the proximal anchor of FIG. 6A.

In the illustrated embodiment, the tabs 812, 814 are formed by making an H-shaped cut 870 in the tubular housing 804 and bending the tabs 812, 814 inwardly as shown in FIG. 6C. As shown in FIG. 6D, the tabs 812, 814 (illustrated in phantom) are interposed between the edges 433a', 433b' of the ring 434'. The edges 433a', 433b' of the ring 434' can contact the tabs to limit the rotational movement of the ring 434'. It is contemplated that there are many suitable manners for forming the tabs 812, 814. In addition, in other embodiments, the tabs 812, 814 may be replaced by a one or more elements or protrusions attached to or formed on the interior of the proximal anchor 800.

In one embodiment of use and depending upon the spinal fixation technique, the distal ends 232 of one or more bone fixation devices 212 as described herein are advanced into the anterior vertebral body or other suitable portion of one or more vertebrae. As will be explained in more detail below, the fixation device is typically used to couple one vertebra that is unstable, separated or displaced, to another vertebra, which is not unstable, separated or displaced.

The proximal anchor 700, 800 may be carried by the fixation device 212 prior to advancing the body 228 into the vertebrae, or may be attached following placement of the body 228 within the vertebrae. In one embodiment, stabilization implants (e.g., a fixation plate and/or rod) may be placed over or coupled to the body 228 or the proximal anchor 700, 800 before the proximal anchor is placed on the body.

Once the anchor is in the desired location, proximal traction is applied to the proximal end 230 of body 228, such as by conventional hemostats, pliers or a calibrated loading device, while distal force is applied to the proximal anchor 700, 800. In this manner, the proximal anchor 700, 800 is advanced distally with respect to the body 228 until the proximal anchor 700, 800 fits snugly against the outer surface of the vertebra or a fixation plate/rod. Appropriate tensioning of the fixation device 212 is accomplished by tactile feedback or through the use of a calibration device for applying a predetermined load on the implantation device. As explained above, one advantage of the structure of the illustrated embodiments is the ability to adjust compression independently of the setting of the distal anchor 234 within the vertebra. Another advantage of the illustrated embodiment is that an increased compression force can be generated between the two vertebrae as compared to screws without a proximal anchor and/or screws that do not utilize proximal retraction of the body 228 with respect to the proximal anchor 700, 800.

Following appropriate tensioning of the proximal anchor 700, 800, the second portion 238 of the body 228 is preferably detached from the first portion 236 and removed. In other embodiment, this may involve cutting the proximal end of the body 228. For example, the proximal end of the body 228 may be separated by cauterizing.

Following or before removal of the second portion 238 of each body 228, additional fixation devices 212 may be implanted and/or additional stabilization implants (e.g., rods, plates, etc.) may be coupled to the body 228. The access site may be closed and dressed in accordance with conventional wound closure techniques.

In a modified arrangement, the second portion 238 may form part of the driving device, which is used to rotate the proximal anchor 700, 800 and thus cancellous bone anchor 234 into the vertebrae. The second portion 238 is used to apply proximal traction. After appropriate tensioning, the second portion 238 can be de-coupled from the first portion 236 and removed with the driving device.

In the foregoing variation, the second portion 238 may be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 238 while simultaneously distally advancing the proximal anchor. Following appropriate tensioning, the second portion 238 may be disengaged from the implant, and removed from the patient. In the example of a threaded engagement, the second portion 238 may be disengaged from the implant by rotating a thumb wheel or other rotational control on the hand piece. In an alternate embodiment, such as where the second portion 238 comprises a pull wire, following appropriate tensioning across the fracture, a first end of the pull wire is released such that the pull wire may be removed from the implant by proximal retraction of the second end which may be attached to the hand piece.

Preferably, the clinician will have access to an array of fixation devices 212, having, for example, different diameters, axial lengths and, if applicable, angular relationships. These may be packaged one or more per package in sterile or non-sterile envelopes or peelable pouches, or in dispensing cartridges which may each hold a plurality of devices 212. The clinician will assess the dimensions and load requirements, and select a fixation device from the array, which meets the desired specifications.

Methods implanting stabilization devices described above as part of a particularly advantageous spinal fixation procedure will now be described. Although certain aspects and features of the methods and instruments described herein can be utilized in an open surgical procedure, the disclosed methods and instruments are optimized in the context of a percutaneous or minimally invasive approach in which the procedure is done through one or more percutaneous small openings. Thus, the method steps which follow and those disclosed are intended for use in a trans-tissue approach. However, to simplify the illustrations, the soft tissue adjacent the treatment site have not been illustrated in the drawings.

Figure 8:
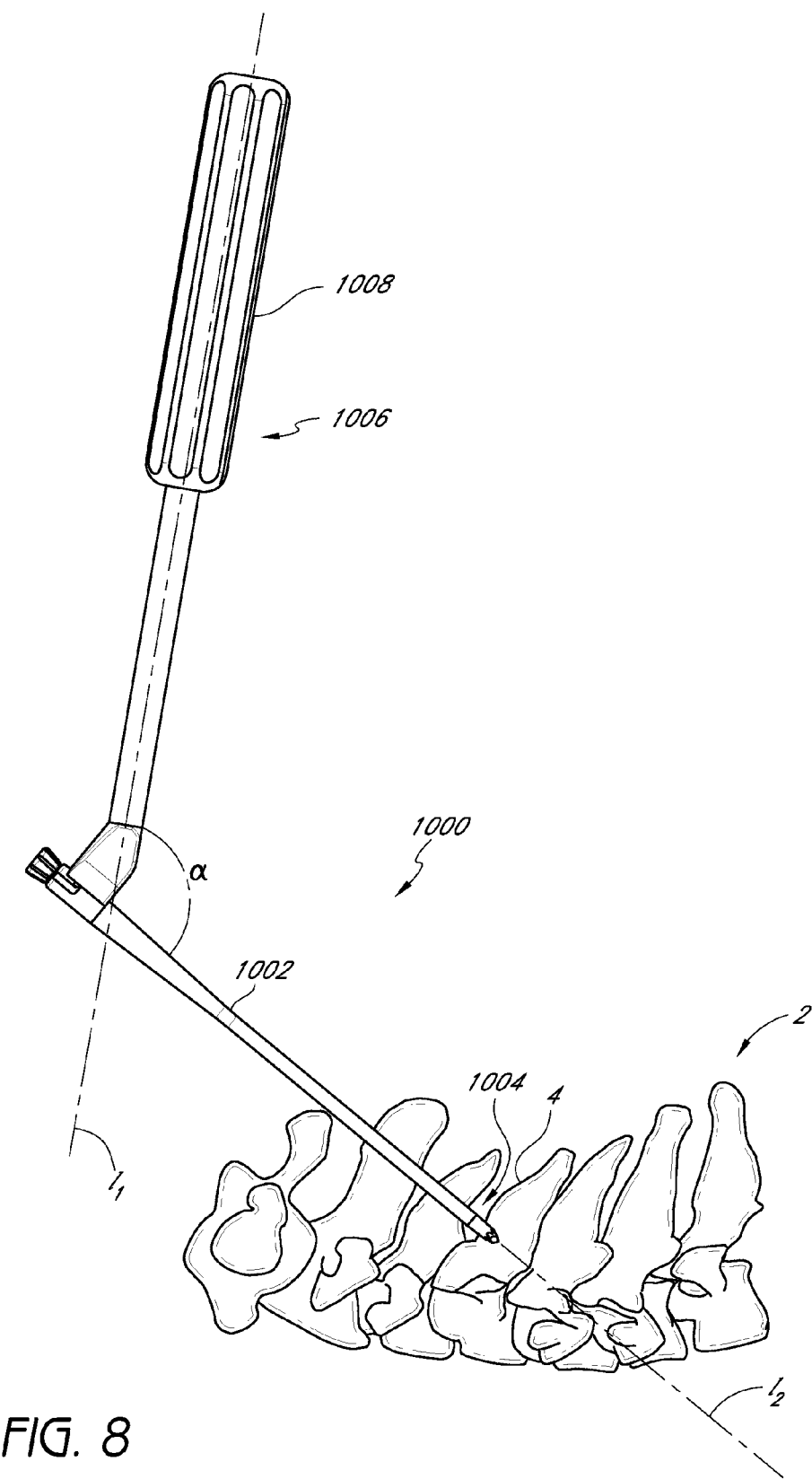
FIG. 8 is a side elevational view of the cervical spine and an embodiment of a wire introducer.

In one embodiment of use, a patient with a spinal instability is identified. The patient is preferably positioned face down on an operating table, placing the cervical spinal column into a normal or flexed position as shown in FIG. 1. With reference FIG. 8, a wire introducer 1000 is inserted through a tissue tract and advanced towards a first vertebra 4 in the cervical spine 2. As mentioned above, due to the anatomy of the cervical spine 2, the fixation device may need to extend along a axis that when extended interferes with the back of the patient's head (see e.g., FIG. 1). Accordingly, in the illustrated embodiment, the wire introducer 1000 (which will be described in more detail below) includes a cannulated section 1002 with a trocar 1004 positioned within the cannulated section and a handle 1006 coupled to the cannula portion 1002. The handle 1006 and the cannulated section 1002 are arranged such that their longitudinal axes l2, l1 form an angle α. In this manner, a gripping portion 1008 of the handle 1006 is positioned above the cannula portion 1002. This allows the surgeon to grip and securely hold the wire introducer 1000 with reduced interference from the back of the patient's head. Thus, using visualization techniques, the distal end of the trocar 1004 can be advanced towards point toward the vertebra 4 without interfering with the back of the patient's head.

In the illustrated embodiment, the angle α. between the handle 1006 and the cannula portion 1002 is in one embodiment greater than 90 degrees and, in other embodiments, within a range between about 30 degrees and 150 degrees. In the illustrated embodiment, the angle α. is about 120 degrees. An advantage of the illustrated embodiment is that the surgeon's hand can be positioned offset from the longitudinal axis l2 of the cannula portion. This improves the leverage and ergonomics involved with advancing the wire introducer 1000 through the tissue tract towards the first vertebra 4 in the cervical spine 2.

Figure 9:
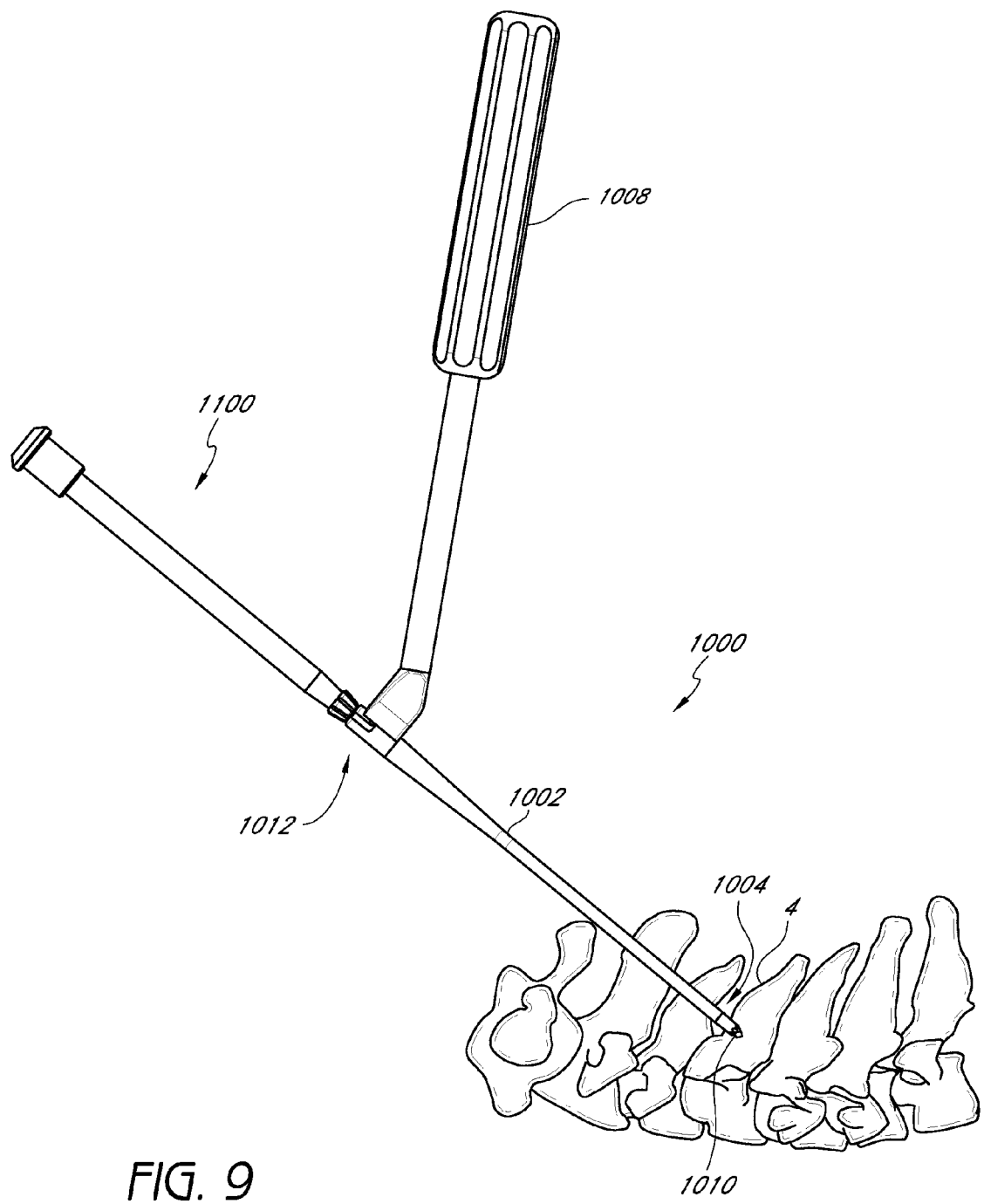
FIG. 9 is a side elevational view of the cervical spine and the wire introducer of FIG. 8 with an embodiment of a strike pen coupled thereto.

With reference now to FIG. 9, when the end of the trocar 1004 is positioned at the desired location on the vertebra 4, a strike pin 1100 can be coupled to the proximal end of the introducer 1000. As will be explained in more detail below, mating threads or other coupling features can be provided between the introducer 1000 and the strike pin 1100. The strike pin 1100 can then be tapped with a mallet or hammer (not shown) by the clinician to set the end of the trocar 1004 into the facet of the vertebra 4. This advantageously also sets the sharp distal end 1010 of the wire introducer 1000 into the facet. In a modified embodiment, the strike pin 1100 can form part of the introducer 1000 and/or the introducer 1000 can be lengthened in the proximal direction such that the patient is not contacted when a hammer is used. In another embodiment, the hammer can be used directly against the proximal end of the introducer 1000.

Figure 10:
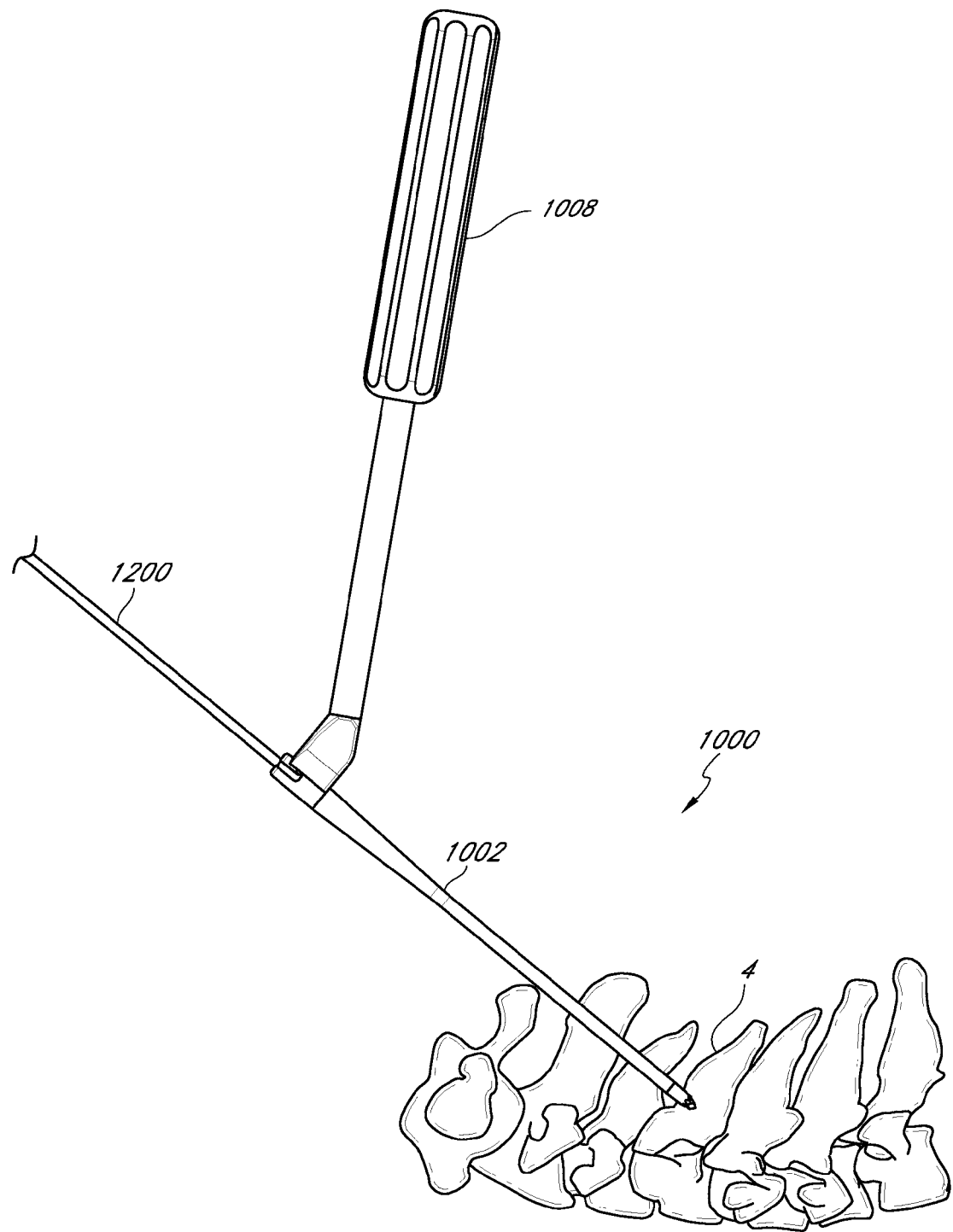
FIG. 10 is a side elevational view of the cervical spine and the wire introducer of FIG. 8 with its trocar removed and an embodiment of sharp guidewire inserted therein.

As shown in FIG. 10, the strike pin 1100 and the trocar 1004 (FIG. 8) can be removed from the wire introducer 1000. As will be explained in more detail below with respect to FIG. 21, in the illustrated embodiment, a bayonet connection 1012 can be provided between the introducer 1000 and the trocar 1004. By releasing the bayonet connection 1012, the trocar 1004 can be released and removed from the introducer 1002.

Figure 11:
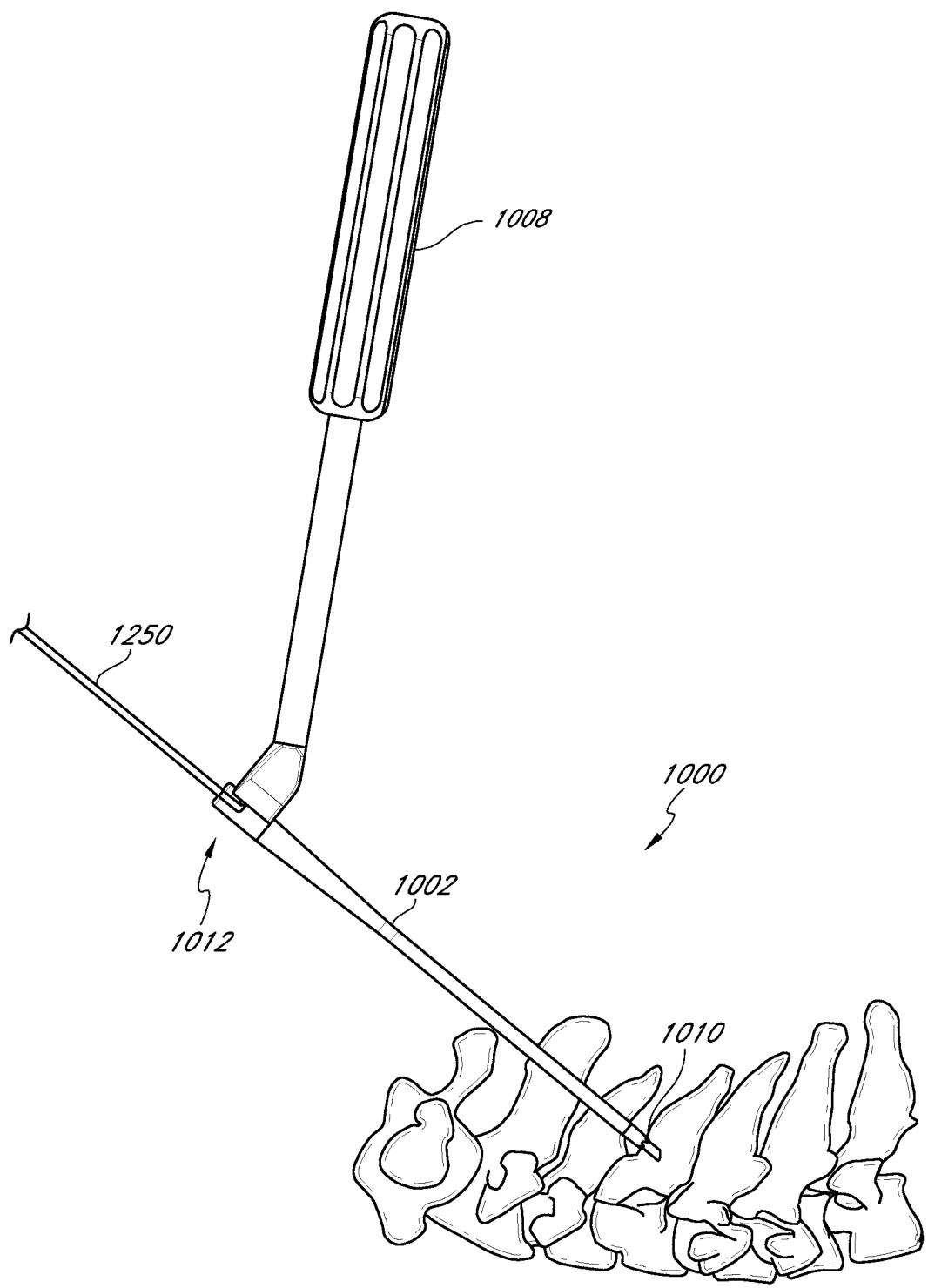
FIG. 11 is a side elevational view of the cervical spine and the wire introducer of FIG. 8 with its trocar removed and an embodiment of blunt guidewire inserted therein.
Figure 12:
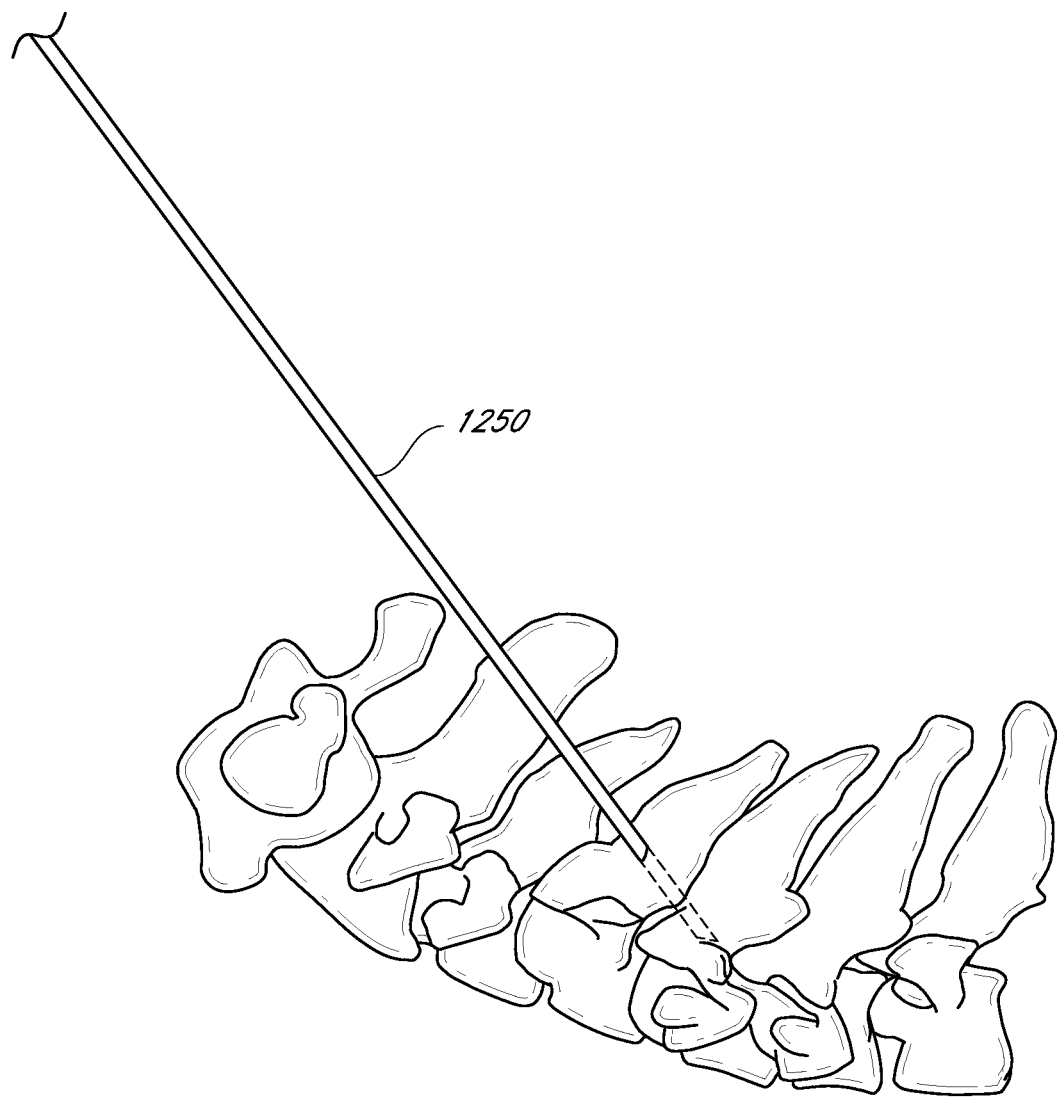
FIG. 12 is a side elevational view of the cervical spine with the blunt guidewire of FIG. 11 and the wire introducer of FIG. 8 removed.

With the trocar 1004 removed, a guidewire (e.g., a 0.070 diameter K-wire) 1200 can be used as a predrill for the fixation device (see FIG. 10). In one embodiment, the guidewire 1200 has a drill-type distal end and is advanced through the introducer 1000 to the desired fixation device location. The guidewire can then be coupled to a drill (not shown) and then advanced into the vertebra 4 to provide a pre-drill hole for the fixation device. In a modified embodiment, a drill with a drill bit similarly sized to the guidewire 1200 can be used. With reference to FIG. 11, the guidewire 1200 can be removed and can be replaced with a preferably blunt ended guidewire wire 1250 (e.g., a 0.45" diameter NiTi wire). The wire introducer 1000 can then be removed leaving the guidewire wire 1250 in place (see FIG. 12). Advantageously, the blunt wire 1250 does not advance through the vertebrae in to the nerves and tissue of the spinal column.

Figure 13:
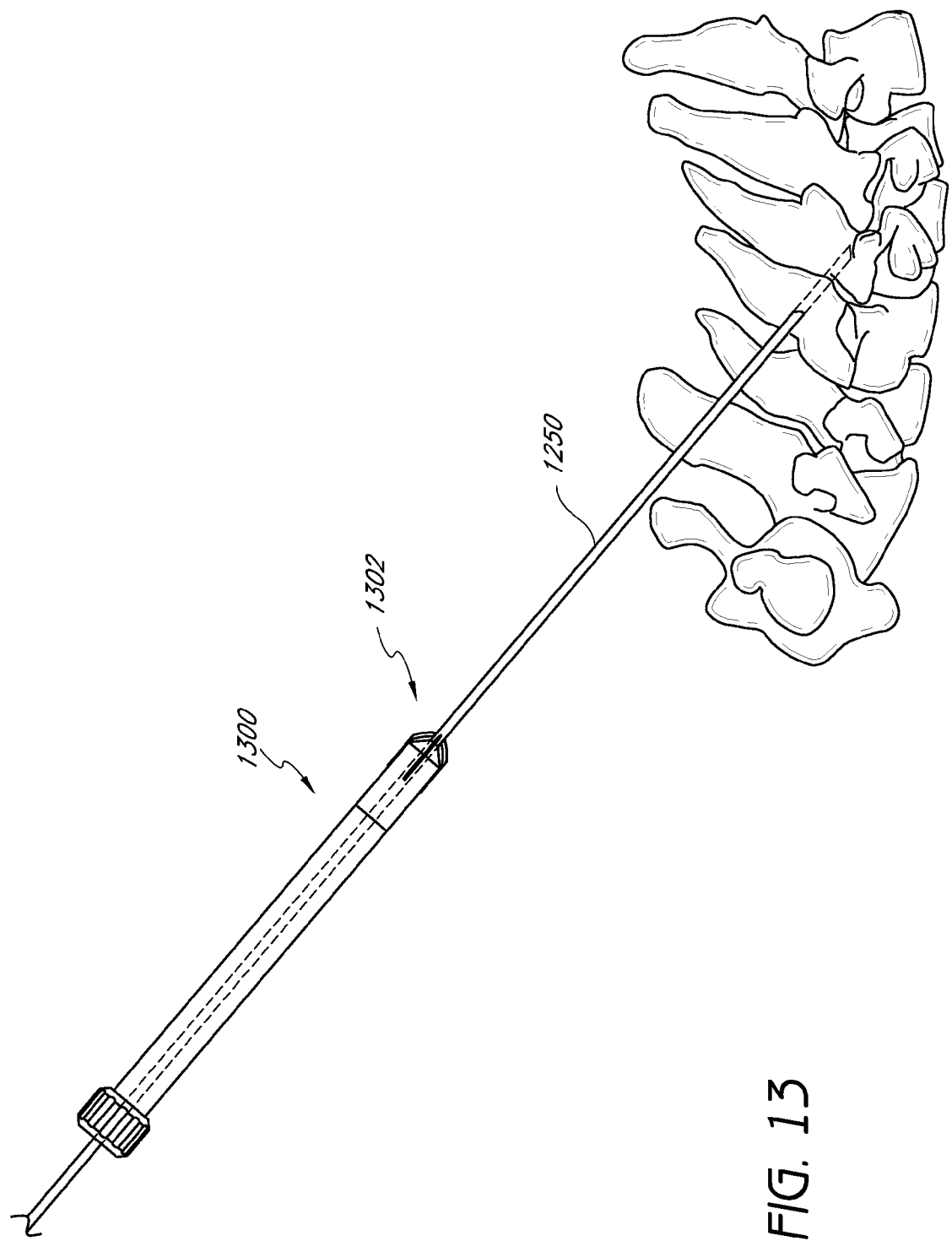
FIG. 13 is a side elevational view of the cervical spine with the guidewire of FIG. 11 and an embodiment of a fascia cutter inserted over the guidewire

With reference now to FIG. 13, adjacent the guidewire 1250 a small incision (e.g., 8-10 mm length) can be made to accommodate a fascia cutter 1300, which will be described in more detail below. The fascia cutter 1300 includes a sharp distal end 1302 that is configured to cut the tough fascia tissue that lies above the cervical spine. As shown in FIG. 13, the fascia cutter 1300 can be advanced over the guidewire 1250 into the incision. The fascia cutter 1300 is advanced over the guidewire 1250 until the fascia is sufficiently cut. The fascia cutter 1300 can then be removed leaving the guidewire 1250 in place. Some embodiments of a method to implant a spinal fixation device do not include using a fascia cutter. In some embodiments, cutting the fascia can include cutting with a scalpel in place of or in addition to the fascia cutter 1300.

Figure 14:
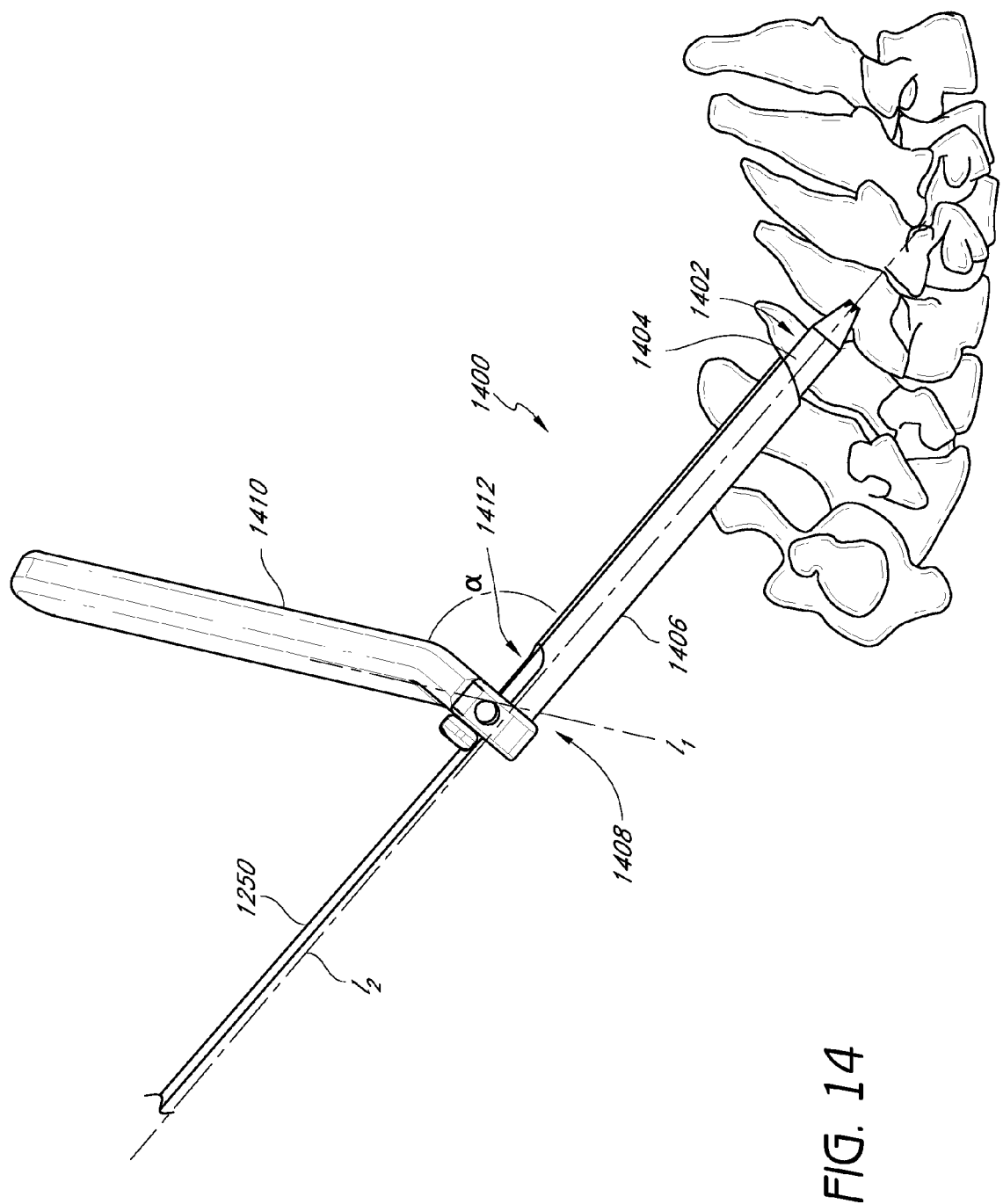
FIG. 14 is a side elevational view of the cervical spine with the guidewire of FIG. 11 and an embodiment of a sheath assembly in a first position.

As shown in FIG. 14, a sheath assembly 1400 can now be advanced over the guidewire 1250 through the opening cut into the fascia until its tip 1402 reaches the bone. One embodiment of the sheath assembly 1400 will be described in more detail below. In general, the sheath assembly 1400 is configured to be inserted over the guidewire in a first, low profile, configuration. The sheath assembly 1400 can then be converted to a second, larger profile, configuration (see FIG. 15) in which the sheath assembly 1400 provides a larger access lumen to the target site (e.g., the vertebrae). In the illustrated embodiment, the sheath 1400 includes inner and outer sheaths 1404, 1406 in a manner as described in U.S. Patent Publication No. 2006/0030872, filed Aug. 3, 2004, application Ser. No. 10/911,214 which is hereby incorporated by reference herein in its entirety. In the first configuration (see FIG. 14), the sheath 1400 is advanced until the tip 1402 of the inner sheath 1404 reaches the bone. An actuator 1408 is then released to advance the outer sheath 1406 downward over the inner sheath 1404 until the outer sheath 1406 is resting on the facet (see FIG. 15). The inner sheath 1404 is then removed, preferably leaving the guidewire 1250 and outer sheath 1406 in place.

Figure 15:
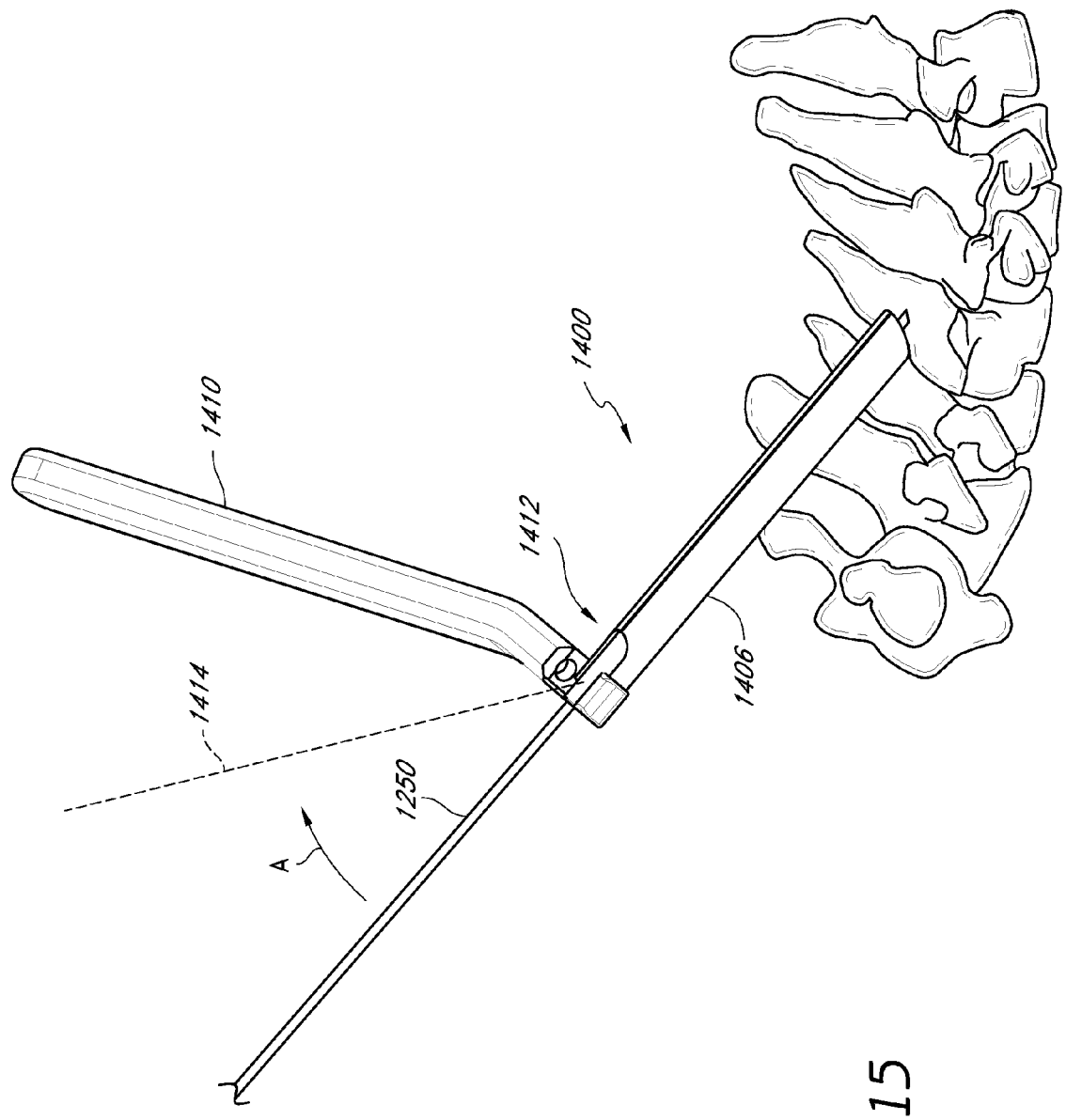
FIG. 15 is a side elevational view of the cervical spine with the guidewire of FIG. 11 and an embodiment of the sheath assembly of FIG. 14 in a second position with a center portion removed.

As mentioned above, due to the anatomy of the cervical spine 2, the fixation device may need to extend along an axis that, when extended, interferes with the back of the patient's head (see e.g., FIG. 1). Accordingly, as shown in FIGS. 14 and 15, the sheath assembly 1400 can include a handle 1410 that is coupled to the outer sheath 1406. Similar to the handle 1008 of the wire introducer 1000 (FIG. 8), the handle 1410 and the outer sheath 1406 are arranged such that their longitudinal axes l1, l2 form an angle α. In this manner, the handle 1410 is positioned offset from the outer sheath 1406. This offset positioning allows the surgeon to grip and securely hold the outer sheath 1406 with reduced interference from the back of the patient's head.

In the illustrated embodiment, the angle α. between the handle 1410 and the outer sheath 1406 is in one embodiment greater than 90 degrees and, in other embodiments, within a range between about 30 and 150 degrees. In the illustrated embodiment, the angle α. is about 120 degrees. An advantage of the illustrated embodiment is that the surgeon's hand can be positioned offset from the longitudinal axis l2 of the outer sheath 1406. This offset positioning improves the leverage and ergonomics involved with holding the outer sheath 1406 in place during the various procedures described below.

The outer sheath 1406 can desirably also include an elongated proximal opening or slot 1412, which generally faces the handle 1410. The slot 1412 facilitates placing instruments into the outer sheath 1406 by allowing the instrument to be moved in the direction A (see FIG. 15) towards line 1414, which is transverse to the longitudinal axis 12 of the outer sheath 1406. In this manner, interference with the patient's head can be reduced.

Figure 16:
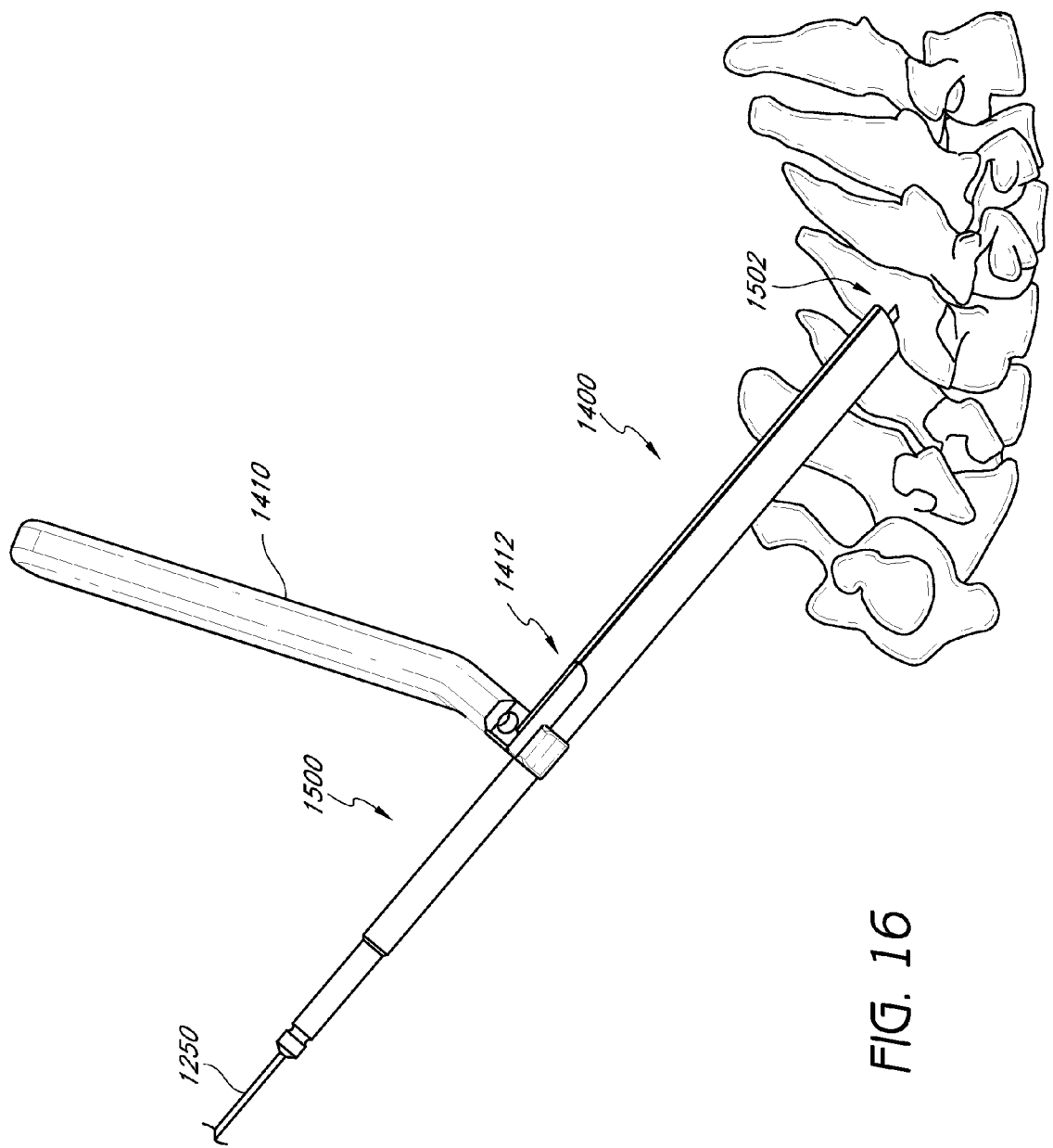
FIG. 16 is a side elevational view of the cervical spine with the guidewire of FIG. 11 and the sheath assembly of FIG. 14 with a drill inserted therein.

With reference now to FIG. 16, a cortex drill 1500 is advanced towards the vertebrae through the sheath assembly 1400 and over the guidewire 1250. As will be explained in more detail below, the cortex drill 1500 preferably can be powered to make a clearance hole and counter sink in the facet for the implant and the proximal anchor. In some embodiments, the drill 1500 preferably includes a flexible elongated transmission member as will be described below. This flexible transmission member allows a proximal end of the drill 1500 to be flexed in the direction of arrow A and line 1414 of FIG. 15 while a distal end 1502 of the drill 1500 maintains a desired position and orientation with respect to the vertebrae. As will be explained below, the distal end 1502 of the drill 1500 can be configured to form a clearance hole and/or counter sink for the fixation device to be inserted into the vertebrae. In one embodiment, the drill 1500 is coupled to a power instrument.

After the cortex drill 1500 is removed, a tapping instrument 1600 (see FIG. 17) can be advanced over the guidewire 1250. In some embodiments, the tapping instrument 1600 is rotated, by hand, and advanced into the vertebrae. As will be explained in more detail below, the tapping instrument 1600 preferably includes a handle (not shown in FIG. 17) at a proximal end and a tapping portion 1602 at a distal end. The handle and tapping portion 1602 can desirably be connected by a flexible rotation transmission member 1604. In other embodiments of the device, the fixation device can be configured to be self-tapping. In such an embodiment, the tapping instrument 1600 can be eliminated.

Figure 18:
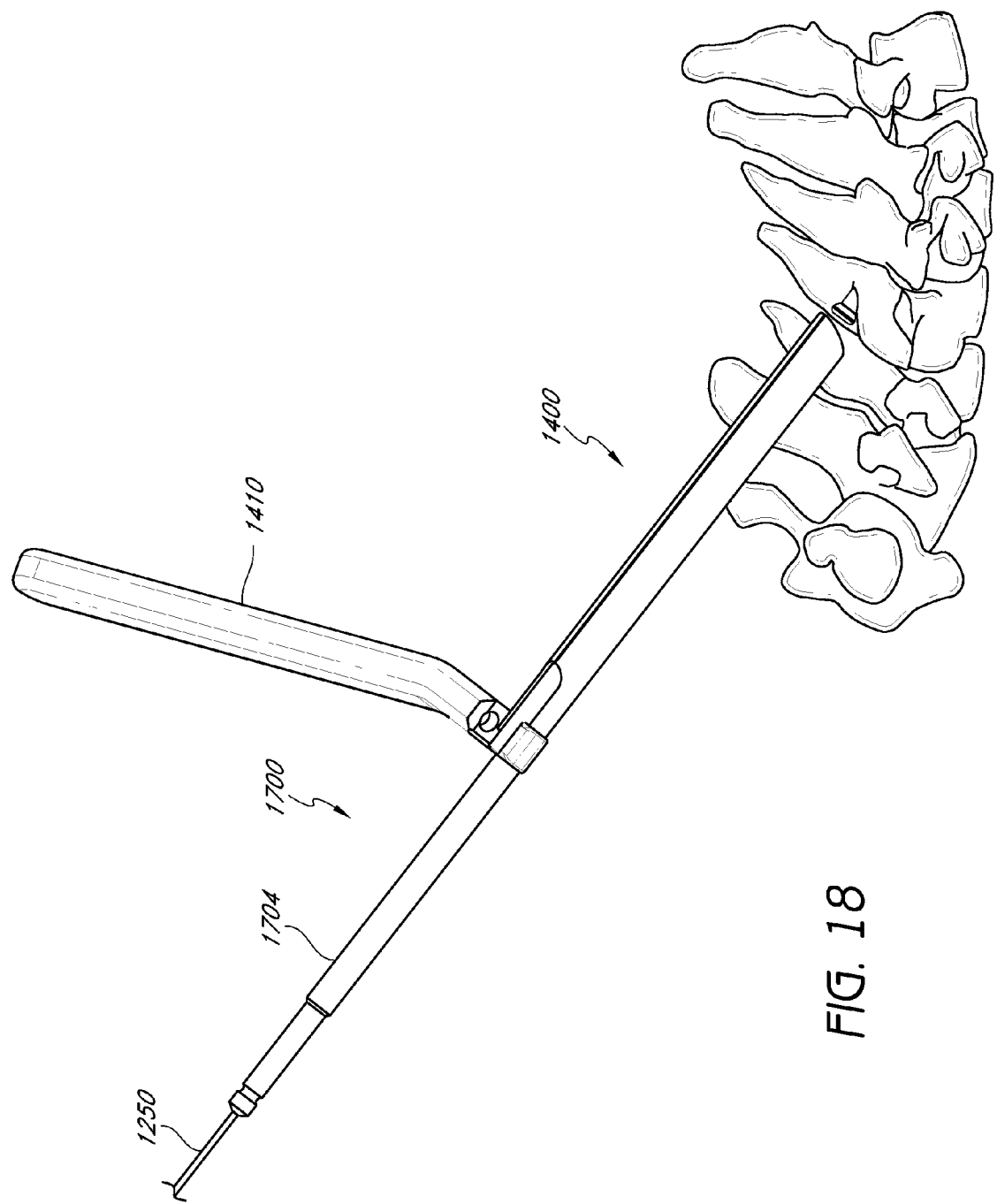
FIG. 18 is a side elevational view of the cervical spine with the guidewire of FIG. 11 and the sheath assembly of FIG. 14 with a driving device inserted therein.

With a hole tapped, the tapping instrument 1600 can be removed from the sheath assembly 1400. Then, with reference to FIG. 18, a driver 1700 can be used to advance a fixation device (e.g., the fixation device 212 as described above) over the guidewire 1250, through the sheath assembly 1400 to the vertebrae. As will be explained below, the distal end 1702 of the driver 1700 (not shown in FIG. 18) is configured to engage a proximal end of the fixation device. The driver 1700 preferably also includes a flexible rotation member 1704 as further described below.

With the distal anchor 234 of a fixation device 212 positioned properly in the vertebrae, the driver 1700 can be decoupled from the fixation device and removed from the sheath assembly 1400. A compression device 1800, which will be described in more detail below, can then be advanced over the guidewire 1250 and through the sheath assembly 1400. The compression device 1800 can be used to advance the proximal anchor 700 over the body 228 of the device 212. As will be explained in detail below, the compression device 1800 can include a distal end 1802 configured to engage the fixation device 212, a handle 1806 and flexible transmission member 1804 extending between the distal end 1802 and handle 1806.

In this manner, the proximal anchor 700 can be advanced distally with respect to the body 228 until the proximal anchor 700 fits snugly against the outer surface of the vertebra or a fixation plate/rod. As explained above, one advantage of the structure of the illustrated embodiments is the ability to adjust compression independently of the setting of the distal anchor 234 within the vertebra. That is, with the distal anchor properly positioned within the inferior vertebra, proper compression (and/or length of the device) between the superior and inferior vertebrae is achieved by advancing the proximal anchor over the body (and/or retracting the body with respect to the proximal anchor).

Figure 20:
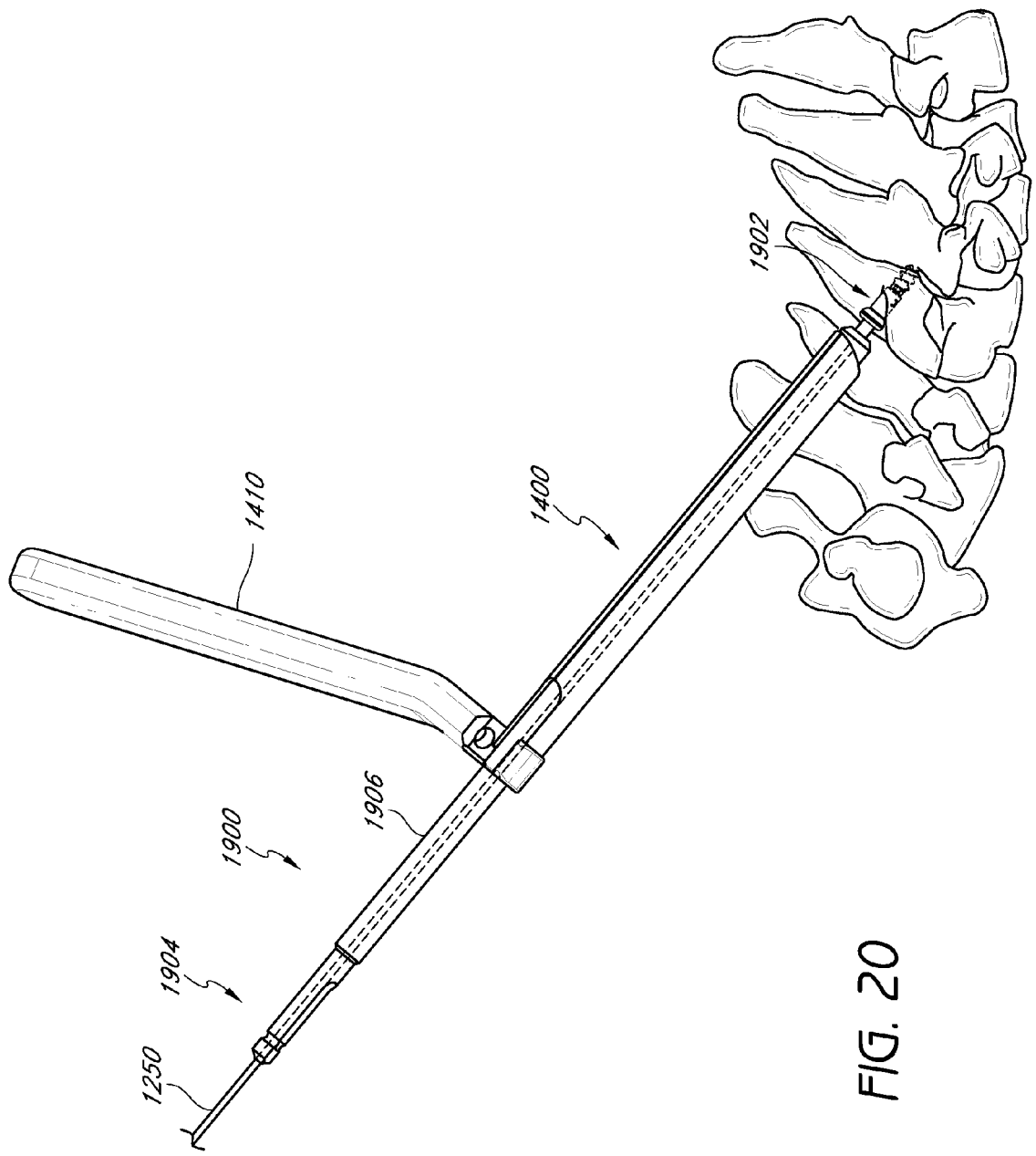
FIG. 20 is a side elevational view of the cervical spine with the guidewire of FIG. 11 and the sheath assembly of FIG. 14 with a pin removal device inserted therein.

After compression has been applied to the fixation device the compression device 1800 can be removed. As shown in FIG. 20, the second portion of the body of the fixation device can then be removed using a pull-pin remover 1900, which will be described in further detail below. As with the tools used with the sheath assembly 1400 described above, the pin remover 1900, preferably includes a distal end 1902, a proximal end 1904 and a flexible transmission member 1906 extending therebetween. In modified embodiments, the second portion of the body can be left in the patient. In other embodiments, the second portion can be removed by cutting the body.

With the second portion (or pull pin) of the body removed, the sheath assembly 1400 and the wire 1250 can be removed. The access site may be closed and dressed in accordance with conventional wound closure techniques and the steps described above may be repeated on the other side of the vertebrae for substantial bilateral symmetry. The bone stabilization devices 212 may be used alone or in combination with other surgical procedures such as laminectomy, discectomy, artificial disc replacement, and/or other applications for relieving pain and/or providing stability.

It should be appreciated that not all of the steps described above are critical to procedure. Accordingly, in some embodiments, some of the described steps may be omitted or performed in an order different from that disclosed. Further, additional steps may be contemplated by those skilled in the art in view of the disclosure herein, without departing from the scope of the present inventions. In addition, while the above-described methods are described with reference to the cervical spine and a trans-facet application, in other embodiments, certain aspects and features of the devices and techniques herein can be used in other portions of the spine (e.g., lumbar) and/or other techniques (e.g., pedicle screws and constructs). They can also be used with other procedures (e.g., anterior cervical decompression and fusion, ACDF).

Additional details of the various tools and components described above will now be presented.

Figure 21:
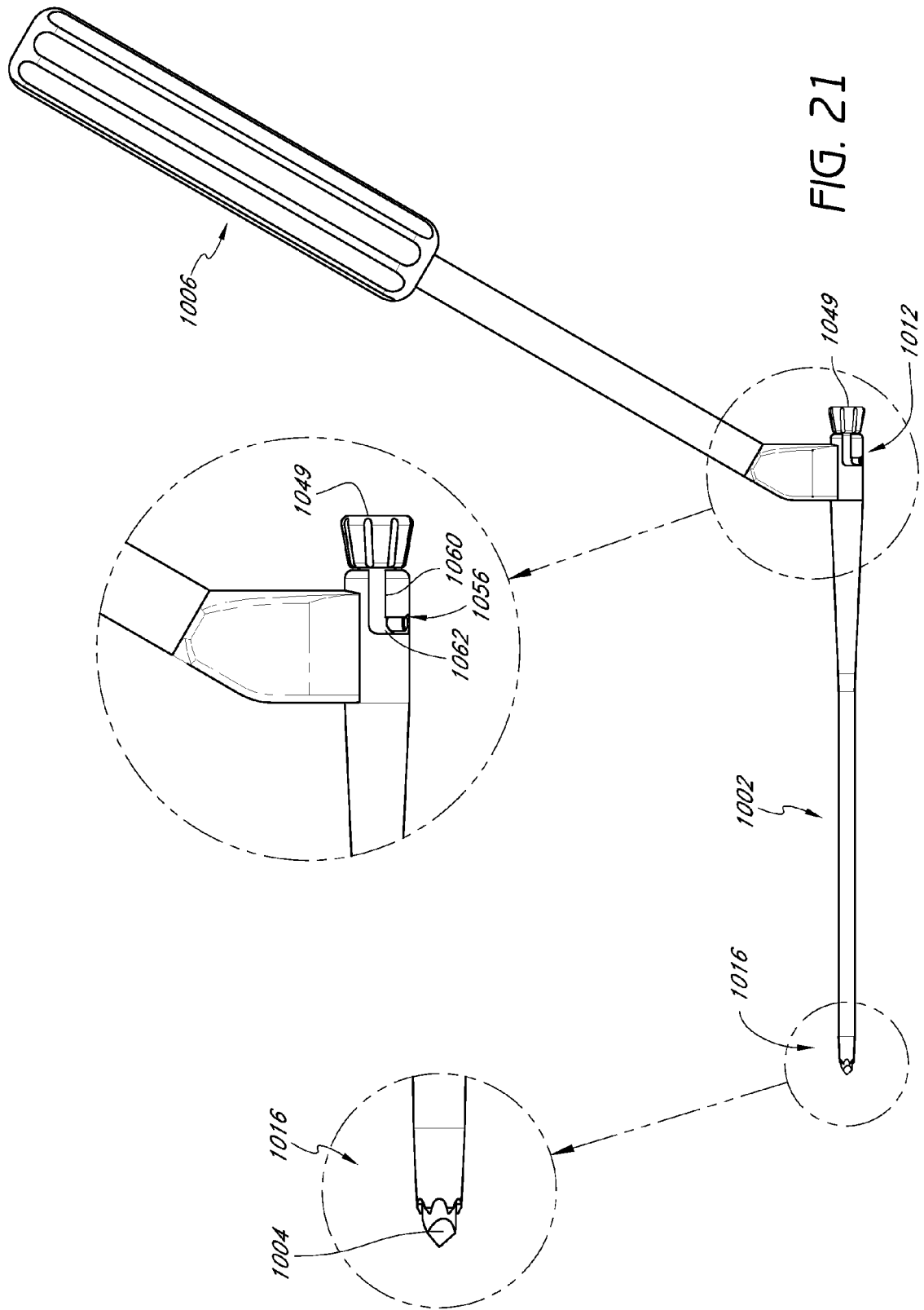
FIG. 21 is a side view of the wire introducer of FIG. 8.

FIGS. 21, 21A-21F and 22A-D illustrate various views of the wire introducer 1000 and trocar 1004 described above with reference to FIG. 8. With initial reference to FIG. 21, the illustrated wire introducer 1000 generally comprises a wire cannula portion 1002 coupled to a handle 1006. As shown in FIGS. 21A and 21B, the wire cannula portion 1002 comprises a generally tubular, elongated body 1014 that defines an inner lumen 1015, which is configured to receive the trocar 1004. The body 1014 includes a distal end 1016 and a proximal end 1018, which includes part of the bayonet connection 1012 described above.

With reference to FIG. 21E, in some embodiments, the distal end 1016 can preferably include a plurality of teeth 1020 with sharpened edges 1022. The teeth 1020 and edges 1022 are configured to aid the insertion of the distal end 1016 of the introducer 1000 through the patient's tissue and in embedding the wire introducer 1000 into the vertebrae. The distal end 1016 preferably has a tapered outer profile 1024 as shown in FIG. 21E.

Figure 21G:
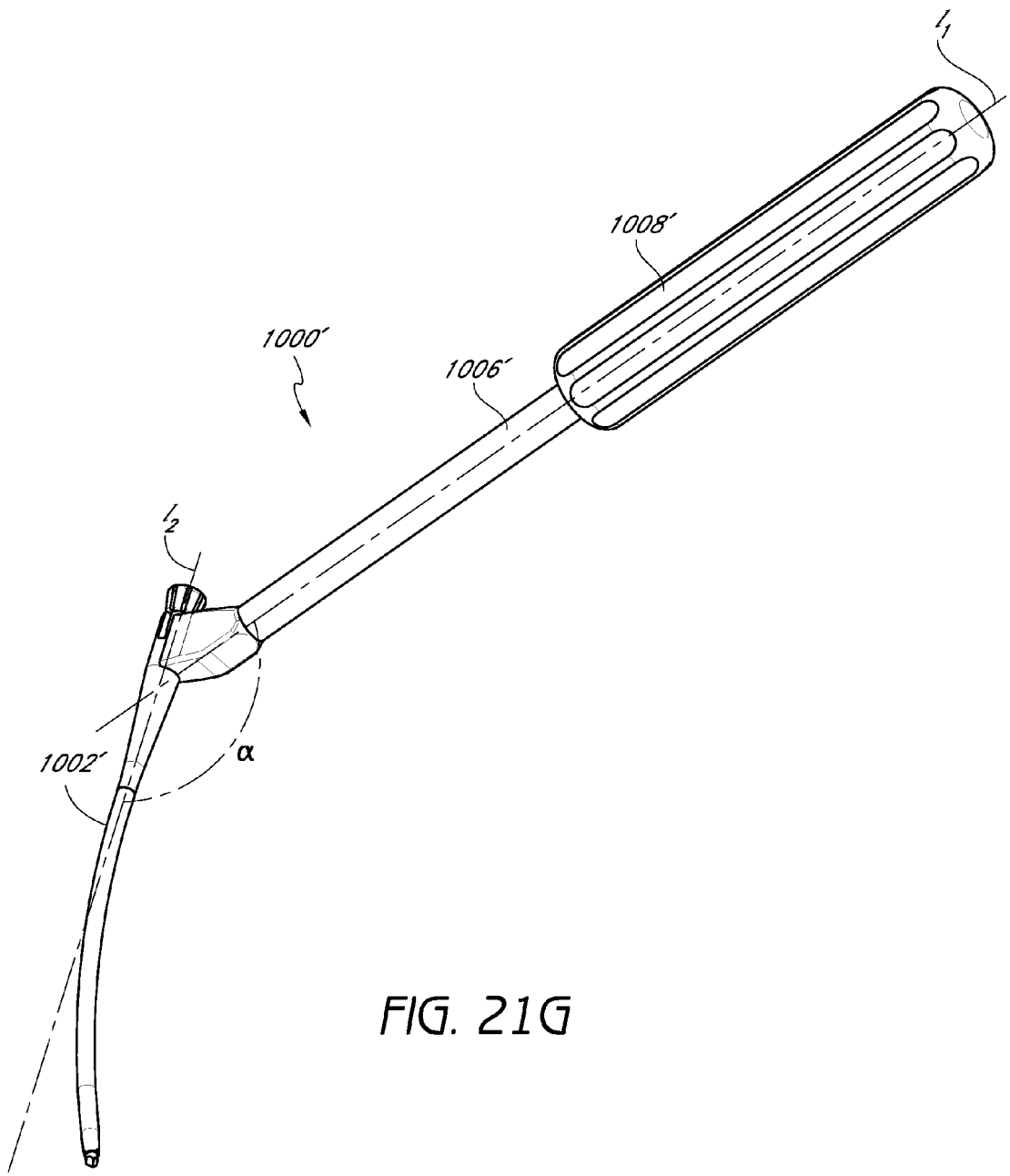
FIG. 21G is a perspective view of another embodiment of a wire introducer.

With reference to FIG. 21G, in some embodiments, a wire introducer 1000' can include a wire cannula portion 1002' coupled to a handle 1006'. The wire cannula portion 1002' comprises a curved tubular member. The curved tubular member defines a longitudinal axis, l2 extending generally between the ends of the wire cannula portion 1002'. The handle 1006' and the wire cannula portion 1002' are arranged such that their longitudinal axes l2, l1 form an angle α. In this manner, a gripping portion 1008' of the handle 1006' is positioned offset from the cannula portion 1002' as described above with respect to FIG. 8.

FIG. 22A illustrates a first portion 1030 of the trocar 1004. The first portion 1030 comprises an elongated body with a distal end 1034 and a proximal end 1036. The distal end 1034 preferably includes a sharpened tip 1040, which is configured to pierce tissue. The proximal end 1036 is configured to be coupled to a handle 1032 (or integrally formed therewith), which is shown in FIGS. 22B-D. In the illustrated embodiment, the proximal end 1036 of the first portion 1030 is press fitted into a cavity 1042 formed in the handle 1032.

With reference to FIGS. 22C-D, the handle 1032 preferably includes a distal end 1044, a proximal end 1046 and a middle portion 1048 extending therebetween. The distal portion 1044 includes the cavity 1042 described above. The proximal portion 1046 includes a enlarged diameter gripping portion 1049, which can include gripping features 1051 such that the trocar 1004 can be grasped and rotated. The proximal end can also include a cavity 1050 for receiving a distal end of a strike pin 1100 as will be described below. In one embodiment, the cavity 1050 includes threads (not shown).

The middle portion 1048 preferably includes a through hole 1054, which extends generally perpendicularly with respect to the longitudinal axis of the trocar 1004. A bayonet pin 1056 (see FIG. 22D) can be positioned within the through 1054 with its ends extending beyond the middle portion 1048.

With reference back to FIG. 21, when the trocar 1004 is positioned within the wire introducer 1000, the sharpened tip 1040 of the trocar extends beyond the distal end 1016 of the wire introducer 1000. Together the two instruments 1000, 1004 form a sharpened tip that is configured to pierce tissue. In certain embodiments, a stab incision may need to be used to introduce the wire introducer into the patient. In the illustrated embodiments, the instruments 1000, 1004 are coupled together by the bayonet connection 1012. Specifically, with reference to FIGS. 21, 21B, 21D, 21F, the proximal end 1018 of the wire introducer 1000 includes a slot or groove 1060, which extends along the longitudinal axis of the introducer 1000. The groove 1060 terminates in a side groove 1062 to form a L-shaped bayonet connection 1012. Thus, the trocar 1004 can be secured within the wire introducer 1000 when the pin 1056 is positioned within the side groove 1062. To remove the trocar 1004 from the wire introducer, the wire introducer 1000 can held in place with the handle 1006 with one hand while the other hand grips the gripping portion 1049 of the trocar 1004 and rotates the trocar 1004 to align the pin 1056 with the groove 1060. The trocar 1004 can then be withdrawn and removed from the wire introducer 1000.

With reference now to FIGS. 23A-C, the strike pin 1100 will now be described in more detail. As mentioned above, the strike pin can be used to set the tip of the trocar 1004 into the facet. In the illustrated embodiment, the strike pin 1100 comprises a generally elongated body 1102 with a proximal end 1104 and a distal end 1106. The proximal end 1104 can include an enlarged portion 1108, which can be configured to receive a striking force from a hammer or mallet. The distal end 1106 of the device can included a threaded portion 1110, which is configured to be threaded into the cavity 1050 of the trocar 1004. In this manner, the strike pin 1100 can coupled to the wire introducer 1000 and trocar 1004. In modified embodiments, the strike pin 1100 and cavity 1050 can be formed without threads and/or with other mechanisms for coupling the two components together (e.g., prongs, O-rings etc.). In the embodiment that includes threads, the threads are preferably configured such that coupling the strike pin 1100 to the trocar 1004 involves rotating the strike pin 1100 in a direction (e.g., clockwise) that is the same direction which is used to rotate the trocar 1004 to release it from the bayonet connection 1012. After the trocar 1004 is set into the facet, the trocar 1004 can be removed from the introducer 1000 while remaining coupled to the strike pin 1100 or, in another embodiment, the strike pin 1110 can be decoupled from the trocar 1004 before the trocar is removed from the introducer 1000.

FIGS. 24A-B illustrate the guidewire 1200 shown in FIG. 10. As shown, in the illustrated embodiment, the guidewire 1200 includes a sharpened or trocar-type tip 1202. As mentioned above, this guidewire 1200 can be coupled to a drill with a wire driver to pre-drill a small hole into the vertebrae.

FIG. 25 illustrates the blunt ended guidewire 1250, which is shown in FIG. 11. This guidewire 1250 can be inserted into the hole formed by the sharp ended guidewire 1200 described above. The guidewire 1250 can then be used to guide various instruments which are advanced over the guidewire 1250. In this manner, the sharpened guidewire 1200 can be used to form the initial hole and the blunt guidewire 1250 can be used to guide instruments. In this manner, the blunt guidewire 1250 does not advance further into the vertebrae, which can cause harm if the guidewire is advanced into the spinal column.

The fascia cutter 1300, which was introduced in FIG. 13, will now be described with initial reference to FIGS. 26A-E. As shown, in the illustrated embodiment, the fascia cutter 1300 includes a generally elongated body 1304 that has a distal end 1302 and a proximal end 1306. The body 1304 preferably defines a guidewire lumen 1308 such that the cutter 1300 can be advanced over the guidewire 1250 described above.

The proximal end 1306 of the cutter 1300 can include an enlarged diameter portion 1310 with knurling or other gripping features to facilitate manipulation of the cutter 1300. The distal end 1302 of the device preferably includes a plurality of cutting instruments 1312 which are configured to cut the fascia in the cervical region of the patient.

Figure 26E:
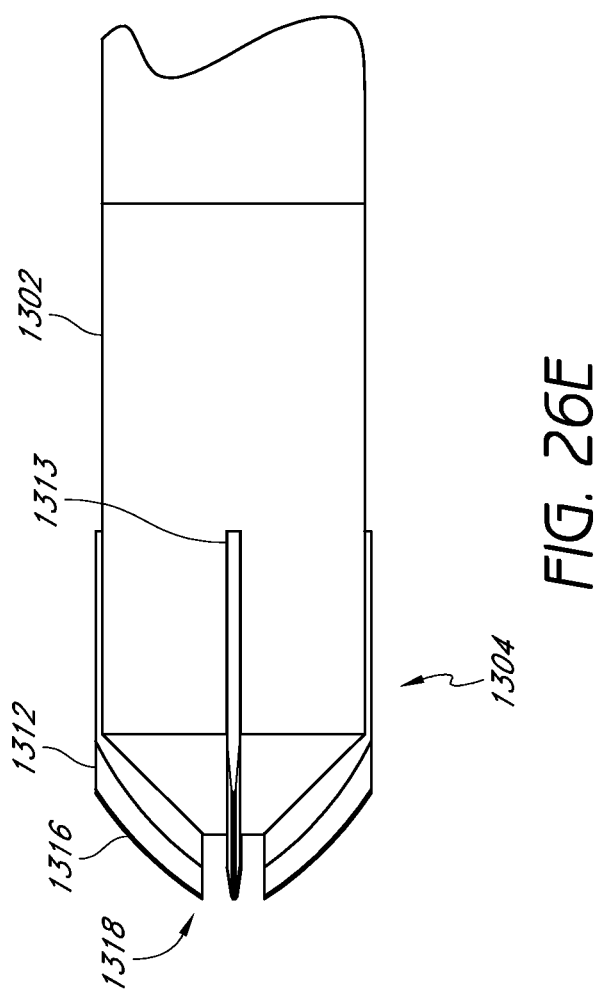
FIG. 26E is an enlarged view of a distal end of the fascia cutter of FIG. 13.

With reference to FIG. 26E, in the illustrated embodiment, the cutter 1300 includes four cutting elements 1312 arranged with slots 1313 formed in the body 1304. In the illustrated embodiment, the cutting elements 1312 are generally equiangularly positioned about the body 1304 and, thus are arranged at about 90 degrees angular spacing with respect to each other about the body 1304. Each of the cutting elements 1312 preferably includes an accurate shaped cutting edge 1316 that terminates at a distal end in a sharp tip 1318. In other embodiments, other numbers and configurations of cutting elements 1312 can be included on a cutter. One advantage of the illustrated embodiment is that a plurality of cutting elements 1312 are positioned on the distal end of cutters and each of the plurality of cutting elements defines a cutting edge that extends generally radially from the distal end of the guidewire lumen. Thus, the fascia cutter 1300 can be advanced over the guidewire and used to cut the fascia.

Figure 27F:
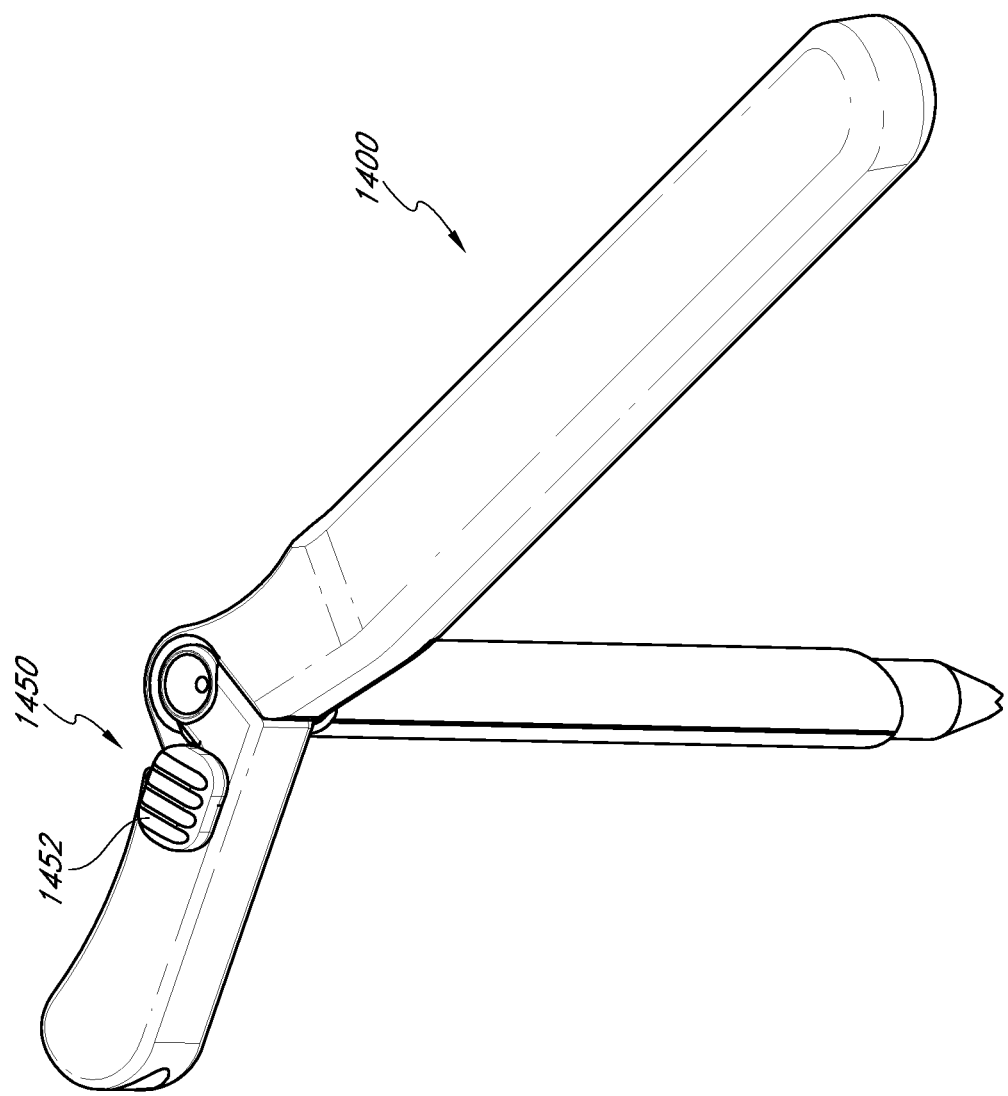
FIG. 27F is a perspective view of the sheath assembly of FIG. 14 from a second viewing angle.

FIGS. 27A-F illustrate in more detail the sheath assembly 1400 introduced above with reference to FIGS. 14 and 15. As shown in FIGS. 27C and 27D, the sheath 1400 includes the first or inner dilator tube 1404 having a distal end 1402 with a tapered tip 1420, and a proximal end 1422 with a locking member 1424, which extends radially from the tube 1404. The first dilator tube 1404 has an inner lumen 1421 with a distal opening and a proximal opening configured to receive the guidewire 1250 described above. The tapered tip 1420 can have a sharpened tip 1426, with a plurality of cutting teeth 1428.

With reference to FIGS. 27A and B, in some embodiments, the assembly can also include the shorter second, outer dilator tube 1406 having a distal end 1430 with a beveled tip 1432 and a proximal end 1434 coupled to the handle 1410. The proximal end 1434 can also include the elongated opening or slot 1412 as described above for receiving various instruments. The second dilator tube 1406 also has an inner lumen 1436 with a distal opening and a proximal opening.

Various mechanisms can be provided for removably coupling the first and second dilator tubes 1404, 1406 together in a locked configuration in which the distal end 1402 of the first tube 1404 extends beyond the distal end 1430 of the second tube 1406 as shown in FIG. 14. In the illustrated embodiment, the first and second tubes 1404, 1406 are coupled together by providing a releasable linking mechanism 1450 (see FIGS. 27E and 27F). In the illustrated embodiment, the releasable linking mechanism 1450 can comprise a spring biased pin that is positioned in the locking member 1424 of the first dilator tube 1404 and, in a first position, locks the two components 1404, 1406 together. Depressing or sliding a button 1452, moves the pin to release the two components 1404, 1406. With the first and second tubes 1404, 1406 unlocked, the second tube 1406 can be advanced over the first tube 1404 to expand the access opening. The inner tube 1404 can then be removed as described above leaving the second tube 1406 and its larger inner lumen 1436 in place at the surgery site. In other embodiments, more or fewer dilator tubes can be used. In addition, other access sheaths can be used.

Additional embodiments and/or details of the sheath assembly 1400 can be found in U.S. Patent Publication No. 2006/0030872, filed Aug. 3, 3004 and entitled "Dilation Introducer for Orthopedic Surgery", which is hereby incorporated by reference herein.

Figure 27G:
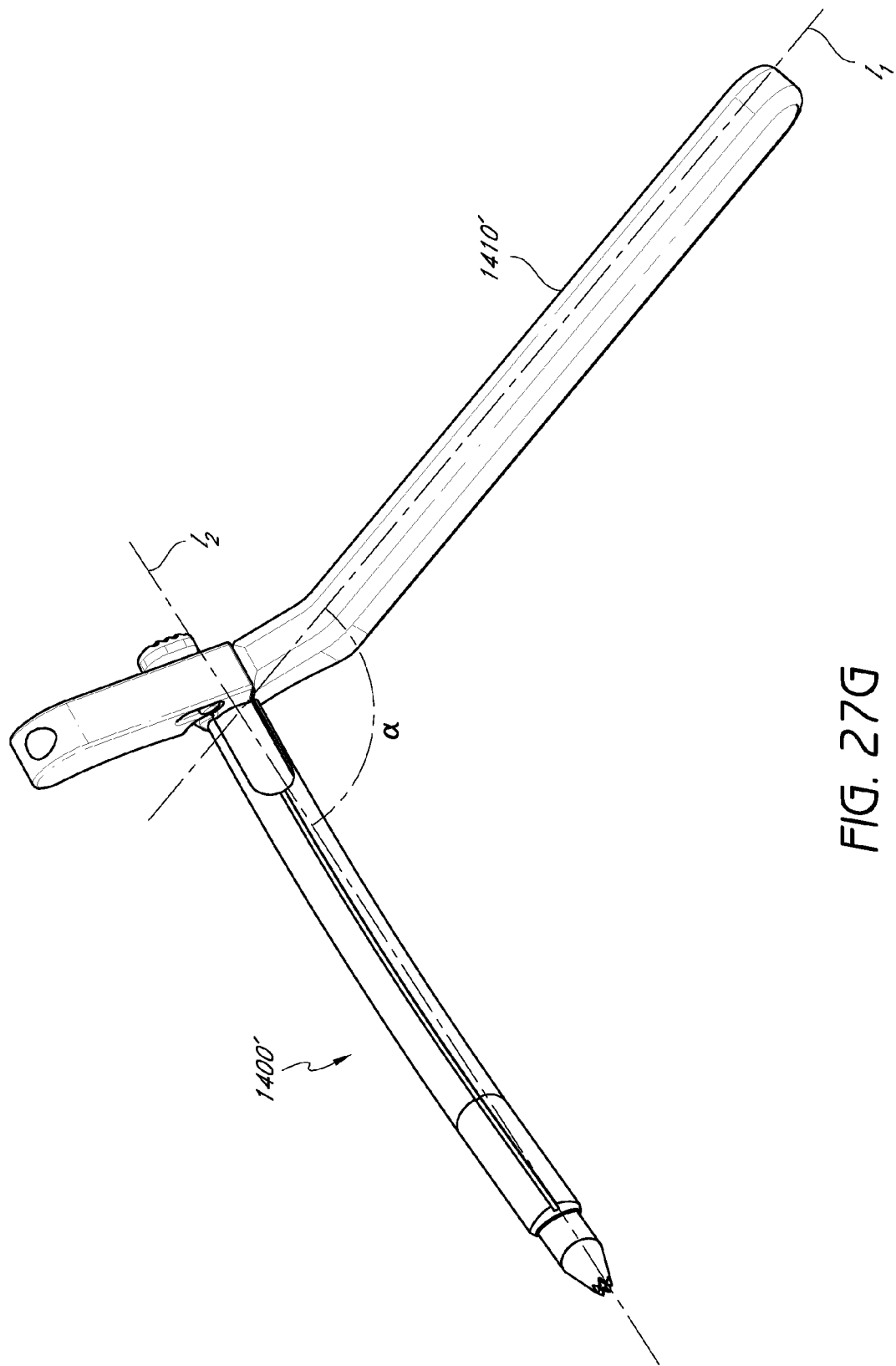
FIG. 27G is a perspective view of another embodiment of sheath assembly.
Figure 271:
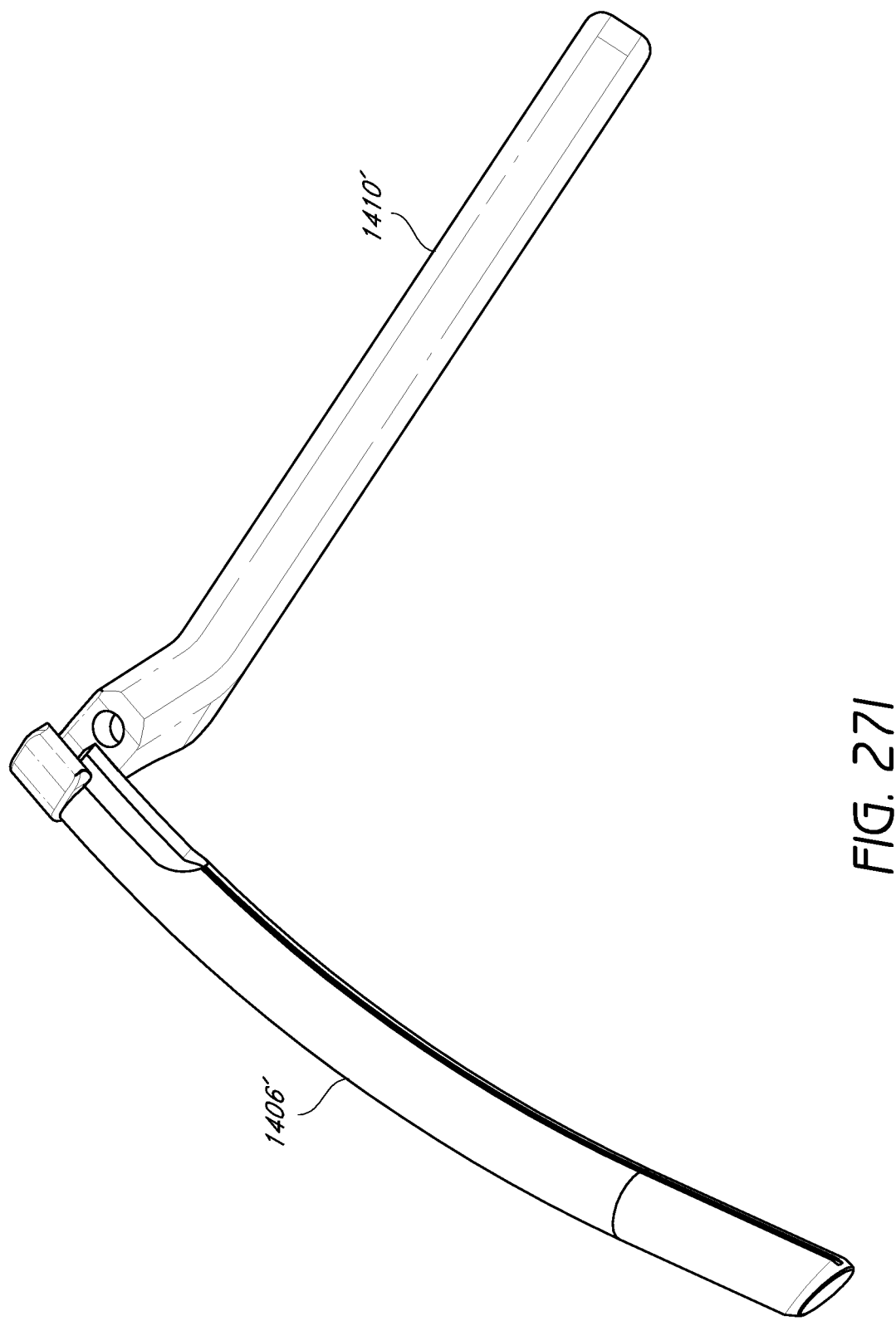

With reference to FIGS. 27G-27I, an embodiment of sheath assembly 1400' is illustrated. The sheath 1400' includes a first or inner dilator tube 1404' and a second, outer dilator tube 1406'. Both the inner and outer dilator tubes 1404', 1406' can have a curved profile. In some embodiments, the inner dilator tube 1404' can be flexible such that it can conform to the curved profile of the outer dilator tube 1406' The dilator tubes 1404', 1406' define a longitudinal axis, l2 that is transverse to a longitudinal axis l1 defined by a handle 1410' of the sheath assembly 1400'.

Figure 28:
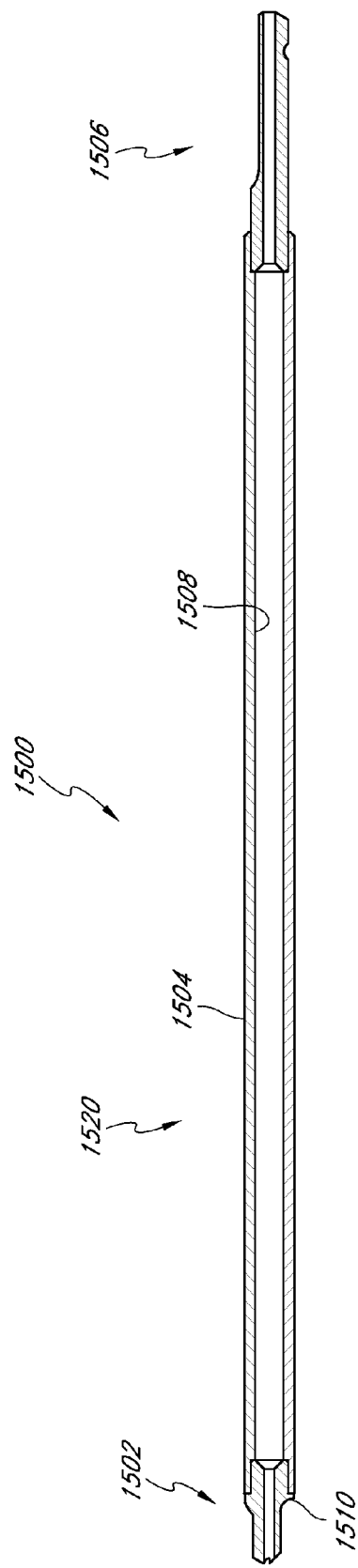
FIG. 28 is a cross-sectional side view of the drill of FIG. 16.

FIG. 28 illustrates an exemplary embodiment of the cortex drill 1500 that was introduced with reference to FIG. 16 above. As mentioned above, the cortex drill 1500 can be used to form a countersink and/or a clearance hole for the fixation device. As shown, the drill 1500 comprises a body 1504 having a distal end 1502, a proximal end 1506 an a guidewire lumen 1508 extending therethrough. The proximal end 1506 can be configured to engage any of a variety of driving tools. In the illustrated embodiment, the proximal end 1506 has a D-shaped cross-section that can be received within a cavity of a hand held gripping device, which will be described below (e.g., in some embodiments, the proximal end can couple with a standard AO quick connect).

With reference to FIGS. 29A-D, the distal end 1502 of the drill 1500 can be provided with a drilling element 1510 comprising a plurality of cutting elements 1512. In the illustrated embodiment the drilling element 1510 includes four cutting elements 1512. In other embodiments, the drilling element 1510 can include more or fewer than four cutting elements 1512. The cutting elements include an outer surface 1514 that preferably generally corresponds to an outer surface profile of the proximal anchor 700 and/or portions of the body 228 of the fixation device 212. The outer surface 1514 can also include with one or more removal or cutting features (e.g., flutes, sharpe edges, etc.) so as to remove or cut bone as the device drill 1500 is rotated.

With reference to FIGS. 30A and 30B, in some embodiments, an elongated transmission member 1520 can extend between the proximal end and the distal end of the drill 1500. In the illustrated embodiment, the transmission member 1520 can be bent about its longitudinal axis as indicated by the arrows in FIG. 30A. Thus the transmission member 1520 in one embodiment is flexible but still capable of transmitting a guiding and/or rotational force to the distal end 1502. In the illustrated embodiment, the transmission member 1520 comprises a tubular wall 1522 in which a generally spiral cut 1524 is formed as is shown in FIGS. 30A and 30C. The spiral cut 1524 can include engaging notches 1526, which facilitate the transmission of rotational force along the tubular wall 1522. In this manner, the transmission member 1522 can be flexible while maintaining sufficient axial force transmission capabilities and can be bent as it is inserted into the sheath assembly 1400 described above. Advantageously, the drill 1500 can be used without or only minimally interfering with the patient's head. As the drill 1500 is bent, it may extend out of the elongated slot 1412 in the sheath assembly 1400 (see FIG. 16). Of course, it is contemplated that other methods can be used to form the flexible transmission member 1520 such as, for example, cuts with different patterns, or transmission members formed of flexible materials such as springs, coils, and/or weaved materials.

Figure 30:
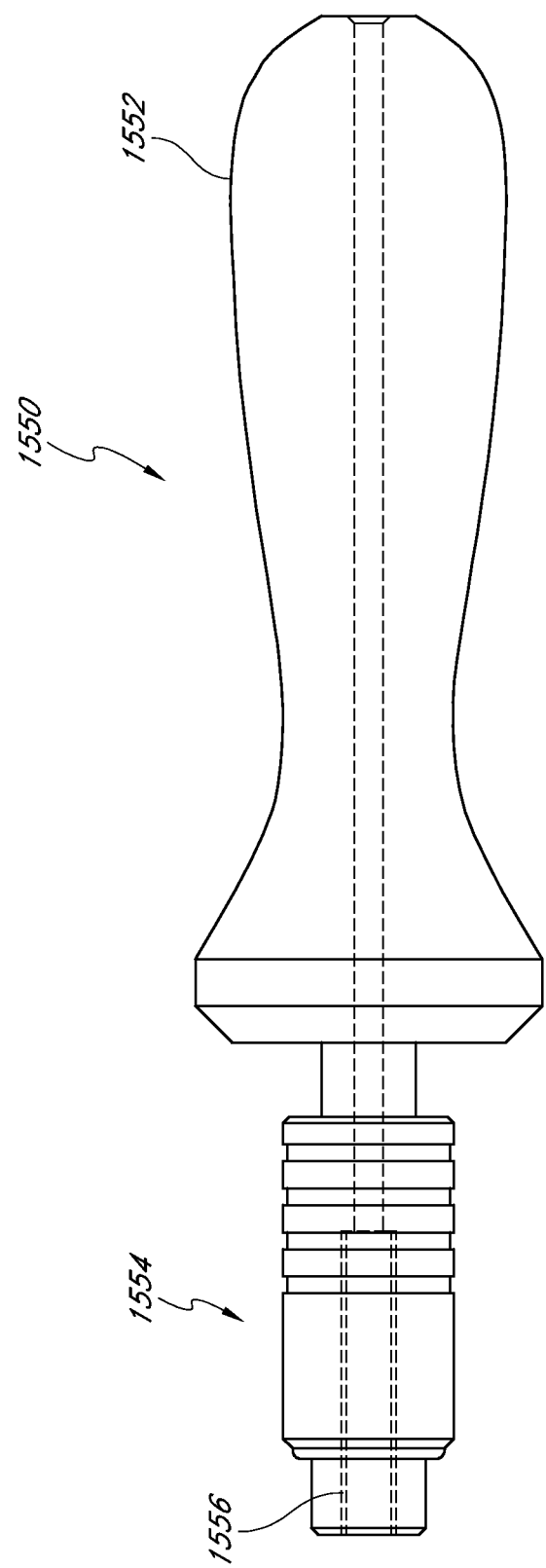
FIG. 30 is a side view of a handle device.

FIG. 30 illustrates a gripping member 1550, which can be coupled to the proximal end 1506 of the drill 1500 described above and to other devices described above. The gripping member 1550 includes a gripping portion 1552 at its proximal end and a distal end 1554. The distal end 1554 includes a cavity 1556 for receiving the proximal end 1506 of the drill 1500. Preferably, the cavity 1556 includes a corresponding shape (e.g., in some embodiments a D-shape to form an AO quick connect with ratcheting features) such that as the gripping member 1550 is rotated the drill 1500 is rotated.

Figure 17:
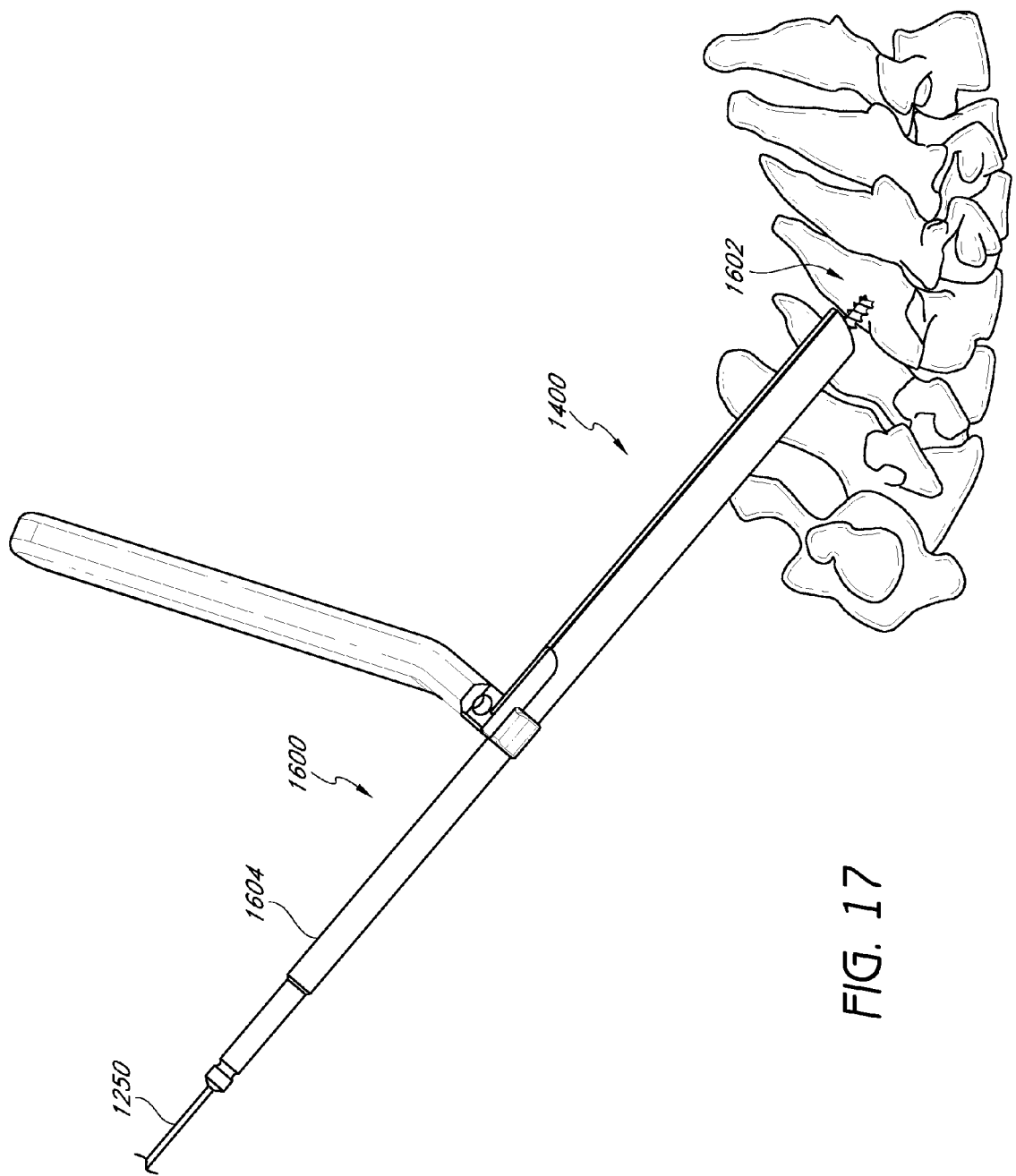
FIG. 17 is a side elevational view of the cervical spine with the guidewire of FIG. 11 and the sheath assembly of FIG. 14 with a tapping device inserted therein.

FIGS. 31A-C illustrates an exemplary embodiment of the tapping device 1600 that was introduced with reference to FIG. 17 above. As mentioned above, the tapping device 1600 can be inserted over the wire 1250 and through the sheath to tap the hole formed in the vertebrae. As shown, the tapping device 1600 comprises a body 1604 having a distal end 1602, a proximal end 1606 an a guidewire lumen 1608 extending therethrough. The proximal end 1606 can be configured to engage any of a variety of driving tools. In the illustrated embodiment, the proximal end 1606 is has a D-shaped cross-section that can be received within the cavity 1556 of the hand held gripping member 1550 described above.

With reference to FIGS. 31B-C, the distal end 1602 is provided with a tapping element 1610 comprising a plurality of threads 1612 and a cutting tip 1614 that corresponds to the distal anchor 234 of the fixation device 212. Between the proximal end 1606 and the distal end 1602 of the device 1600, is an elongated transmission member 1620. In the illustrated embodiment, the transmission member 1620 can be bent about its longitudinal axis as described above with reference to the flexible transmission member 1520 of the drill 1500 illustrated in FIGS. 30A-30B. In one embodiment, the transmission member 1620 is configured in a manner similar to the transmission member 1520 described above.

FIGS. 32A-32B illustrate a driver 1700 which is used to drive the fixation device or implant 212 into the vertebrae as described above with reference to FIG. 18. As shown, the driving device 1700 comprises a body 1704 having a distal end 1702, a proximal end 1706 and a guidewire lumen 1708 extending therethrough. The proximal end 1706 can be configured to engage any of a variety of driving tools. In the illustrated embodiment, the proximal end 1706 is has a D-shaped cross-section that can be received within the cavity 1556 of the hand held gripping member 1550 described above and illustrated in FIG. 30.

With particular reference to FIGS. 32A-B, an outer portion of the distal end 1702 is configured to engage the gripping structure of the proximal anchor 700. In the illustrated embodiment, the distal end is therefore hexagonal in shape and configured to be received by a hexagonal recess of the proximal anchor 700. However, the distal end 1702 can have any of a variety of different shapes for differently shaped gripping structures on the proximal anchor 700 For example, the distal end 1702 can have a pentagonal shape or any other polygonal shape that is similar to the shape of the gripping structure (e.g., the recess 284) of the proximal anchor 700. In still other embodiments, the distal end may 1702 comprise a recess configured to engage a anti-rotational protrusion formed on the proximal anchor 700.

Between the proximal end and the distal end of the device 1700, is an elongated transmission member 1720. In the illustrated embodiment, the transmission member 1720 can be bent about its longitudinal axis as described above with reference to the flecible transmission member 1520 of FIGS. 30A-30B. In one embodiment, the transmission member 1720 is configured in a manner similar to the transmission member 1520 described above.

Figure 19:
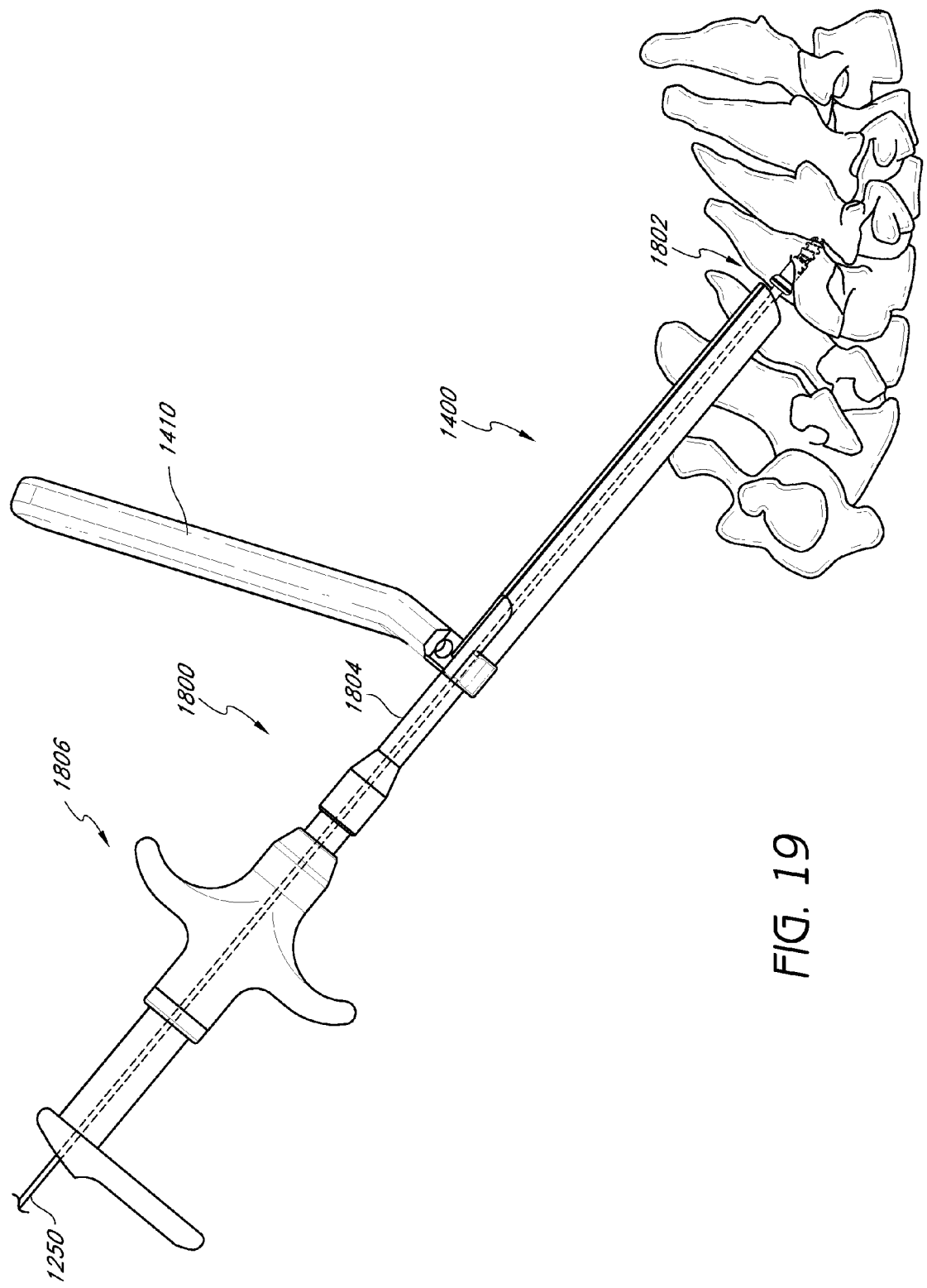
FIG. 19 is a side elevational view of the cervical spine with the guidewire of FIG. 11 and the sheath assembly of FIG. 14 with a compression device inserted therein.

FIGS. 33A-34D illustrate the compression device 1800, which can be used to proximally retract the body 228 with respect to the proximal anchor 700 for the fixation device 212 described above with reference to FIG. 19. With initial reference to FIG. 33A, in the illustrated embodiment, the device 1800 generally includes an elongate syringe-shaped body 1822 having a proximal end 1806, and a distal end 1802. The compression device 1800 also generally comprises a plunger 1828 at the proximal end 1806, a finger grip 1830 attached to a proximal housing 1832 located distally therefrom, and an elongate distal housing 1834 extending distally from the finger grip 1830. As will be apparent from the description below, the device 1800 preferably defines a lumen that extends through the device 1800 such that it may be used over the guidewire 1250.

Figure 33A:
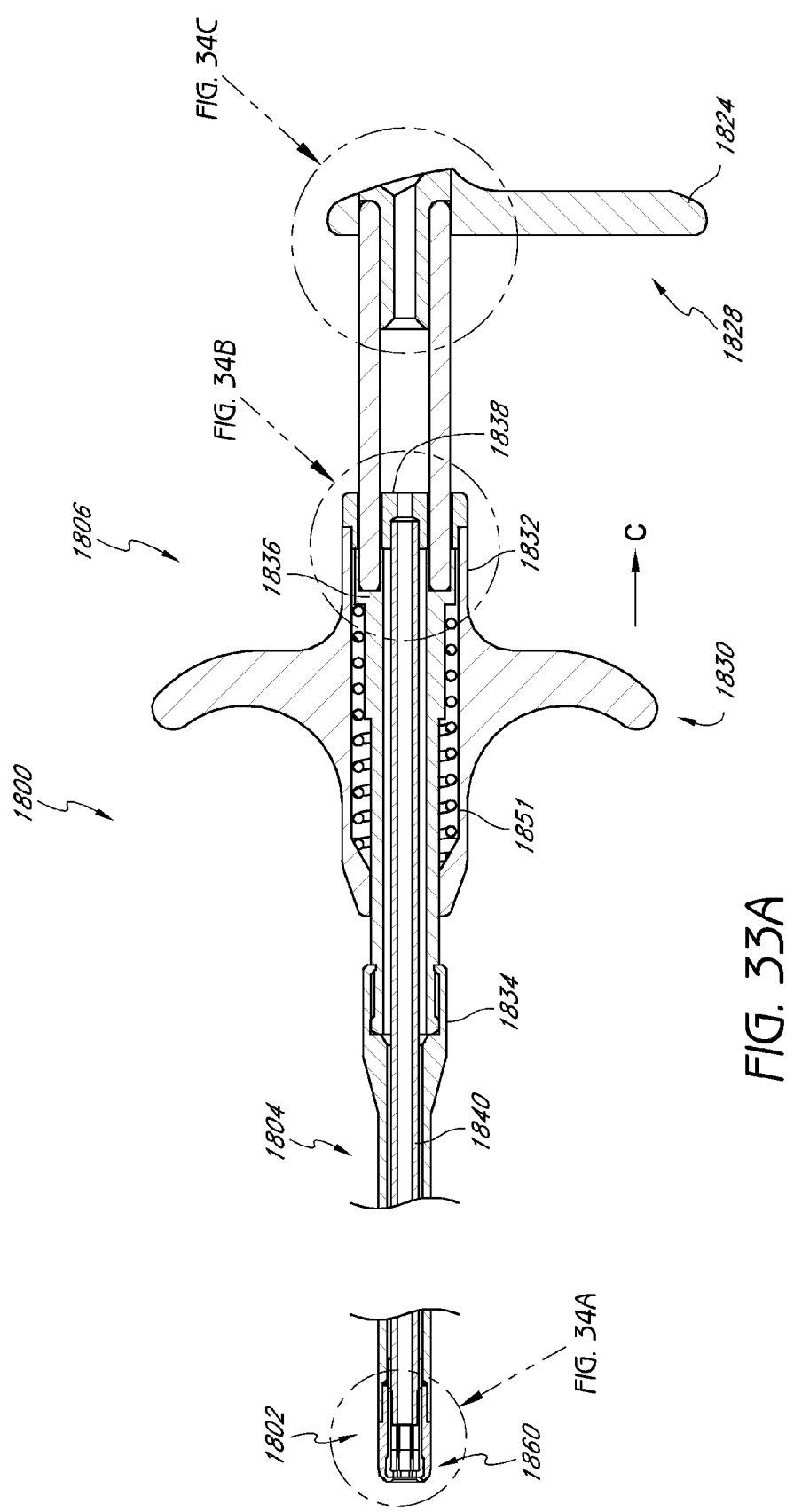
FIG. 33A is a cross-sectional view of the compression device of FIG. 19.
Figure 33J:
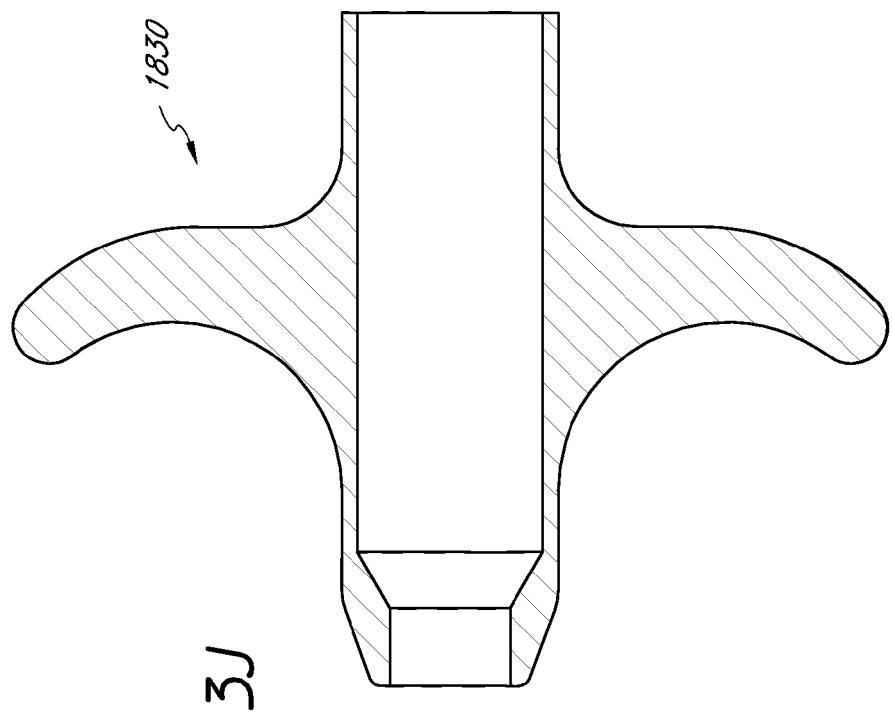
FIG. 33J is a cross sectional view of the grip of FIG. 33I.
Figure 33I:
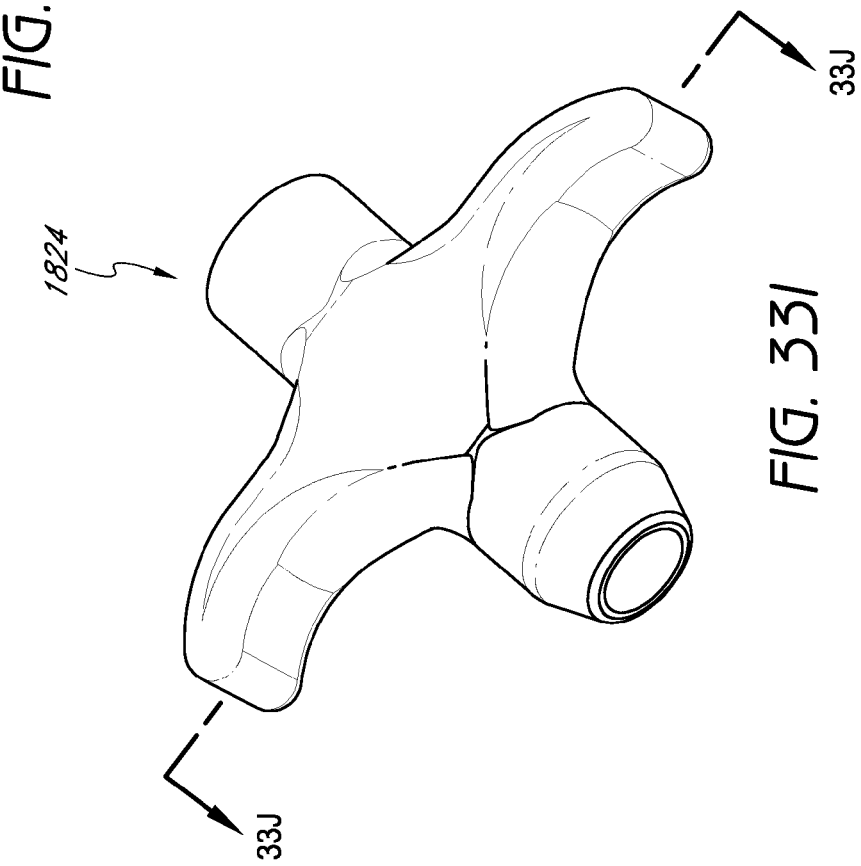
FIG. 33I is a perspective view of a grip of the compression device of FIG. 19

With reference to FIG. 33A, the illustrated embodiment also includes a tensioner member 1840 that can be disposed within the distal housing 1834. A distal end of the tensioner member 1840 can be positioned within a distal cap 1860 (see also FIGS. 33B and 33C). As shown in FIG. 33A and explained below, the distal cap 1860 can be removeably attached to the distal housing 1834 by threads or another removable engagement structure.

As will be explained below, the tensioner member 1840 is configured to move with the finger grip 1830. The member 1840 and grip 1830, in turn, move together relative to the plunger 1828 and distal housing 1834. The tensioner member 1840, in turn, can desirably be configured to grip a proximal end of the body 228 of the bone fixation device 212. In a modified embodiment, the distal housing 1834 and the plunger 1828 may be adapted to move together relative to the finger grip 1830 and tensioner 1840.

The provision of a tensioner member 1840 on the deployment device 1800 generally allows a clinician to provide proximal traction to the body 228 of the bone fixation device 212. In the illustrated embodiment, the syringe-shaped body 1822 is generally adapted such that application of a compressive force between the plunger 1828 and the finger grip 1830 results in engagement of the device 212 on a proximal end of the body 228 in order to provide proximal traction.

As mentioned above, the plunger 1828 is generally adapted to be engaged by the heel of a clinician's hand below the lumen of the device, thus providing a comfortable handle by which the deployment device may be gripped for axial rotation, or a comfortable surface for the compressive force involved in providing traction to a bone fixation device as described elsewhere herein. It is contemplated that numerous specific arrangements of a plunger (or heel-engagement portion) may be provided according to the particular needs of the clinician. Similarly, the finger grip portion shown and described herein is merely provided by way of example. Other shapes and arrangements are available for providing a finger grip portion.

With reference to FIGS. 33A-34D, the plunger 1828, finger grip 1830, distal housing 1834, and traction member 1840 preferably cooperate to cause proximal motion of the traction member 1840 relative to the housing 1834 in response to a proximal motion of the finger grip 1830 relative to the plunger 1828. It is contemplated that in other embodiments, many alternative structural arrangements are possible to provide these desired motions, only some of which are described herein.

In the illustrated embodiment, the plunger 1824 is attached to the distal housing 1834 at a proximal portion 1836 of the housing 1834. The finger grip 1830 is attached to the traction member 1840 by coupling the proximal end 1838 of the traction member 1840 to the proximal housing 1832, which is connected to the grip 1830. Thus, the finger grip 1830 and traction member 1840 can move together and the plunger 1828 and distal housing 1834 can move together. The traction member 1840 can slidably engage the distal housing 1834 as the grip 1830 and plunger 1828 are drawn towards each other. As shown in FIG. 34D, the plunger 1828 is coupled to a proximal portion 1836 of the distal housing through a pair of prongs 1839, which extend through openings 1841 formed in the proximal end of the traction member 1840.

A biasing member 1851 (e.g., a spring) can be positioned within the proximal housing 1832 to bias the proximal portion of the housing 1836 in the direction of arrow C in FIG. 33A.

In the illustrated embodiment, the plunger 1828 can be held generally stationary and the finger grip 1830 can be can be pulled towards the plunger 1824. The finger grip 1830 and the traction member 1840 can both move proximally relative the plunger 1828 and the distal housing 1834 as the traction member 1840 slides smoothly along the distal housing 1834. Of course, many other arrangements are possible for providing the desired motion of the traction member 1840 relative to the distal housing 1834 as a result of a compressive force. For example, a pistol grip can be used. In addition or in combination, the device may employ cable and pulley arrangements, levers, or other structures. The various portions may be attached to one another by adhesives, welds, threads, mechanical fasteners, or any other suitable attachment method.

The traction member 1840 (see FIG. 33H) can comprise a solid rod, a hollow tube, one or more cables, or any other appropriate structure such that it functions as described. The traction member 1840 may be made of any suitable material such that it has sufficient tensile strength that it will not stretch or otherwise deflect significantly during traction of the anchor. Suitable materials usable for the construction of a traction member include stainless steel, nylon, etc. and further materials (e.g., metals, plastic and the like).

As seen in FIGS. 33D-F, the distal end of the traction member 1840 can comprises a collet 1850, which can be adapted to be closed around the proximal end 230 of a bone fixation device 212. The collet 1850 may be fixed to the distal end of the traction member 1840 by any appropriate methods or devices, or the collet 1850 and traction member 1840 may be integrally formed. In one embodiment, the collet 1850 is threaded onto the distal portion of the traction member 1840. Providing a collet with threads advantageously allows collets of varying size to be used interchangeably with a single deployment device 1820 in addition to increasing the ease of cleaning.

In the illustrated embodiment, the collet 1850 comprises a plurality of flexible fingers 1852, each having a gripping head 1854 on its distal end. The flexible fingers 1852 preferably have sufficient tensile strength that the collet 1850 will provide sufficient proximal traction force to a bone fixation device when the deployment device is operated as described herein.

Figure 34A:
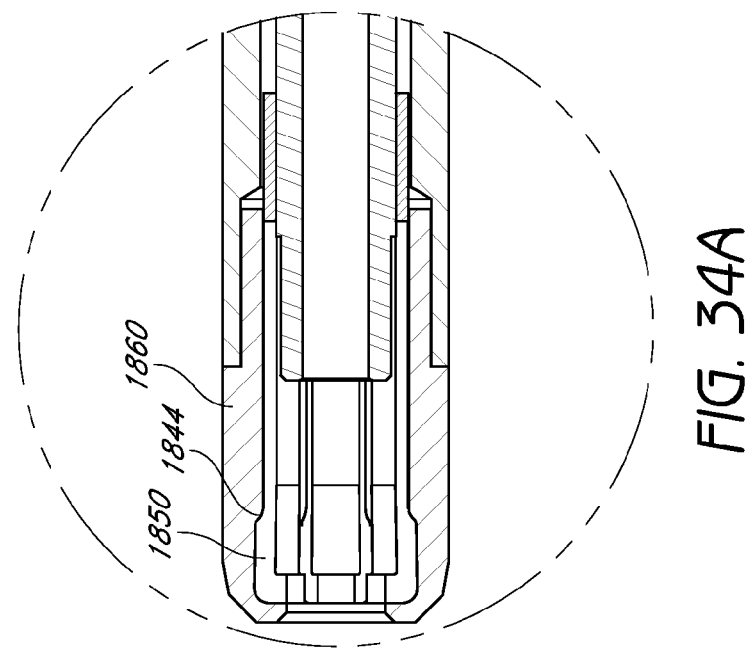
FIG. 34A is a cross-sectional view of the collet and distal cap of the compression device of FIG. 19.
Figure 34B:
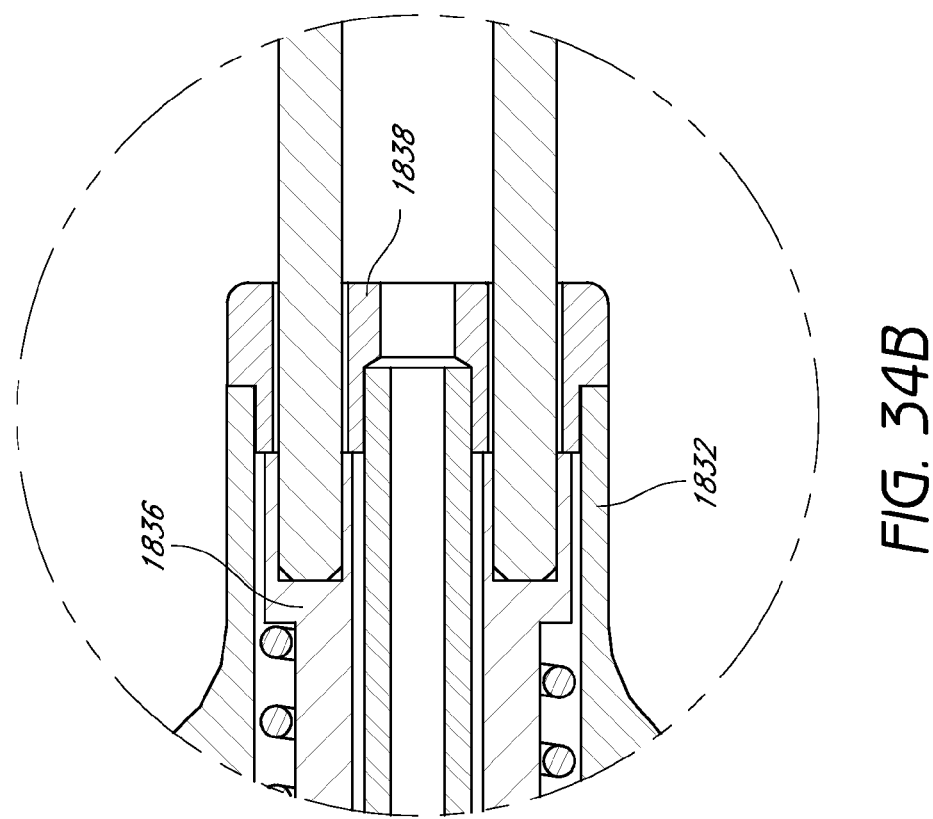
FIG. 34B is a cross-sectional view of a portion of the compression device of FIG. 19.
Figure 34D:
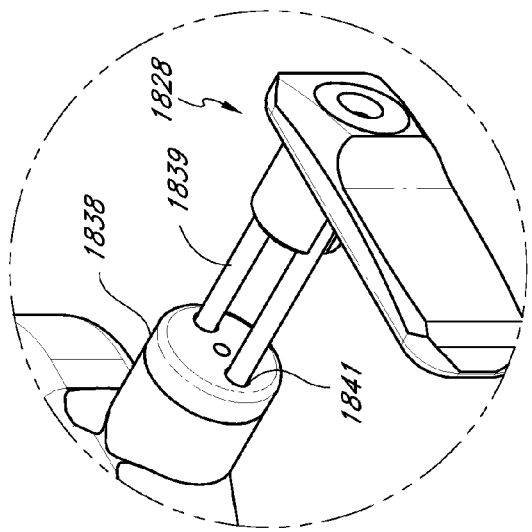
FIG. 34D is a perspective view of a portion of the compression device of FIG. 19.
Figure 34E:
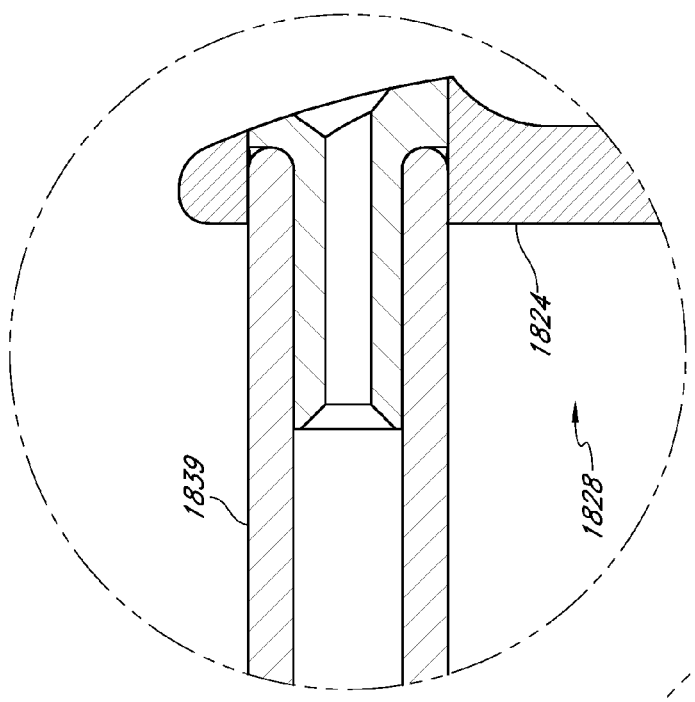
FIG. 34E is a cross-sectional view of a portion of the compression device of FIG. 19.
Figure 34C:
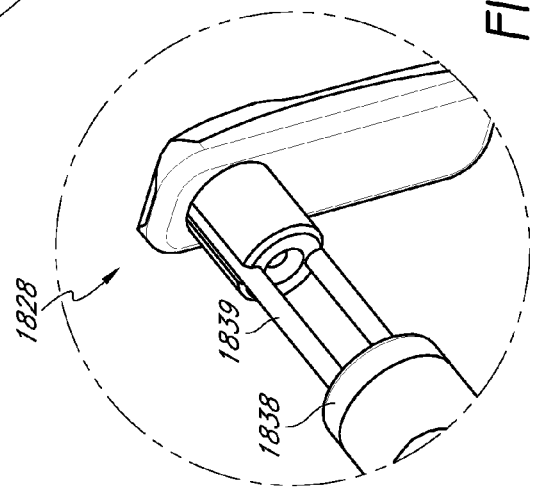
FIG. 34C is a perspective view of a portion of the compression device of FIG. 19.

FIG. 34A is a detailed section view the collet 1850 and with the removable distal cap 1860 shown mounted to the distal end of the housing surrounding the collet 1850 and traction member 1840. In the embodiment shown, the distal edge of the distal housing 1834 comprises a closing surface 1844 formed by a constriction or reduction in diameter. The closing surface 1844 causes the collet 1850 to close as it moves distally relative to the collet 1850. In one embodiment, the closing surfaces 1844 can contact and move inwardly the gripping heads 1854 as the closing surfaces 1844 move distally relative the collet 1850. The collet closing surface 1844 can alternatively be provided as a constriction in the inner diameter of the distal cap 1860.

As mentioned above, the distal cap 1860 may be threaded or otherwise attached, such as by adhesives, welds, etc. to the distal housing 1834. A removable distal cap, however, can be advantageous in certain embodiments because it allows for greatly simplified cleaning of the deployment device tip. Many embodiments of a distal cap 1860 may be provided depending on the particular application. A distal cap 1860 such as that shown in FIG. 33B, can be provided to abut the flange of the proximal anchor 700 for proximally retracting the anchor as discussed above. Of course in modified embodiments, the distal cap 1860 may include a different shape head or recess as appropriate given the structure of the proximal anchor 700.

Preferably the compression device 1800 can be bent about its longitudinal axis as described above with reference to FIGS. 30A-30B. In one embodiment, the various portions of the compression device 1800 can be configured in a manner similar to the transmission member 1520 described above.

In one embodiment of use, once the distal anchor 234 has been positioned, the finger grip 1830 and plunger 1828 of the compression device 1800 are compressed and the traction member 1840 moves proximally relative to the distal housing 1834 until the gripping heads 1854 engage from the closing surface 1844, thereby causing the gripping heads 1854 to be displaced toward the pin 228. As the traction member 1840 continues to be proximally retracted, the gripping heads 1854 eventually engage the proximal flange of the pin 228 thereby allowing the pin 228 and the distal anchor 234 to be pulled proximally relative to the proximal anchor 700. Once the fixation device 212 has been sufficiently retracted, and the superior and inferior vertebrae rigidly coupled together, the second portion of the body 228 can be removed as described below. Modified embodiments, components and/or details of an exemplary embodiment of a compression device can be found in U.S. Patent Publication No. 2004/0260289, filed Mar. 1, 2004, application Ser. No. 10/790,671, which is hereby incorporated by reference herein in its entirety.

Figure 35A:
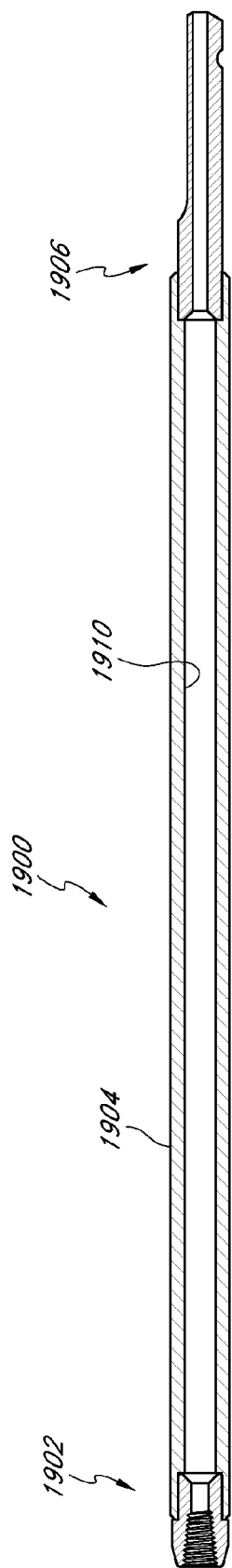
FIG. 35A is a cross-sectional view of the pin removal device of FIG. 20.
Figure 35B:
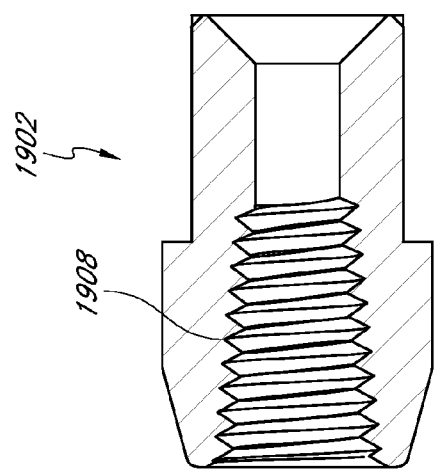
FIG. 35B is an enlarged cross-sectional view of a portion of the pin removal device of FIG. 20.

FIGS. 35A-B illustrate an exemplary embodiment of the pin remover device 1900 that was introduced with reference to FIG. 20 above. As mentioned above, the pull-pin remover device 1900 can be inserted over the wire 1250 and through the sheath assembly 1400 to remove a second portion of the body 228 of the fixation device 212. In the illustrated embodiment, the device 1900 comprises a body 1904 having a distal end 1902, a proximal end 1906 and a guidewire lumen 1910 extending therethrough. The proximal end 1906 can be configured to engage any of a variety of driving tools. In the illustrated embodiment, the proximal end 1906 is has a D-shaped cross-section that can be received within the cavity 1556 of the hand held gripping member 1550 described above.

With reference to FIG. 35B, the distal end 1902 can be provided with a substantially conical threaded cavity 1908. In the illustrated embodiment, the threads of the threaded cavity 1908 are in the opposite direction of the threads that are used to couple the first and second portions of the body 228 of the fixation device. Thus, in use, the distal end 1902 is advanced through the sheath 1400 until the threaded cavity 1908 engages the flange 270 on the proximal end of the fixation device. Then, by rotating the device 1900 the threads engaged the flange 270. At a certain point, further rotation between the device 1900 and the flange 270 is inhibited by the conical nature of the threaded cavity 1908. At this point, further rotations caused the second portion 238 of the body 228 to be rotated with respect to the first portion causing the first and second portions to be decoupled from each other. Once the second portion is sufficiently decoupled, the device 1900 can be withdrawn to remove the pull pin 238 from the patient.

It should be noted above that the tools above can have dedicated handles instead of interchangeable handles.

In the illustrated embodiment, the body 1904 can be bent about its longitudinal axis as described above with reference to FIGS. 30A-30B. In one embodiment, the transmission body 1904 can be configured in a manner similar to the transmission member 1520 described above.

The specific dimensions of any of the devices described above can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

We claim:

1. A system for coupling a first superior vertebra of a cervical spine to a second inferior vertebra, the system comprising:
   a fixation device having a distal end and a proximal end, the distal end configured to extend between the first superior vertebra and the second inferior vertebra;
   an elongated tubular device configured to apply the fixation device, the elongated tubular device having a first longitudinal axis and a handle extending along a second longitudinal axis, the first and second longitudinal axes forming an angle with respect to each other such that when the elongated tubular device is applied to the cervical spine from a direction above the cervical spine, the fixation device can be applied without interference from the head of the patient; and the elongated tubular device having a proximal opening extending from the proximal end of the elongated tubular device, the proximal opening configured to allow instruments to move toward a line transverse to the first longitudinal axis.

2. The system of claim 1, wherein the elongated tubular device comprises a sheath assembly providing a passage between a first opening above the cervical spine and a second opening positioned adjacent the cervical spine to allow passage of a tool therethrough without interference from the head of the patient.

3. The system as in claim 1, wherein the handle comprises a gripping portion that is separated from the elongated tubular device by an elongated extension member.

4. The system of claim 1, further comprising at least one flexible member.

5. The system of claim 1, further comprising a tool configured to drive the fixation device.

6. The system of claim 1, further comprising a tapping device.

7. The system of claim 1, further comprising a fascia cutting device.

8. The system of claim 7, wherein the fascia cutter comprises an elongated body having a proximal end, a distal end and a lumen extending therethrough, the lumen having a distal opening at the distal end and a proximal opening at the proximal end, and a plurality of cutting elements positioned on the distal end of the elongated body, each of the plurality of cutting elements defining a cutting edge that extends generally radially from the distal end of the lumen.

9. The system of claim 4, further comprising a drilling device, and wherein the flexible member comprises a flexible transmission member of the drilling device.

10. The system of claim 1, further comprising a curved elongated member.

11. A system for establishing access for a fixation device configured to extend between a first superior vertebra of a cervical spine to a second inferior vertebra, the system comprising:

an elongated tubular device having a first longitudinal axis and a handle extending along a second longitudinal axis, the first and second longitudinal axis form an angle with respect to each other;

a elongated flexible member having a distal end and a proximal end, the distal end of the elongated flexible member being coupled to a tool and the proximal end of the elongated flexible member being coupled to a second handle; and wherein the elongated flexible member allows the proximal end to be flexed toward a line transverse to the first longitudinal axis while the distal end maintains a desired position and orientation with respect to the vertebra.

12. The system as in claim 11, wherein the distal end of the elongated flexible member is configured to be inserted through the elongated tubular device.

13. A method of providing spinal fixation in a cervical spine, the method comprising:

providing an introducer comprising an elongated cannulated member and a handle coupled to the elongated cannulated member, the handle having a gripping portion;

positioning the gripping portion of the handle above the elongated cannulated member to reduced interference from the back of the patient's head;

advancing a distal end of the elongated cannulated member with a trocar positioned therein to a first, superior vertebra in the cervical spine to establish a tissue tract;

removing the trocar from the elongated cannulated member;

advancing a first guidewire though the elongated cannulated member and at least partially into the first vertebra;

removing the first guidewire from the elongated cannulated member;

advancing a second guidewire through the elongated cannulated member; and removing the elongated cannulated member.

14. The method of claim 13, further comprising advancing a fixation device over the second guidewire.

15. The method of claim 14, further comprising advancing a deployment device coupled to the fixation device over the second guidewire.

16. The method of claim 13, further comprising advancing a fascia cutter with at least one sharp element on a distal end thereof over the second guidewire.

17. The method of claim 13, further comprising:

advancing at least one flexible transmission member through the elongated cannulated member; and inserting a distal end of a fixation device through the elongated cannulated member and through the first vertebrae and into the second vertebrae; and wherein the at least one flexible transmission member is used to perform at least one of the following steps:

tap a hole in the cervical spine;

rotate the fixation device; or apply proximal retraction to a portion of the fixation device.

18. The method of claim 13, wherein the elongated cannulated member is curved, and further comprising the step of inserting a distal end of a fixation device through the curved cannulated member device and through the first vertebrae and into the second vertebrae.

19. The method of claim 13, further comprising advancing a dilation device over the second guidewire and inserting a distal end of a fixation device through the dilation device and through the first vertebra and into the second vertebra.

20. A method of placing a guidewire near a cervical portion of the spine, the method comprising:

advancing an elongated member along a first longitudinal axis extending from the cervical portion of the spine toward the head of the patient while grasping a gripping portion of a handle coupled to the elongated member, the gripping portion located above and angularly offset from the elongated member; and inserting a guidewire through the elongated member.

\* \* \* \* \*